(12) United States Patent
Davenport et al.

(10) Patent No.: US 8,912,176 B2
(45) Date of Patent: Dec. 16, 2014

(54) AZETIDINES AS HISTAMINE H3 RECEPTOR ANTAGONISTS

(75) Inventors: Adam James Davenport, Abingdon Oxfordshire (GB); David James Hallett, Marlow (GB); Christopher Charles Stimson, Oxford (GB)

(73) Assignee: Evotec AG, Hamburg (DE)

( * ) Notice: Subject to any disclaimer, the term of this patent is extended or adjusted under 35 U.S.C. 154(b) by 244 days.

(21) Appl. No.: 13/147,337

(22) PCT Filed: Jan. 29, 2010

(86) PCT No.: PCT/EP2010/051077
§ 371 (c)(1),
(2), (4) Date: Sep. 23, 2011

(87) PCT Pub. No.: WO2010/086403
PCT Pub. Date: Aug. 5, 2010

(65) Prior Publication Data
US 2012/0040952 A1 Feb. 16, 2012

Related U.S. Application Data

(60) Provisional application No. 61/151,395, filed on Feb. 10, 2009.

(30) Foreign Application Priority Data

Feb. 2, 2009 (EP) .................................. 09151866
Dec. 22, 2009 (EP) .................................. 09180478

(51) Int. Cl.
| | | |
|---|---|---|
| A61K 31/551 | (2006.01) | |
| C07D 243/08 | (2006.01) | |
| C07D 413/14 | (2006.01) | |
| C07D 403/14 | (2006.01) | |
| C07D 405/14 | (2006.01) | |

(52) U.S. Cl.
CPC ............ C07D 403/14 (2013.01); C07D 413/14 (2013.01); C07D 405/14 (2013.01)
USPC ..................................... 514/210.18; 540/575

(58) Field of Classification Search
USPC .................... 11/210.18; 540/575; 514/210.18
See application file for complete search history.

(56) References Cited

U.S. PATENT DOCUMENTS

| 4,956,359 A | 9/1990 | Taylor, Jr. et al. |
| 2001/0049367 A1 | 12/2001 | Bennani et al. |

FOREIGN PATENT DOCUMENTS

| WO | WO 01/66534 A2 | 9/2001 |
| WO | WO 2004/101507 A2 | 11/2004 |
| WO | WO 2006/040192 A1 | 4/2006 |
| WO | WO 2006/136924 A1 | 12/2006 |
| WO | WO 2007/080140 A1 | 7/2007 |
| WO | WO 2009/024823 A2 | 2/2009 |
| WO | WO 2009/095394 A1 | 8/2009 |
| WO | WO 2009/135842 A1 | 11/2009 |
| WO | WO 2010/026113 A1 | 3/2010 |
| WO | WO 2010/052222 A1 | 5/2010 |

OTHER PUBLICATIONS

Arrang et al., "Auto-inhibition of brain histamine release mediated by a novel class (H3) of histamine receptor", Nature, vol. 302, Apr. 28, 1983, pp. 832-837.
Bongers et al., "Molecular aspects of the histamine H3 receptor", Biochemical Pharmacology 73, 2007, pp. 1195-1204.
Cannon et al., "Immunohistochemical localization of histamine H3 receptors in rodent skin, dorsal root ganglia, superior cervical ganglia, and spinal cord: Potential antinociceptive targets", Pain, 129, 2007 pp. 76-92.
Drutel et al., "Identification of Rat H3 Receptor Isoforms with Different Brain Expression and Signaling Properties", Molecular Pharmacology, vol. 59, No. 1, pp. 1-8, 2001.
Esbenshade et al., "Histamine H3 Receptor Antagonists: Preclinical Promise for Treating Obesity and Cognitive Disorders", Molecular Interventions, vol. 6, Issue 2, Apr. 2006, pp. 77-88.
Hancock et al., "Assessment of pharmacology and potential anti-obesity properties of H3 receptor antagonists/inverse agonists", Expert Opin. Investig. Drugs, 14(3), 2005 pp. 223-241.
Martinez-Mir et al., "Three histamine receptors (H1, H2 and H3) visualized in the brain of human and non-human primates", Brain Research, 526, 1990 pp. 322-327.
Morisset et al., "High constitutive activity of native H3 receptors regulates histamine neurons in brain", Nature, vol. 408, Dec. 14, 2000, pp. 860-864.
Witkin et al., "Selective histamine H3 receptor antagonists for treatment of cognitive deficiencies and other disorders of the central nervous system", Pharmacology & Therapeutics, vol. 103, 2004, pp. 1-20.
English translation of Japanese Notice of Reasons for Rejection, dated Feb. 13, 2014, for Japanese Application No. 2011-546855.

Primary Examiner — Brenda Coleman
(74) Attorney, Agent, or Firm — Birch, Stewart, Kolasch & Birch, LLP

(57) ABSTRACT

The invention relates to compounds of formula (I), wherein R, $R^1$, m, n and $X^1$ to $X^3$ have the meaning as cited in the description and the claims. Said compounds are useful as Histamine H3 receptor antagonists. The invention also relates to pharmaceutical compositions, the preparation of such compounds as well as the production and use as medicament.

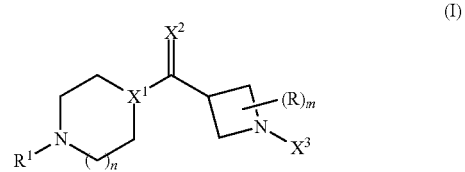

(I)

14 Claims, No Drawings

AZETIDINES AS HISTAMINE H3 RECEPTOR ANTAGONISTS

CROSS REFERENCE TO RELATED APPLICATIONS

This application is the National Phase of PCT/EP2010/051077 filed on Jan. 29, 2010, which claims priority under 35 U.S.C. 119(e) to U.S. Provisional Application No. 61/151,395 filed on Feb. 10, 2009 and to Pat. Application Nos. 09151866.2 and 09180478.1 filed in European Patent Application, on Feb. 2, 2009 and Dec. 22, 2009. The entire contents of all of the above applications are hereby incorporated by reference into the present application.

The present invention relates to Histamine H3 receptor antagonists, pharmaceutical compositions thereof, the preparation of such compounds as well as the production and use as medicament.

The histamine H3 receptor is a G protein-coupled receptor (GPCR) and one out of four receptors of the histamine receptor family. Histamine receptors have long been attractive drug targets, mirrored in the development of antihistamines, which were directed at the histamine H1 receptor for the treatment of allergic reactions or at the histamine H2 receptor to ameliorate gastric ulcers by inhibiting gastric acid secretion. The H3 receptor has been identified as a presynaptic autoreceptor, regulating the release of histamine (Arrang et al. (1983) Nature: 302; 832-837), as well as a heteroreceptor that regulates the release of many other important neurotransmitters (acetylcholine, norepinephrine, dopamine, and serotonin). Structurally divergent H3 receptor antagonists/inverse agonists have been developed and shown to comprise activity in a variety of cognition tests in mice and rat (e.g. Esbenshade et al. (2006) Mol Interventions: 6 (2); 77-88) as well as in models for sleeping disorders and energy balance. From these studies it is concluded that such antagonists comprise a potential treatment for a variety of disorders affecting cognition (e.g., Alzheimer's disease, Parkinson's disease, Attention Deficit and Hyperactivity Disorder, Schizophrenia, Foetal Alcohol Syndrome, Mild Cognitive Impairment, Age-related Memory Dysfunction, Down Syndrome and others), as well as sleep (e.g., hypersomnia and narcolepsy), and energy homeostasis (e.g. obesity) (Witkin & Nelson (2004) JPET: 103; 1-20; Hancock & Brune (2005) Exp Opin Inves Drugs: 14 (3), 223-241).

Accordingly, histamine H3 receptor antagonists are described in the art for the treatment of the above mentioned diseases and disorders.

In WO-A 2007/080140 cyclylhexyl piperazinyl methanone derivatives are disclosed, which are useful as H3 receptor modulators.

In WO-A 2006/136924 cyclobutyl derivatives are disclosed as histamine-3 receptor antagonists.

WO-A 2001/66534 and US-A 2001/049367 relate to the preparation of cyclic and bicyclic diamino histamine-3 receptor antagonists.

However there is a continuing need for new compounds useful as histamine H3 receptor antagonists.

Thus, an object of the present invention is to provide a new class of compounds as Histamine H3 receptor antagonists which may be effective in the treatment of H3 receptor related diseases and may show improved pharmaceutically relevant properties including activity, ADME properties and/or reduced side effects.

Accordingly, the present invention provides compounds of formula (I)

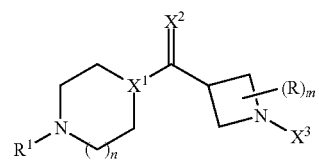

or a pharmaceutically acceptable salt, prodrug or metabolite thereof, wherein $R^1$ is $C_{1-5}$ alkyl; $C_{2-5}$ alkenyl; $C_{2-5}$ alkynyl; or $T^0$, wherein $C_{1-5}$ alkyl; $C_{2-5}$ alkenyl; $C_{2-5}$ alkynyl are optionally substituted with one or more substituents, which are the same or different and selected from the group consisting of halogen; OH; $OCH_3$; $OCH_2F$; $OCHF_2$; $OCF_3$; CN; and $T^0$;

$T^0$ is $C_{3-5}$ cycloalkyl; or 4 to 5 membered saturated heterocyclyl, wherein $T^0$ is optionally substituted with one or more substituents, which are the same or different and selected from the group consisting of halogen; $C_{1-5}$ alkyl; $C_{2-5}$ alkenyl; $C_{2-5}$ alkynyl; OH; O—$C_{1-5}$ alkyl; O—$C_{2-5}$ alkenyl; O—$C_{2-5}$ alkynyl; and CN, wherein $C_{1-5}$ alkyl; $C_{2-5}$ alkenyl; $C_{2-5}$ alkynyl; O—$C_{1-5}$ alkyl; O—$C_{2-5}$ alkenyl; and O—$C_{2-5}$ alkynyl are optionally substituted with one or more halogen, which are the same or different;

n is 1 or 2;

$X^1$ is N; or CH;

$X^2$ is O; S; N—CN; N—OH; or N—$OC_{1-4}$ alkyl;

$X^3$ is $(CH_2)_{n1}X^4(CH_2)_{n2}R^2$;

R is F;

m is 0, 1, 2, 3, or 4;

n1; n2 are independently selected from the group consisting of 0; 1; and 2;

$X^4$ is C(O); C(O)O; OC(O); O; C(O)N($R^{1a}$); N($R^{1a}$)C(O); S(O)$_2$N($R^{1a}$); N($R^{1a}$)S(O)$_2$; S(O)N($R^{1a}$); N($R^{1a}$)S(O); S(O)$_2$; S(O); N($R^{1a}$)S(O)$_2$N($R^{1b}$); S; N($R^{1a}$); N($R^{1a}$)C(O)N($R^{1b}$); N($R^{1a}$)C(O)O; or OC(O)N($R^{1a}$);

$R^{1a}$, $R^{1b}$ are independently selected from the group consisting of H; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more halogen, which are the same or different;

$R^2$ is H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^3$ is halogen; CN; C(O)$R^4$; C(O)O$R^4$; O$R^4$; C(O)N($R^4R^{4a}$); S(O)$_2$N($R^4R^{4a}$); S(O)N($R^4R^{4a}$); S(O)$_2R^4$; S(O)$R^4$; N($R^4$)S(O)$_2$N($R^{4a}R^{4b}$); S$R^4$; N($R^4R^{4a}$); NO$_2$; OC(O)$R^4$; N($R^4$)C(O)$R^{4a}$; N($R^4$)SO$_2R^{4a}$; N($R^4$)S(O)$R^{4a}$; N($R^4$)C(O)N($R^{4a}R^{4b}$); N($R^4$)C(O)O$R^{4a}$; OC(O)N($R^4R^{4a}$); or T;

$R^4$, $R^{4a}$, $R^{4b}$ are independently selected from the group consisting of H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^5$, which are the same or different;

$R^5$ is halogen; CN; C(O)$R^6$; C(O)O$R^6$; O$R^6$; C(O)N($R^6R^{6a}$); S(O)$_2$N($R^6R^{6a}$); S(O)N($R^6R^{6a}$); S(O)$_2R^6$; S(O)$R^6$; N($R^6$)S(O)$_2$N($R^{6a}R^{6b}$); S$R^6$; N($R^6R^{6a}$); NO$_2$; OC(O)$R^6$; N($R^6$)C(O)$R^{6a}$; N($R^6$)SO$_2R^{6a}$; N($R^6$)S(O)$R^{6a}$; N($R^6$)C(O)N($R^{6a}R^{6b}$); N($R^6$)C(O)O$R^{6a}$; OC(O)N($R^6R^{6a}$); or T;

$R^6$, $R^{6a}$, $R^{6b}$ are independently selected from the group consisting of H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

T is phenyl; naphthyl; azulenyl; indenyl; indanyl; $C_{3-7}$ cycloalkyl; 3 to 7 membered heterocyclyl; or 7 to 11 membered heterobicyclyl, wherein T is optionally substituted with one or more $R^7$, which are the same or different;

$R^7$ is halogen; CN; C(O)OR$^8$; OR$^8$; C(O)R$^8$; C(O)N(R$^8$R$^{8a}$); S(O)$_2$N(R$^8$R$^{8a}$); S(O)N(R$^8$R$^{8a}$); S(O)$_2$R$^8$; S(O)R$^8$; N(R$^8$)S(O)$_2$N(R$^{8a}$R$^{8b}$); SR$^8$; N(R$^8$R$^{8a}$); NO$_2$; OC(O)R$^8$; N(R$^8$)C(O)R$^{8a}$; N(R$^8$)S(O)$_2$R$^{8a}$; N(R$^8$)S(O)R$^{8a}$; N(R$^8$)C(O)OR$^{8a}$; N(R$^8$)C(O)N(R$^{8a}$R$^{8b}$); OC(O)N(R$^8$R$^{8a}$); oxo (=O), where the ring is at least partially saturated; T$^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^8$, $R^{8a}$, $R^{8b}$ are independently selected from the group consisting of H; T$^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{10}$, which are the same or different;

$R^9$, $R^{10}$ are independently selected from the group consisting of halogen; CN; C(O)R$^{11}$; C(O)OR$^{11}$; OR$^{11}$; C(O)N(R$^{11}$R$^{11a}$); S(O)$_2$N(R$^{11}$R$^{11a}$); S(O)N(R$^{11}$R$^{11a}$); S(O)$_2$R$^{11}$; S(O)R$^{11}$; N(R$^{11}$)S(O)$_2$N(R$^{11a}$R$^{11b}$); SR$^{11}$; N(R$^{11}$R$^{11a}$); NO$_2$; OC(O)R$^{11}$; N(R$^{11}$)C(O)R$^{11a}$; N(R$^{11}$)SO$_2$R$^{11a}$; N(R$^{11}$)S(O)R$^{11a}$; N(R$^{11}$)C(O)N(R$^{11a}$R$^{11b}$); N(R$^{11}$)C(O)OR$^{11a}$; OC(O)N(R$^{11}$R$^{11a}$); and T$^1$;

$R^{11}$, $R^{11a}$, $R^{11b}$ are independently selected from the group consisting of H; T$^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

T$^1$ is phenyl; $C_{3-7}$ cycloalkyl; or 3 to 7 membered heterocyclyl, wherein T$^1$ is optionally substituted with one or more $R^{12}$, which are the same or different;

$R^{12}$ is halogen; CN; C(O)OR$^{13}$; OR$^{13}$; C(O)R$^{13}$; C(O)N(R$^{13}$R$^{13a}$); S(O)$_2$N(R$^{13}$R$^{13a}$); S(O)N(R$^{13}$R$^{13a}$); S(O)$_2$R$^{13}$; S(O)R$^{13}$; N(R$^{13}$)S(O)$_2$N(R$^{13a}$R$^{13b}$); SR$^{13}$; N(R$^{13}$R$^{13a}$); NO$_2$; OC(O)R$^{13}$; N(R$^{13}$)C(O)R$^{13a}$; N(R$^{13}$)S(O)$_2$R$^{13a}$; N(R$^{13}$)S(O)R$^{13a}$; N(R$^{13}$)C(O)OR$^{13a}$; N(R$^{13}$)C(O)N(R$^{13a}$R$^{13b}$); OC(O)N(R$^{13}$R$^{13a}$); oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different.

In case a variable or substituent in formula (I) as defined above can be selected from a group of different variants and such variable or substituent occurs more than once the respective variants can be the same or different.

Within the meaning of the present invention the terms are used as follows:

"Alkyl" means a straight-chain or branched saturated hydrocarbon chain. Each hydrogen of an alkyl carbon may be replaced by a substituent as further specified.

"Alkenyl" means a straight-chain or branched hydrocarbon chain that contains at least one carbon-carbon double bond. Each hydrogen of an alkenyl carbon may be replaced by a substituent as further specified.

"Alkynyl" means a straight-chain or branched hydrocarbon chain that contains at least one carbon-carbon triple bond. Each hydrogen of an alkynyl carbon may be replaced by a substituent as further specified.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl, tert-butyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a $C_{1-4}$ alkyl carbon may be replaced by a substituent as further specified.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, when two moieties of a molecule are linked by the alkyl group. Each hydrogen of a $C_{1-6}$ alkyl carbon may be replaced by a substituent as further specified. The term "$C_{1-5}$ alkyl" is defined accordingly.

"$C_{2-6}$ alkenyl" means an alkenyl chain having 2 to 6 carbon atoms, e.g. if present at the end of a molecule: —CH=CH$_2$, —CH=CH—CH$_3$, —CH$_2$—CH=CH$_2$, —CH=CH—CH$_2$—CH$_3$, —CH=CH—CH=CH$_2$, or e.g. —CH=CH—, when two moieties of a molecule are linked by the alkenyl group. Each hydrogen of a $C_{2-6}$ alkenyl carbon may be replaced by a substituent as further specified. The terms "$C_{2-4}$ alkenyl" and "$C_{2-5}$ alkenyl" are defined accordingly.

"$C_{2-6}$ alkynyl" means an alkynyl chain having 2 to 6 carbon atoms, e.g. if present at the end of a molecule: —C≡CH, —CH$_2$—C≡CH, CH$_2$—CH$_2$—C≡CH, CH$_2$—C≡C—CH$_3$, or e.g. —C≡C— when two moieties of a molecule are linked by the alkynyl group. Each hydrogen of a $C_{2-6}$ alkynyl carbon may be replaced by a substituent as further specified. The terms "$C_{2-4}$ alkynyl" and "$C_{2-5}$ alkynyl" are defined accordingly.

"$C_{3-7}$ cycloalkyl" or "$C_{3-7}$ cycloalkyl ring" means a cyclic alkyl chain having 3 to 7 carbon atoms, e.g. cyclopropyl, cyclobutyl, cyclopentyl, cyclohexyl, cycloheptyl. Each hydrogen of a cycloalkyl carbon may be replaced by a substituent as further specified. The term "$C_{3-5}$ cycloalkyl" is defined accordingly.

"Halogen" means fluoro, chloro, bromo or iodo. It is generally preferred that halogen is fluoro or chloro.

"3 to 7 membered heterocyclyl" or "3 to 7 membered heterocycle" means a ring with 3, 4, 5, 6 or 7 ring atoms that may contain up to the maximum number of double bonds (aromatic or non-aromatic ring which is fully, partially or un-saturated) wherein at least one ring atom and up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3 to 7 membered heterocycles are azeridine, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. The term "4 to 5 membered heterocyclyl" or "4 to 5 membered heterocycle" is defined accordingly. The term "5 to 6 membered heterocyclyl" or "5 to 6 membered heterocycle" is defined accordingly.

"4 to 5 membered saturated heterocyclyl" or "4 to 5 membered saturated heterocycle" means a "4 to 5 membered heterocyclyl" or "4 to 5 membered heterocycle" without double bonds in the ring.

"7 to 11 membered heterobicyclyl" or "7 to 11 membered heterobicycle" means a heterocyclic system of two rings with 7 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 7 to 11 membered heterobicycles are imidazo[1,5-a]pyridine, imidazo[2,1-b][1,3]oxazole, imidazo[2,1-b][1,3]thiazole, 5,6,7,8-tetrahydro-1,6-naphthyridine, indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 7 to 11 membered heterobicycle also includes spiro structures of two rings like 1,4-dioxa-8-azaspiro[4.5]decane or bridged heterocycles like 8-aza-bicyclo[3.2.1]octane. The term "8 to 11 membered heterobicyclyl" or "8 to 11 membered heterobicycle" is defined accordingly.

"5 to 6 membered aromatic heterocyclyl" or "5 to 6 membered aromatic heterocycle" means a heterocycle derived from cyclopentadienyl or benzene, where at least one carbon atom is replaced by a heteroatom selected from the group consisting of sulfur (including —S(O)—, —S(O)$_2$—), oxygen and nitrogen (including =N(O)—). Examples for such heterocycles are furan, thiophene, pyrrole, imidazole, pyrazole, oxazole, isoxazole, thiazole, isothiazole, thiadiazole, pyranium, pyridine, pyridazine, pyrimidine, triazole, tetrazole.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts as well as their isotopic derivatives.

In preferred embodiments of the present invention, the substituents R, $R^1$, m, n and $X^1$ to $X^3$ of formula (I) independently have the following meaning Hence, one or more of the substituents R, $R^1$, m, n and $X^1$ to $X^3$ can have the preferred or more preferred meanings given below.

Preferably, $R^1$ is $C_{1-5}$ alkyl; $C_{2-5}$ alkenyl; $C_{2-5}$ alkynyl; $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; or 4 to 5 membered saturated heterocyclyl, wherein $C_{1-5}$ alkyl; $C_{2-5}$ alkenyl; $C_{2-5}$ alkynyl are optionally substituted with one or more substituents, which are the same or different and selected from the group consisting of halogen; OH; $OCH_3$; $OCH_2F$; $OCHF_2$; $OCF_3$; and CN, and wherein $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; and 4 to 5 membered saturated heterocyclyl are optionally substituted with one or more substituents, which are the same or different and selected from the group consisting of halogen; OH; $OCH_3$; $OCH_2F$; $OCHF_2$; $OCF_3$; CN; $CH_3$; $CH_2F$; $CHF_2$; and $CF_3$.

More preferably, $R^1$ is $C_{1-5}$ alkyl; $C_{2-5}$ alkenyl; $C_{2-5}$ alkynyl; $C_{3-5}$ cycloalkyl; $CH_2$-cyclopropyl; $CH_2$-cyclobutyl; or 4 to 5 membered saturated heterocyclyl, wherein $C_{1-5}$ alkyl; $C_{2-5}$ alkenyl; $C_{2-5}$ alkynyl are optionally substituted with one or more substituents, which are the same or different and selected from the group consisting of halogen; OH; $OCH_3$; $OCH_2F$; $OCHF_2$; $OCF_3$; and CN, and wherein $C_{3-5}$ cycloalkyl; $CH_2$-cyclopropyl; $CH_2$-cyclobutyl; and 4 to 5 membered saturated heterocyclyl are optionally substituted with one or more substituents, which are the same or different and selected from the group consisting of halogen; OH; $OCH_3$; $OCH$—$_2F$; $OCHF_2$; $OCF_3$; CN; $CH_3$; $CH_2F$; $CHF_2$; and $CF_3$.

More preferably, $R^1$ is $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; or 4 to 5 membered saturated heterocyclyl, wherein $C_{3-5}$ cycloalkyl; $CH_2$-cyclopropyl; CHF-cyclopropyl; $CF_2$-cyclopropyl; $CH_2$-cyclobutyl; CHF-cyclobutyl; $CF_2$-cyclobutyl; and 4 to 5 membered saturated heterocyclyl are optionally substituted with one or more substituents, which are the same or different and selected from the group consisting of halogen; OH; $OCH_3$; $OCH_2F$; $OCHF_2$; $OCF_3$; CN; $CH_3$; $CH_2F$; $CHF_2$; and $CF_3$.

In a more preferred embodiment $R^1$ is substituted or unsubstituted $C_{1-5}$ alkyl; substituted or unsubstituted $C_{3-5}$ cycloalkyl; substituted or unsubstituted $CH_2$-cyclopropyl; or substituted or unsubstituted $CH_2$-cyclobutyl.

In yet another more preferred embodiment $R^1$ is substituted or unsubstituted $C_{3-5}$ cycloalkyl; substituted or unsubstituted $CH_2$-cyclopropyl; or substituted or unsubstituted $CH_2$-cyclobutyl.

In an even more preferred embodiment $R^1$ is isopropyl; cyclobutyl; ethyl; cyclopropyl; $CH_2$-cyclopropyl; or $CH_2$-cyclobutyl.

In yet another even more preferred embodiment $R^1$ is isopropyl; cyclobutyl; cyclopropyl; $CH_2$-cyclopropyl; or $CH_2$-cyclobutyl.

In an even more preferred embodiment $R^1$ is cyclobutyl; ethyl; or cyclopropyl.

In yet another even more preferred embodiment $R^1$ is cyclobutyl; or cyclopropyl.

Preferably, n is 2.
Preferably, $X^1$ is N.
Preferably, $X^2$ is O;
Preferably, m is 0.
Preferably, n1; n2 are independently selected from the group consisting of 0; and 1. Even more preferably, n1 is 0 and n2 is 0 or 1.

Preferably, $X^3$ is $(CH_2)_{n1}C(O)(CH_2)_{n2}R^2$; $(CH_2)_{n1}C(O)N(R^{1a})(CH_2)_{n2}R^2$; $(CH_2)_{n1}C(O)O(CH_2)_{n2}R^2$; $(CH_2)_{n1}S(O)_2(CH_2)_{n2}R^2$; $(CH_2)_{n1}S(O)_2N(R^{1a})(CH_2)_{n2}R^2$; or $(CH_2)_{n1}N(R^{1a})S(O)_2(CH_2)_{n2}R^2$. More preferably, $X^3$ is $C(O)N(R^{1a})CH_2T$; $C(O)OCH_2T$; $C(O)CH_2T$; $C(O)CH_2OT$; C(O)T; $S(O)_2T$; or $S(O)_2CH_2T$. Even more preferably, $X^3$ is C(O)T; or $C(O)CH_2T$.

Preferably, $R^{1a}$ is H; or $CH_3$.
Preferably, one of $R^2$, $R^3$, $R^4$, $R^{4a}$, $R^{4b}$, $R^5$, $R^6$, $R^{6a}$, $R^{6b}$ is T.

Preferably, $R^2$ is T; or $CH_2OT$.
Preferably, T is phenyl; tetrahydropyranyl; morpholinyl; piperidinyl; pyridinyl; pyrimidinyl; pyrazinyl; pyrazolyl; cyclopropyl; cyclopentyl; cyclohexyl; or tetrahydroisoquinolinyl, wherein T is optionally substituted with one or more $R^7$, which are the same or different.

Preferably, T is unsubstituted or substituted with 1 to 3 $R^7$, which are the same or different and selected from the group consisting of $NO_2$; CN; $C(O)OCH_3$; $OCH_3$; $CH_3$; F; and $T^1$, wherein $T^1$ is unsubstituted or substituted with 1 to 3 $R^{12}$, which are the same or different and selected from the group consisting of $NO_2$; CN; $C(O)OCH_3$; $OCH_3$; $CH_3$; and F.

Compounds of the formula (I) in which some or all of the above-mentioned groups have the preferred or more preferred meanings are also an object of the present invention.

Preferred individual compounds of the present invention are selected from the group consisting of Benzyl 3-[(4-cyclobutyl-1,4-diazepan-1-yl)carbonyl]azetidine-1-carboxylate;
1-cyclobutyl-4-{[1-(piperidin-1-ylcarbonyl)azetidin-3-yl]carbonyl}-1,4-diazepane;
1-cyclobutyl-4-{[1-(morpholin-4-ylcarbonyl)azetidin-3-yl]carbonyl}-1,4-diazepane;
1-cyclobutyl-4-{[1-(cyclohexylcarbonyl)azetidin-3-yl]carbonyl}-1,4-diazepane;
1-cyclobutyl-4-{[1-(tetrahydro-2H-pyran-4-ylcarbonyl)azetidin-3-yl]carbonyl}-1,4-diazepane;
4-({3-[(4-cyclobutyl-1,4-diazepan-1-yl)carbonyl]azetidin-1-yl}carbonyl)benzonitrile;
Methyl 5-({3-[(4-cyclobutyl-1,4-diazepan-1-yl)carbonyl]azetidin-1-yl}carbonyl)pyridine-2-carboxylate;
1-cyclobutyl-4-({1-[(2-methylpyrimidin-5-yl)carbonyl]azetidin-3-yl}carbonyl)-1,4-diazepane;
1-cyclobutyl-4-({1-[(5-methylpyrazin-2-yl)carbonyl]azetidin-3-yl}carbonyl)-1,4-diazepane;
1-cyclobutyl-4-({1-[(6-methylpyridin-3-yl)carbonyl]azetidin-3-yl}carbonyl)-1,4-diazepane;
1-cyclobutyl-4-[(1-{[4-(tetrahydro-2H-pyran-4-yloxy)phenyl]carbonyl}azetidin-3-yl)carbonyl]-1,4-diazepane;
1-cyclobutyl-4-[(1-{[6-(1H-imidazol-1-yl)pyridin-3-yl]carbonyl}azetidin-3-yl)carbonyl]-1,4-diazepane;
1-cyclobutyl-4-[(1-{[6-(1H-1,2,4-triazol-1-yl)pyridin-3-yl]carbonyl}azetidin-3-yl)carbonyl]-1,4-diazepane;
1-cyclobutyl-4-{[1-(1H-pyrazol-1-ylacetyl)azetidin-3-yl]carbonyl}-1,4-diazepane;
1-cyclobutyl-4-{[1-(piperidin-1-ylacetyl)azetidin-3-yl]carbonyl}-1,4-diazepane;
1-cyclobutyl-4-{[1-(morpholin-4-ylacetyl)azetidin-3-yl]carbonyl}-1,4-diazepane;
1-cyclobutyl-4-({1-[(1,1-dioxidothiomorpholin-4-yl)acetyl]azetidin-3-yl}carbonyl)-1,4-diazepane;
1-cyclobutyl-4-({1-[(3,3-difluoropyrrolidin-1-yl)acetyl]azetidin-3-yl}carbonyl)-1,4-diazepane;
1-cyclobutyl-4-({1-[(4,4-difluoropiperidin-1-yl)acetyl]azetidin-3-yl}carbonyl)-1,4-diazepane;
1-cyclobutyl-4-[(1-{[(6-methylpyridin-3-yl)oxy]acetyl}azetidin-3-yl)carbonyl]-1,4-diazepane;
4-(2-{3-[(4-cyclobutyl-1,4-diazepan-1-yl)carbonyl]azetidin-1-yl}-2-oxoethoxy)benzonitrile;
1-cyclobutyl-4-({1-[(4-methoxyphenyl)sulfonyl]azetidin-3-yl}carbonyl)-1,4-diazepane;
1-cyclobutyl-4-{[1-(cyclo hexylsulfonyl)azetidin-3-yl]carbonyl}-1,4-diazepane;
1-cyclobutyl-4-({1-[(cyclopentylmethyl)sulfonyl]azetidin-3-yl}carbonyl)-1,4-diazepane;
1-cyclobutyl-4-{[1-(phenylsulfonyl)azetidin-3-yl]carbonyl}-1,4-diazepane;
4-({3-[(4-cyclobutyl-1,4-diazepan-1-yl)carbonyl]azetidin-1-yl}sulfonyl)benzonitrile;
1-cyclobutyl-4-({1-[(4-methoxycyclohexyl)carbonyl]azetidin-3-yl}carbonyl)-1,4-diazepane;
1-cyclobutyl-4-({1-[(4,4-difluoro cyclo hexyl)carbonyl]azetidin-3-yl}carbonyl)-1,4-diazepane;
1-cyclobutyl-4-[(1-{[4-(3,5-dimethyl-1H-pyrazol-1-yl)phenyl]carbonyl}azetidin-3-yl)carbonyl]-1,4-diazepane;
1-cyclobutyl-4-[(1-{[4-(5-methyl-1,3,4-oxadiazol-2-yl)phenyl]carbonyl}azetidin-3-yl)carbonyl]-1,4-diazepane;
1-cyclobutyl-4-{[1-(cyclopropylacetyl)azetidin-3-yl]carbonyl}-1,4-diazepane;
1-cyclobutyl-4-{[1-(cyclohexylacetyl)azetidin-3-yl]carbonyl}-1,4-diazepane;
4-(2-{3-[(4-cyclobutyl-1,4-diazepan-1-yl)carbonyl]azetidin-1-yl}-2-oxoethyl)benzonitrile;
1-cyclobutyl-4-[(1-{[4-(1,3-thiazol-2-yl)phenyl]carbonyl}azetidin-3-yl)carbonyl]-1,4-diazepane;
1-cyclobutyl-4-[(1-{[4-(2-methyl-1,3-thiazol-4-yl)phenyl]carbonyl}azetidin-3-yl)carbonyl]-1,4-diazepane;
1-cyclobutyl-4-[(1-{[4-(5-methyl-1,2,4-oxadiazol-3-yl)phenyl]carbonyl}azetidin-3-yl)carbonyl]-1,4-diazepane;
1-cyclobutyl-4-[(1-{[4-(1-methylethyl)phenyl]carbonyl}azetidin-3-yl)carbonyl]-1,4-diazepane;
1-cyclobutyl-4-({1-[(4-phenoxyphenyl)carbonyl]azetidin-3-yl}carbonyl)-1,4-diazepane;
1-cyclobutyl-4-[(1-{[4-(1H-pyrazol-1-yl)phenyl]carbonyl}azetidin-3-yl)carbonyl]-1,4-diazepane;
1-cyclobutyl-4-[(1-{[4-(3-methyl-1,2,4-oxadiazol-5-yl)phenyl]carbonyl}azetidin-3-yl)carbonyl]-1,4-diazepane;
1-cyclobutyl-4-[(1-{[4-(4,4-dimethyl-4,5-dihydro-1,3-oxazol-2-yl)phenyl]carbonyl}azetidin-3-yl)carbonyl]-1,4-diazepane;
1-cyclobutyl-4-({1-[(6-methylpyridin-3-yl)acetyl]azetidin-3-yl}carbonyl)-1,4-diazepane;
1-cyclobutyl-4-({1-[(4-pyridin-3-ylphenyl)carbonyl]azetidin-3-yl}carbonyl)-1,4-diazepane;
1-cyclobutyl-4-({1-[(4-pyridin-4-ylphenyl)carbonyl]azetidin-3-yl}carbonyl)-1,4-diazepane;
1-cyclobutyl-4-[(1-{[3-(2-methyl-1,3-thiazol-4-yl)phenyl]carbonyl}azetidin-3-yl)carbonyl]-1,4-diazepane;
2-({3-[(4-cyclobutyl-1,4-diazepan-1-yl)carbonyl]azetidin-1-yl}carbonyl)-1H-benzimidazole;
5-({3-[(4-cyclobutyl-1,4-diazepan-1-yl)carbonyl]azetidin-1-yl}carbonyl)-1-methyl-1H-benzimidazole;
5-({3-[(4-cyclobutyl-1,4-diazepan-1-yl)carbonyl]azetidin-1-yl}carbonyl)-1-methyl-1H-benzotriazole;
7-({3-[(4-cyclobutyl-1,4-diazepan-1-yl)carbonyl]azetidin-1-yl}carbonyl)imidazo[1,2-α]pyridine;
1-cyclobutyl-4-{[1-(1H-1,2,4-triazol-3-ylcarbonyl)azetidin-3-yl]carbonyl}-1,4-diazepane;
1-cyclobutyl-4-({1-[(1-methyl-1H-pyrazol-4-yl)carbonyl]azetidin-3-yl}carbonyl)-1,4-diazepane;
1-cyclobutyl-4-{[1-(tetrahydro-2H-pyran-4-ylacetyl)azetidin-3-yl]carbonyl}-1,4-diazepane;
1-({1-[(4-chlorophenyl)acetyl]azetidin-3-yl}carbonyl)-4-cyclobutyl-1,4-diazepane;
1-cyclobutyl-4-[(1-{[4-(methylsulfonyl)phenyl]carbonyl}azetidin-3-yl)carbonyl]-1,4-diazepane;
3-[(4-cyclobutyl-1,4-diazepan-1-yl)carbonyl]-N-(cyclohexylmethyl)azetidine-1-carboxamide;
3-[(4-cyclobutyl-1,4-diazepan-1-yl)carbonyl]-N-(tetrahydro-2H-pyran-4-ylmethyl)azetidine-1-carboxamide;
3-[(4-cyclobutyl-1,4-diazepan-1-yl)carbonyl]-N-(4-fluorobenzyl)azetidine-1-carboxamide;
N-(4-cyanophenyl)-3-[(4-cyclobutyl-1,4-diazepan-1-yl)carbonyl]azetidine-1-carboxamide;
3-[(4-cyclobutyl-1,4-diazepan-1-yl)carbonyl]-N-(cyclohexylmethyl)-N-methylazetidine-1-carboxamide;
3-[(4-cyclobutyl-1,4-diazepan-1-yl)carbonyl]-N-methyl-N-(tetrahydro-2H-pyran-4-ylmethyl)azetidine-1-carboxamide;
3-[(4-cyclobutyl-1,4-diazepan-1-yl)carbonyl]-N-(4-fluorobenzyl)-N-methylazetidine-1-carboxamide;
3-[(4-cyclobutyl-1,4-diazepan-1-yl)carbonyl]-N-(4-fluorobenzyl)-N-methylazetidine-1-carboxamide;
N-(4-cyanobenzyl)-3-[(4-cyclobutyl-1,4-diazepan-1-yl)carbonyl]-N-methylazetidine-1-carboxamide;

4-nitrophenyl 3-[(4-cyclobutyl-1,4-diazepan-1-yl)carbonyl]
  azetidine-1-carboxylate;
2-({3-[(4-cyclobutyl-1,4-diazepan-1-yl)carbonyl]azetidin-
  1-yl}carbonyl)-1,2,3,4-tetrahydroisoquinoline;
N-(4-cyanobenzyl)-3-[(4-cyclobutyl-1,4-diazepan-1-yl)car-
  bonyl]azetidine-1-carboxamide;
4-chlorophenyl 3-[(4-cyclobutyl-1,4-diazepan-1-yl)carbo-
  nyl]azetidine-1-carboxylate;
6-methylpyridin-3-yl 3-[(4-cyclobutyl-1,4-diazepan-1-yl)
  carbonyl]azetidine-1-carboxylate;
4-cyanophenyl 3-[(4-cyclobutyl-1,4-diazepan-1-yl)carbo-
  nyl]azetidine-1-carboxylate;
1-[(1-acetylazetidin-3-yl)carbonyl]-4-cyclobutyl-1,4-diaz-
  epane;
1-cyclobutyl-4-[(1-propanoylazetidin-3-yl)carbonyl]-1,4-
  diazepane;
1-cyclobutyl-4-[(1-{[4-(1H-imidazol-1-yl)phenyl]
  carbonyl}azetidin-3-yl)carbonyl]-1,4-diazepane;
1-cyclobutyl-4-[(1-{[4-(1H-1,2,4-triazol-1-yl)phenyl]
  carbonyl}azetidin-3-yl)carbonyl]-1,4-diazepane;
1-cyclobutyl-4-[(1-{[4-(1H-1,2,4-triazol-1-ylmethyl)phe-
  nyl]carbonyl}azetidin-3-yl)carbonyl]-1,4-diazepane;
1-cyclobutyl-4-({1-[(2-methylpyridin-4-yl)carbonyl]azeti-
  din-3-yl}carbonyl)-1,4-diazepane;
2-[5-({3-[(4-cyclobutyl-1,4-diazepan-1-yl)carbonyl]azeti-
  din-1-yl}carbonyl)pyridin-2-yl]propan-2-ol;
5-({3-[(4-cyclobutyl-1,4-diazepan-1-yl)carbonyl]azetidin-
  1-yl}carbonyl)-N-methylpyridine-2-carboxamide;
1-cyclobutyl-4-[(1-{[3-fluoro-4-(1H-1,2,4-triazol-1-yl)phe-
  nyl]carbonyl}azetidin-3-yl)carbonyl]-1,4-diazepane;
1-(1-methylethyl)-4-({1-[(6-methylpyridin-3-yl)carbonyl]
  azetidin-3-yl}carbonyl)-1,4-diazepane;
1-ethyl-4-({1-[(6-methylpyridin-3-yl)carbonyl]azetidin-3-
  yl}carbonyl)-1,4-diazepane;
1-cyclopentyl-4-({1-[(6-methylpyridin-3-yl)carbonyl]azeti-
  din-3-yl}carbonyl)-1,4-diazepane;
1-cyclohexyl-4-({1-[(6-methylpyridin-3-yl)carbonyl]azeti-
  din-3-yl}carbonyl)-1,4-diazepane;
1-(cyclopropylmethyl)-4-({1-[(6-methylpyridin-3-yl)carbo-
  nyl]azetidin-3-yl}carbonyl)-1,4-diazepane;
1-(2-methylpropyl)-4-({1-[(6-methylpyridin-3-yl)carbonyl]
  azetidin-3-yl}carbonyl)-1,4-diazepane;
1-methyl-4-({1-[(6-methylpyridin-3-yl)carbonyl]azetidin-3-
  yl}carbonyl)-1,4-diazepane;
2-({3-[(4-cyclobutyl-1,4-diazepan-1-yl)carbonyl]azetidin-
  1-yl}carbonyl)-1-methyl-1H-benzimidazole; and
1-cyclobutyl-4-({1-[(6-methylpyridin-3-yl)carbonyl]azeti-
  din-3-yl}carbonyl)piperazine.

Prodrugs of the compounds of the invention are also within the scope of the present invention. "Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

Where tautomerism, like e.g. keto-enol tautomerism, of compounds of formula (I) may occur, the individual forms, like e.g. the keto and enol form, are comprised separately and together as mixtures in any ratio. Same applies for stereoisomers, like e.g. enantiomers, cis/trans isomers, conformers and the like.

Especially, when enantiomeric or diastereomeric forms are given in a compound according to formula (I) each pure form separately and any mixture of at least two of the pure forms in any ratio is comprised by formula (I) and is a subject of the present invention.

Isotopic labeled compounds of formula (I) are also within the scope of the present invention. Methods for isotope labeling are known in the art. Preferred isotopes are those of the elements H, C, N, O and S.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials, reagents and/or catalysts.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The present invention provides compounds of general formula (I) as Histamine H3 receptor antagonists.

As described before, the histamine H3 receptor is a G protein-coupled receptor (GPCR) and one out of four receptors of the histamine receptor family. Histamine receptors have long been attractive drug targets, mirrored in the development of antihistamines, which were directed at the histamine H1 receptor for the treatment of allergic reactions or at the histamine H2 receptor to ameliorate gastric ulcers by inhibiting gastric acid secretion. The H3 receptor has been identified as a presynaptic autoreceptor, regulating the release of histamine (Arrang et al. (1983) Nature: 302; 832-837), as well as a heteroreceptor that regulates the release of many other important neurotransmitters (acetylcholine, norepinephrine, dopamine, and serotonin). Structurally divergent H3 receptor antagonists/inverse agonists have been developed and shown to comprise activity in a variety of cognition tests in mice and rat (e.g. Esbenshade et al. (2006) Mol Interventions: 6 (2); 77-88) as well as in models for sleeping disorders and energy balance. From these studies it is concluded that such antagonists comprise a potential treatment for a variety of disorders affecting cognition (e.g., Alzheimer's disease, Parkinson's disease, Attention Deficit and Hyperactivity Disorder, Schizophrenia, Foetal Alcohol Syndrome, Mild Cognitive Impairment, Age-related Memory Dysfunction, Down Syndrome and others), as well as sleep (e.g., hypersomnia and narcolepsy), and energy homeostasis (e.g. obesity) (Witkin & Nelson (2004) JPET:103; 1-20; Hancock & Brune (2005) Exp Opin Inves Drugs:14 (3), 223-241).

The pharmacology of the H3 receptor seems not only to be determined by its localization but appears also to be regulated by differential splicing. Today more than 20 splice variants (isoforms) have been described but their functions have yet to be elucidated completely (Bongers et al. (2007) Biochem Pharm: 73; 1195-1204). The H3 receptor is localized primarily to the central nervous system (CNS), with highest expression, in rodents, in the cerebral cortex, hippocampal formations, striatum, and hypothalamus (Drutel et al. (2001) Mol Pharmacol: 59; 1-8). Similarly in human, H3 receptor expression is prominent in the basal ganglia, globus pallidus, hippocampus, and cortex (Martinez-Mir et al. (1990) Brain Res: 526; 322 327). Notably, many of these brain regions are critical for cognition (cortex and hippocampus) and sleep and homeostatic regulation (hypothalamus). The H3 receptor has been shown also to localize to regions which might be involved in pain sensation or transmission and therefore might offer treatment opportunities for different pain states (Cannon et al. (2007) Pain: 129; 76-92).

In addition to agonist-induced signaling, the H3 receptor is constitutively active and capable of signaling independently of agonist both in vitro and in vivo (Morisset et al. (2000) Nature: 408, 860-864).

All these considerations suggest that novel H3 receptor antagonists like the series in this application could be useful in the treatment of cognitive dysfunctions as well as sleeping and energy homeostasis disorders. The term "antagonist" also includes inverse agonists.

Based on the information above and further literature, like WO-A 2007/080140 and WO-A 2006/136924 the following diseases and disorders are preferably affected.
Neurological Disorders:
Major conditions include
  behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders);
  seizure disorders;
  neurodegenerative disorders (e.g. Alzheimer's disease, Parkinson's disease, Multiple Sclerosis);
  sleep disorders (e.g. hypersomnia and narcolepsy, excessive daytime sleepiness, diurnal and seasonal variations in sleep patterns);
  Migraine;
  Fatigue;
  Stroke;
  tremor.

Disorders affecting energy homeostasis as well as complications associated therewith, e.g. obesity, eating disorders associated with excessive food intake, bulima, binge eating, complications associated therewith e.g. diabetes mellitus.

Pain, e.g. neuropathic pain, inflammatory pain, nociception.

Cardiovascular disorders, e.g. acute myocardial infarction, and other disorders, i.e. gastrointestinal disorders, vestibular dysfunction (e.g. Morbus Meniere, dizziness caused by drug abuse, motion sickness), drug abuse, nasal congestion, allergic rhinitis (hay fever), asthma.

Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma.

More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma.

Even more preferred disorders are Alzheimer's disease, Parkinson's disease, Attention Deficit and Hyperactivity Disorder, schizophrenia, idiopathic hypersomnia, narcolepsy, obesity, neuropathic pain.

Preferably, the compounds of the present invention may be used for fatigue and cognitive impairment/dysfunction associated with Multiple Sclerosis. Accordingly, Multiple Sclerosis is a more preferred disease or disorder for disease related fatigue and cognitive impairment/dysfunction.

Accordingly, one aspect of the present invention is a compound or a pharmaceutically acceptable salt thereof of the present invention for use as a medicament.

Yet another aspect of the present invention is a compound or a pharmaceutically acceptable salt thereof of the present invention for use in a method of treating or preventing diseases and disorders associated with the H3 receptor.

Yet another aspect of the present invention is a compound or a pharmaceutically acceptable salt thereof of the present invention for use in a method of treating or preventing neurological disorders, e.g. behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders), seizure disorders, neurodegenerative disorders (e.g. Alzheimer's disease, Parkinson's disease, Multiple Sclerosis), sleep disorders (e.g. hypersomnia and narcolepsy, excessive daytime sleepiness, diurnal and seasonal variations in sleep patterns), Migraine, Fatigue, Stroke, tremor; disorders affecting energy homeostasis as well as complications associated therewith, e.g. obesity, eating disorders associated with excessive food intake, bulima, binge eating, complications associated therewith e.g. diabetes mellitus; pain, e.g. neuropathic pain, inflammatory pain, nociception; cardiovascular disorders, e.g. acute myocardial infarction; gastrointestinal disorders; vestibular dysfunction (e.g. Morbus Meniere, dizziness caused by drug abuse, motion sickness); drug abuse; nasal congestion; allergic rhinitis (hay fever); or asthma. Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma. More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma. Even more preferred disorders are Alzheimer's disease, Parkinson's disease, Attention Deficit and Hyperactivity Disorder, schizophrenia, idiopathic hypersomnia, narcolepsy, obesity, neuropathic pain.

Yet another aspect of the present invention is the use of a compound or a pharmaceutically acceptable salt thereof of the present invention for the manufacture of a medicament for the treatment or prophylaxis of diseases and disorders associated with the H3 receptor.

Yet another aspect of the present invention is the use of a compound or a pharmaceutically acceptable salt thereof of the present invention for the manufacture of a medicament for the treatment or prophylaxis of neurological disorders, e.g. behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders), seizure disorders, neurodegenerative disorders (e.g. Alzheimer's disease, Parkinson's disease, Multiple Sclerosis), sleep disorders (e.g. hypersomnia and narcolepsy, excessive daytime sleepiness, diurnal and seasonal variations in sleep patterns), Migraine, Fatigue, Stroke, tremor; disorders affecting energy homeostasis as well as complications associated therewith, e.g. obesity, eating disorders associated with excessive food intake, bulima, binge eating, complications associated therewith e.g. diabetes mellitus; pain, e.g. neuropathic pain, inflammatory pain, nociception; cardiovascular disorders, e.g. acute myocardial infarction; gastrointestinal disorders; vestibular dysfunction (e.g. Morbus Meniere, dizziness caused by drug abuse, motion sickness); drug abuse; nasal congestion; allergic rhinitis (hay fever); or asthma. Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma. More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma. Even more preferred disorders are Alzheimer's disease, Parkinson's disease, Attention Deficit and Hyperactivity Disorder, schizophrenia, idiopathic hypersomnia, narcolepsy, obesity, neuropathic pain.

Yet another aspect of the present invention is a method for treating, controlling, delaying or preventing in a mammalian patient in need of the treatment of one or more conditions selected from the group consisting of diseases and disorders associated with the H3 receptor, wherein the method comprises the administration to said patient a therapeutically effective amount of a compound of the present invention or a pharmaceutically acceptable salt thereof.

Yet another aspect of the present invention is a method for treating, controlling, delaying or preventing in a mammalian patient in need of the treatment of one or more conditions selected from the group consisting of neurological disorders, e.g. behavioral/cognitive syndromes (e.g. Alzheimer's disease, Parkinson's disease, Attention Deficit and Hyperactivity Disorder, schizophrenia, Foetal Alcohol Syndrome, Mild Cognitive Impairment, Age-related Memory Dysfunction, Down Syndrome, epilepsy, convulsion, depression, anxiety disorders), seizure disorders, neurodegenerative disorders (e.g. Alzheimer's disease, Parkinson's disease, Multiple Sclerosis), sleep disorders (e.g. hypersomnia and narcolepsy, excessive daytime sleepiness, diurnal and seasonal variations in sleep patterns), Migraine, Fatigue, Stroke, tremor; disorders affecting energy homeostasis as well as complications associated therewith, e.g. obesity, eating disorders associated with excessive food intake, bulima, binge eating, complications associated therewith e.g. diabetes mellitus; pain, e.g. neuropathic pain, inflammatory pain, nociception; cardiovascular disorders, e.g. acute myocardial infarction; gastrointestinal disorders; vestibular dysfunction (e.g. Morbus Meniere, dizziness caused by drug abuse, motion sickness); drug abuse; nasal congestion; allergic rhinitis (hay fever); and asthma, wherein the method comprises the administration to said patient a therapeutically effective amount of a compound of the present invention or a pharmaceutically acceptable salt thereof. Preferred disorders are Alzheimer's disease, Parkinson's disease, Attention Deficit and Hyperactivity Disorder, schizophrenia, Foetal Alcohol Syndrome, Mild Cognitive Impairment, Age-related Memory Dysfunction, disease-related cognitive dysfunctions, Lewy body dementia, vascular dementia, Down Syndrome, epilepsy, convulsion, depression, anxiety disorders, idiopathic hypersomnia, narcolepsy, shift-work sleep disorder, disease-related fatigue, chronic fatigue syndrome, Migraine Stroke, tremor, obesity, eating disorders, diabetes mellitus, neuropathic pain, inflammatory pain, acute myocardial infarction, gastrointestinal disorders, vestibular dysfunction (e.g. Morbus Meniere), motion sickness, drug abuse, nasal congestion, allergic rhinitis (hay fever), asthma. More preferred disorders are Alzheimer's disease, Parkinson's disease, Attention Deficit and Hyperactivity Disorder, schizophrenia, Mild Cognitive Impairment, disease-related cognitive dysfunctions, Lewy body dementia, vascular dementia, idiopathic hypersomnia, narcolepsy, obesity, diabetes mellitus, neuropathic pain, nasal congestion, allergic rhinitis (hay fever), asthma. Even more preferred disorders are Alzheimer's disease, Parkinson's disease, Attention Deficit and Hyperactivity Disorder, schizophrenia, idiopathic hypersomnia, narcolepsy, obesity, neuropathic pain.

Yet another aspect of the present invention is a pharmaceutical composition comprising at least one compound or a pharmaceutically acceptable salt thereof of the present invention together with a pharmaceutically acceptable carrier, optionally in combination with one or more other bioactive compounds or pharmaceutical compositions.

Preferably, the one or more bioactive compounds are lipase inhibitors, anorectic agents, selective serotonin uptake inhibitors, neurotransmitter reuptake blocker, dopamine replacement agents, agents that stimulate metabolism of body fat, anti-diabetic agents, lipid lowering agents, anti-stroke agents or histamine H1 receptor antagonists. A combination of one or more histamine H3 receptor antagonists of the present invention and histamine H1 receptor antagonists is preferred, especially for the treatment of allergic rhinitis, allergic congestion or nasal congestion.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may comprise one or more additional compounds as active ingredients like one or more compounds of formula (I) not being the first compound in the composition or other Histamine H3 receptor antagonists.

The active ingredients may be comprised in one or more different pharmaceutical compositions (combination of pharmaceutical compositions).

The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) may be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

Starting materials for the synthesis of preferred embodiments of the invention may be purchased from commercially available sources such as Array, Sigma Aldrich, Acros, Fisher, Fluka, ABCR or can be synthesized using known methods by one skilled in the art.

In general, several methods are applicable to prepare compounds of the present invention. In some cases various strategies can be combined. Sequential or convergent routes may be used. The following routes should be understood as examples. It is clear for a practitioner in the art to combine such routes optionally in combination with standard methods and reagents, like activation of functional groups or protection of functional groups.

One exemplary method for the preparation of a compound of the present invention, wherein in formula (I) $X^1$ is N; $X^2$ is O; $X^4$ is C(O), comprises the steps of (a) protecting the amino group of a compound of formula (II) by reacting the amino group with a suitable chloroformate (such as benzyl chlorocarbonate) or di-tert-butyl dicarbonate

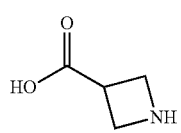
(II)

(b) reacting the carboxylic acid group of the resulting carbamate compound from step (a) with amide coupling reagents (such as HOBt and HBTU or HOBt and EDCI) or alternatively forming the acid chloride using a reagent such as $SOCl_2$) and reacting the resulting activated ester or acid chloride with a compound of formula (III)

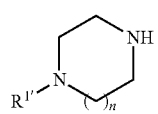
(III)

wherein n has the meaning as indicated above and $R^{1'}$ is $R^1$ as indicated above or as suitable N-atom protecting group to yield a compound of formula (I), optionally after removal of the protecting group $R^{1'}$ and reacting the liberated amino group with a compound of formula $R^1$=O, wherein the oxo group is attached to a carbon atom of $R^1$, followed by reduction of the resulting imine; or alternatively, reacting the liberated amino group with a compound of formula $R^1$-halide (optionally in the presence of a base) and (c) deprotecting the azetidine amino group of the resulting compound from step (b) by hydrogenation (using conditions such as Pd—C and hydrogen gas) or transfer hydrogenation (using conditions such as ammonium formate and Pd—C) or strong acid (such as 4M HCl or TFA) to form a compound represented by formula (IV)

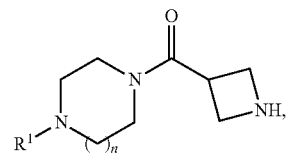
(IV)

wherein n and $R^1$ have the meaning as indicated above;

(d) reacting the resulting secondary amino group from step (c) with an acid chloride of formula $ClC(O)(CH_2)_{n2}R^2$ in the presence of a suitable base (such as DIPEA or pyridine) at a temperature usually between 0° C. and 85° C., to yield a compound of formula (I), wherein n2, $R^2$ are defined as indicated above.

In a further embodiment of the above method, the azetidine amino group of a compound resulting from step (b) can be selectively deprotected in the presence of an orthogonal protecting group $R^{1'}$ by (e) hydrogenation (using conditions such as Pd—C and hydrogen gas) or transfer hydrogenation (using conditions such as ammonium formate and Pd—C) or strong acid (such as 4M HCl or TFA) to form a compound represented by formula (IVa); and

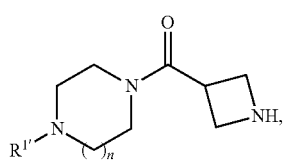
(IVa)

(f) reacting the resulting azetidine amino group from step (e) with an acid chloride of formula $ClC(O)(CH_2)_{n2}R^2$ in the presence of a suitable base (such as DIPEA or pyridine) usually between 0° C. and 85° C., wherein n2, $R^2$ are defined as indicated above; and (g) removal of the amino protecting group the $R^{1'}$ of the resulting compound from step (f) by hydrogenation (using conditions such as Pd—C and hydrogen gas) or transfer hydrogenation (using conditions such as ammonium formate and Pd—C) or strong acid (such as 4M HCl or TFA); and (h) reacting the liberated amino group with a compound of formula $R^1$=O, wherein the oxo group is attached to a carbon atom of $R^1$, followed by reduction of the resulting imine to yield a compound of formula (I); or alternatively, reacting the liberated amino group with a compound of formula $R^1$-halide (optionally in the presence of base) to yield a compound of formula (I).

Accordingly another aspect of the present invention is a method for the preparation of a compound of the present invention, wherein in formula (I) $X^1$ is N; $X^2$ is O, n1 is 0, $X^4$ is C(O), comprising the steps of (a) protecting the amino group of a compound of formula (IIa) by reacting the amino group with a suitable chloroformate (such as benzyl chlorocarbonate) or di-tert-butyl dicarbonate

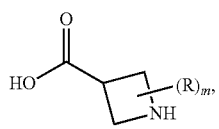

(IIa)

wherein R, m have the meaning as indicated above;

(b) reacting the carboxylic acid group of the resulting carbamate compound from step (a) with a compound of formula (III)—or optionally firstly reacting with amide coupling reagents (such as HOBt and HBTU or HOBt and EDCI) or alternatively forming the acid chloride using a reagent such as $SOCl_2$) and secondly reacting the resulting activated ester or acid chloride with a compound of formula (III)—

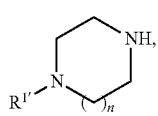

(III)

wherein n has the meaning as indicated above and $R^{1'}$ is $R^1$ as indicated above or as suitable N-atom protecting group using standard amide coupling conditions and reagents to yield a compound of formula (I), optionally after removal of the protecting group and reacting the liberated amino group with a compound of formula $R^1$=O, wherein the oxo group is attached to a carbon atom of $R^1$, followed by reduction of the resulting imine; or alternatively, reacting the liberated amino group with a compound of formula $R^1$-halide (optionally in the presence of base) and (c) deprotecting the azetidine amino group of the resulting compound from step (b) to form a compound represented by formula (IVb)

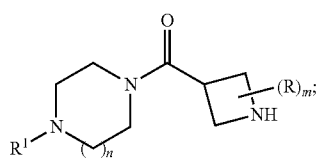

(IVb)

(d) reacting the resulting secondary amino group from step (c) with an acid chloride of formula $ClC(O)(CH_2)_{n2}R^2$ in the presence of a suitable base to yield a compound of formula (I), wherein n2, $R^2$ are defined as indicated above.

Alternatively, compounds of formula (I), wherein $X^1$ is N and $X^2$ is S, may be prepared by a method comprising the steps of (c') reacting amide group of the product formed from step (b) with Lawesson's reagent (usually between room temperature and 100° C.)

(d') deprotecting the azetidine amino group of the resulting compound from step (c') by hydrogenation (using conditions such as Pd—C and hydrogen gas) or transfer hydrogenation (using conditions such as ammonium formate and Pd—C) to form a compound represented by formula (V)

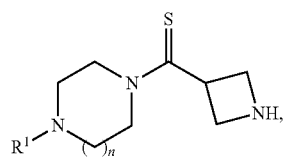

(V)

wherein n and $R^1$ have the meaning as indicated above;

(e') reacting the resulting secondary amino group from step (d') with an acid chloride of formula $ClC(O)(CH_2)_{n2}R^2$ in the presence of a suitable base (such as DIPEA or pyridine) and at a temperature usually between 0° C. and 85° C., to yield a compound of formula (I), wherein n2, $R^2$ are defined as above.

Alternatively, compounds of formula (I) wherein $X^1$ is N and $X^2$ is N—CN, may be prepared by a method comprising the steps of (a) reacting cyanamide with carbon disulfide and then treating the resulting intermediate with dimethyl sulphate to form a compound of formula (VI)

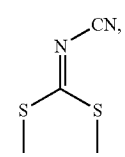

(VI)

(b) reacting the amino group of compound of formula (III) with a compound of formula (VI) (usually between room temperature and 80° C.);

(c) reacting the compound from step (b) with a compound of formula (VII) at elevated temperature (up to 100° C.), wherein $X^2$=N—CN and $X^{3'}$ is a suitable nitrogen protecting group (such as Boc or Cbz)

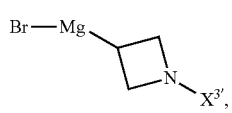

(VII)

(d) removal of the $X^{3'}$ nitrogen protecting group of the resulting compound from step (c) using strong acid (such as 4M HCl or TFA) when $X^{3'}$ is Boc, or by hydrogenation (using conditions such as Pd—C and hydrogen gas) or transfer hydrogenation (using conditions such as ammonium formate and Pd—C) when $X^{3'}$ is Cbz, to form a compound represented by formula (VIII)

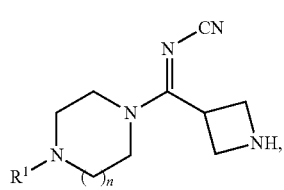

(VIII)

(e) reacting the resulting secondary amino group from step (d) with an acid chloride of formula $ClC(O)(CH_2)_{n2}R^2$ in the presence of a suitable base (such as DIPEA or pyridine) and at a temperature usually between 0° C. and 85° C., to yield a compound of formula (I), wherein n2, $R^2$ are defined as indicated above.

Alternatively, compounds of general formula (I), wherein $X^2$ is N—$OC_{1-4}$ alkyl and $X^{3'}$ is Cbz, may be prepared from a compound of formula (Ib) by a method comprising the steps of

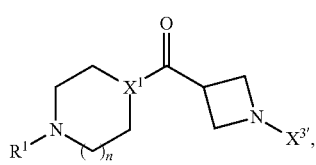
(Ib)

(a) reaction with oxalyl chloride followed by reaction with a compound of formula $NH_2$—$OC_{1-4}$ alkyl (b) deprotecting the azetidine amino group of the resulting compound from step (a) by hydrogenation (using conditions such as Pd—C and hydrogen gas) or transfer hydrogenation (using conditions such as ammonium formate and Pd—C), to form a compound represented by formula (IX)

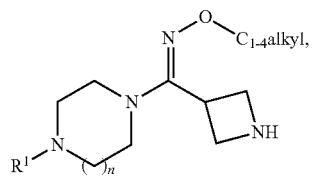
(IX)

(c) reacting the resulting secondary amino group from step (b) with an acid chloride of formula $ClC(O)(CH_2)_{n2}R^2$ in the presence of a suitable base (such as DIPEA or pyridine) and at a temperature usually between 0° C. and 85° C., to yield a compound of formula (I), wherein n2, $R^2$ are defined as indicated above.

Alternatively, compounds of general formula (I) wherein $X^1$ is CH and n is 1, may be prepared from a compound of formula (X) by a method comprising the steps of

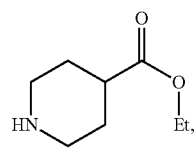
(X)

(a) reacting the amino group with a compound of formula $R^1$=O, wherein the oxo group is attached to a carbon atom of $R^1$, followed by reduction of the resulting imine;

(b) saponification of the ester group with base such as LiOH;

(c) reacting the carboxylic acid group from step (b) with a chlorinating agent (such as thionyl chloride or oxalyl chloride, optionally in the presence of catalytic DMF) and reacting the resulting acid chloride with a compound of formula (XI)

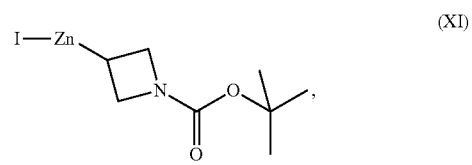
(XI)

wherein the compound of formula (XI) can be formed by treating commercially available tert-butyl 3-iodoazetidine-1-carboxylate with zinc;

(d) deprotecting the azetidine amino group of the resulting compound from step (c) with strong acid (such as 4M HCl or TFA), to form a compound represented by formula (XII)

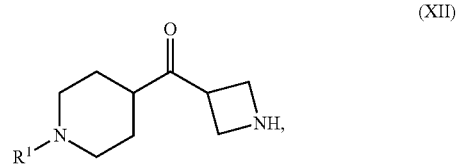
(XII)

(e) reacting the resulting secondary amino group from step (d) with an acid chloride of formula $ClC(O)(CH_2)_{n2}R^2$ in the presence of a suitable base (such as DIPEA or pyridine) and at a temperature usually between 0° C. and 85° C., to yield a compound of formula (I) wherein n2, $R^2$ are defined as indicated above.

Alternatively, compounds of general formula (I) wherein $X^1$ is CH and n is 2, may be prepared from a compound of formula (XIII) by a method comprising the steps of

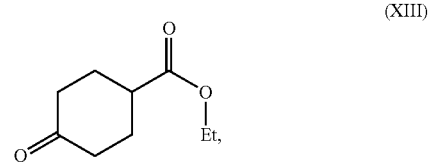
(XIII)

(a) reacting the ketone group with sodium azide and $MeSO_3H$ at between RT and 80° C., followed by reduction of the resulting lactam and ester with LAH (usually between RT and 80° C.);

(b) reacting the amino group with a compound of formula $R^1$=O, wherein the oxo group is attached to a carbon atom of $R^1$, followed by reduction of the resulting imine;

(c) oxidation of the primary alcohol to the carboxylic acid with chromic acid (Jones oxidation);

(d) reacting the carboxylic acid group from step (c) with a chlorinating agent (such as thionyl chloride or oxalyl chloride, optionally in the presence of catalytic DMF) and reacting the resulting acid chloride with a compound of formula (XI);

(e) deprotecting the azetidine amino group of the resulting compound from step (d) with strong acid (such as 4M HCl or TFA), to form a compound represented by formula (XIV)

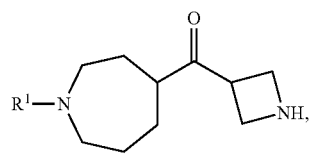

(XIV)

(f) reacting the resulting secondary amino group from step (e) with an acid chloride of formula ClC(O)(CH$_2$)$_{n2}$R$^2$ in the presence of a suitable base (such as DIPEA or pyridine) and at a temperature usually between 0° C. and 85° C., to yield a compound of formula (I) wherein n2, R$^2$ are defined as indicated above.

Alternatively, compounds of general formula (I) wherein X$^1$ is CH and n is 2, may be prepared from a compound of formula (XIIIa) where R$^{1'}$ is a suitable protecting group (such as Cbz or Boc) by a method comprising the steps of

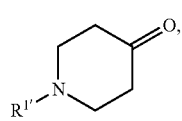

(XIIIa)

(a) reacting the ketone group with an alkyl diazoacetate (such as ethyl diazoacetate) in the presence of a Lewis acid (such as boron trifluoride diethyl etherate) usually between −80° C. and RT;
(b) eliminating the resulting alcohol to give an α,β-unsaturated ester by acid catalysed elimination (alternatively the alcohol can be converted into a halide (such as bromide using a reagent such as PBr$_3$) or sulfonate (such as a mesylate via reaction with MsCl and TEA) and eliminated in the presence of a base (such as DBU) usually between RT and 100° C.);
(c) removal of the alkene via hydrogenation (usually using hydrogen gas or ammonium formatate in the presence of a source of palladium such as Pd/C);
(d) removal of the protecting group R$^{1'}$ (using H$_2$/Pd/C for a cbz protecting group) and reacting the amino group with a compound of formula R$^1$=O, wherein the oxo group is attached to a carbon atom of R$^1$, followed by reduction of the resulting imine;
(e) hydrolysis of the ester to give the carboxylic acid using aqueous base such as LiOH or acid such as HCl and reacting the carboxylic acid group with a chlorinating agent (such as thionyl chloride or oxalyl chloride, optionally in the presence of catalytic DMF) and reacting the resulting acid chloride with a compound of formula (XI);
(f) deprotecting the azetidine amino group of the resulting compound from step (d) with strong acid (such as 4M HCl or TFA), to form a compound represented by formula (XIV);
(g) reacting the resulting secondary amino group from step (f) with an acid chloride of formula ClC(O)(CH$_2$)$_{n2}$R$^2$ in the presence of a suitable base (such as DIPEA or pyridine) and at a temperature usually between 0° C. and 85° C., to yield a compound of formula (I) wherein n2, R$^2$ are defined as indicated above.

The method may comprise further steps where independently compounds of formulae (IV), (IVb), (V), (VIII), (IX), (XII) or (XIV), wherein the meanings are as indicated above, are further modified by reacting the secondary amino group with either of;

(i) a compound of formula HOC(O)(CH$_2$)$_{n2}$R$^2$ that is first converted to the relevant activated ester by reaction with amide coupling reagents (such as EDCl/HOBt or HBTU/HOBt in the presence of a base such as DIPEA) to yield a compound of formula (I), wherein n1=0 and X$^4$ is C(O);
(ii) a compound of formula R$^2$(CH$_2$)$_{n2}$C(O)OC(O)(CH$_2$)$_{n2}$R$^2$ in the presence of a base such as DIPEA to yield a compound of formula (I), wherein n1=0 and X$^4$ is C(O);
(iii) a compound of formula R$^2$(CH$_2$)$_{n2}$NCO to yield a compound of formula (I), wherein n1=0 and X$^4$ is C(O)NH;
(iv) a compound of formula R$^2$(CH$_2$)$_{n2}$S(O)$_2$(CH$_2$)$_{n1}$-halide in the presence of a base such as DIPEA to yield a compound of formula (I), wherein n1=0 to 2 and X$^4$ is S(O)$_2$;
(v) a compound of formula R$^2$(CH$_2$)$_{n2}$(R$^{1a}$)NC(O)(CH$_2$)$_{n1}$-halide in the presence of a base such as DIPEA to yield a compound of formula (I), wherein n1=0 to 2 and X$^4$ is C(O)N(R$^{1a}$);
(vi) a compound of formula R$^2$(CH$_2$)$_{n2}$OC(O)(CH$_2$)$_{n1}$-halide in the presence of a base such as DIPEA to yield a compound of formula (I), wherein n1=0 to 2 and X$^4$ is C(O)O;
(vii) a compound of formula R$^2$(CH$_2$)$_{n2}$(R$^{1a}$)NS(O)$_2$(CH$_2$)$_{n1}$-halide in the presence of a base such as DIPEA to yield a compound of formula (I), wherein n1=0 to 2 and X$^4$ is S(O)$_2$N(R$^{1a}$);
(viii) a three step process a. to c. where by;
a. 2-chloroethanol is first reacted with isocyanatosulfuryl chloride in the presence of base to form an intermediate compound of formula (XV)

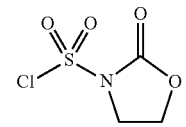

(XV)

b. reacting a compound of formula (XV) with a compound of formula (IV), (IVb), (V), (VIII), (IX), (XII) or (XIV), wherein the meanings are as indicated above
c. followed by reacting the resulting intermediate from step b. with a compound of formula HN(R$^{1a}$)(CH$_2$)$_{n2}$R$^2$ in base such as TEA and at elevated temperature (usually 40 to 85° C.) to yield a compound of formula (I), wherein n1=0 and X$^4$ is S(O)$_2$N(R$^{1a}$).
(ix) a compound of formula R$^2$(CH$_2$)$_{n2}$C(O)(CH$_2$)$_{n1}$-halide in the presence of a base such as DIPEA and optionally at elevated temperature (usually 30 to 120° C.) to yield a compound of formula (I), wherein n1=1 to 2 and X$^4$ is C(O);
(x) a two step process d. to e. where by;
d. a compound of formula ClC(O)(CH$_2$)$_{n1}$-halide in the presence of base is first reacted with a compound of formula R$^2$(CH$_2$)$_{n2}$X$^{4'}$ to form an intermediate compound of formula (XVa), wherein n1=1 to 2 and X$^{4'}$ is OH, NH$_2$ or NHR$^{1a}$

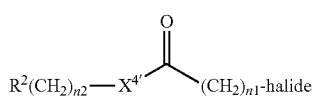
(XVa)

e. reacting a compound of formula (XVa) in the presence of a base such as DIPEA and optionally at elevated temperature (usually 30 to 120° C.) with a compound of formula (IV), (IVb), (V), (VIII), (IX), (XII) or (XIV) to yield a compound of formula (I), wherein the meanings are as indicated above; or
(xi) a two step process f. to g. where by;
f. a compound of formula ClS(O)$_2$(CH$_2$)$_{n1}$-halide in the presence of base is first reacted with a compound of formula R$^2$(CH$_2$)$_{n2}$X$^{4'}$ to form an intermediate compound of formula (XVb), wherein n1=1 to 2 and X$^{4'}$ is NH$_2$ or NHR$^{1a}$

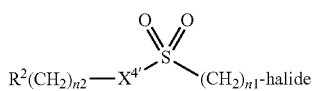
(XVb)

g. reacting a compound of formula (XVb) in the presence of a base such as DIPEA and optionally at elevated temperature (usually 30 to 120° C.) with a compound of formula (IV), (IVb), (V), (VIII), (IX), (XII) or (XIV) to yield a compound of formula (I), wherein the meanings are as indicated above Accordingly, another aspect of the present invention is a method for the preparation of a compound of any of the present invention, comprising the steps of
reacting a compound of formula (Ia)

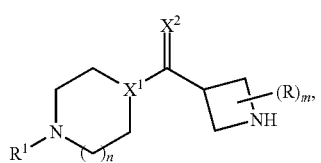
(Ia)

wherein R$^1$, n, X$^1$, X$^2$, R, m have the meaning as indicated above with
(i) an activated ester or anhydride of a compound of formula R$^2$(CH$_2$)$_{n2}$C(O)OH in the presence of amide coupling reagents to yield a compound of formula (I), wherein n1=0 and X$^4$ is C(O); or
(ii) a compound of formula R$^2$(CH$_2$)$_{n2}$NCO to yield a compound of formula (I), wherein n1=0 and X$^4$ is C(O)NH; or
(iii) a compound of formula R$^2$(CH$_2$)$_{n2}$S(O)$_2$(CH$_2$)$_{n1}$-halide in the presence of a base to yield a compound of formula (I), wherein n1=0 to 2 and X$^4$ is S(O)$_2$; or
(iv) a compound of formula R$^2$(CH$_2$)$_{n2}$(R$^{1a}$)NC(O)(CH$_2$)$_{n1}$-halide in the presence of a base to yield a compound of formula (I), wherein n1 is 0 to 2 and X$^4$ is C(O)N(R$^{1a}$); or
(v) a compound of formula R$^2$(CH$_2$)$_{n2}$OC(O)(CH$_2$)$_{n1}$-halide in the presence of a base to yield a compound of formula (I), wherein n1=0 to 2 and X$^4$ is C(O)O; or (vi) a compound of formula R$^2$(CH$_2$)$_{n2}$(R$^{1a}$)NS(O)$_2$(CH$_2$)$_{n1}$-halide in the presence of a base to yield a compound of formula (I), wherein n1=0 to 2 and X$^4$ is S(O)$_2$N(R$^{1a}$); or
(vii)
(aa) an intermediate compound of formula (XV)

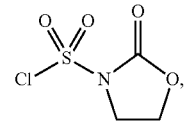
(XV)

resulting from the reaction of 2-chloroethanol with isocyanatosulfuryl chloride in the presence of a base; followed by
(bb) reacting the resulting intermediate from step (aa) with a compound of formula HN(R$^{1a}$)(CH$_2$)$_{n2}$R$^2$ in the presence of a base at elevated temperature to yield a compound of formula (I), wherein n=0 and X$^4$ is S(O)$_2$N(R$^{1a}$); or
(viii) a compound of formula R$^2$(CH$_2$)$_{n2}$C(O)(CH$_2$)$_{n1}$-halide in the presence of a base and optionally at elevated temperature to yield a compound of formula (I), wherein n1=1 to 2 and X$^4$ is C(O); or
(ix) an intermediate compound of formula (XVa)

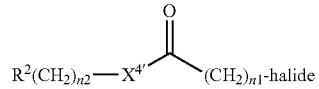
(XVa)

resulting from the reaction of a compound of formula ClC(O)(CH$_2$)$_{n1}$-halide in the presence of base optionally at elevated temperature with a compound of formula R$^2$(CH$_2$)$_{n2}$X$^{4'}$, wherein n1=1 to 2 and X$^{4'}$ is OH, NH$_2$ or NHR$^{1a}$; or
(x) an intermediate compound of formula (XVb)

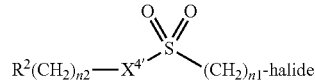
(XVb)

resulting from the reaction of a compound of formula ClS(O)$_2$(CH$_2$)$_{n1}$-halide in the presence of a base and a compound of formula R$^2$(CH$_2$)$_{n2}$X$^{4'}$, wherein n1=1 to 2 and X$^{4'}$ is NH$_2$ or NHR$^{1a}$.

The method may comprise either of the further steps when R$^{1a}$ of the above methods is H:
(a) reacting the resulting secondary amine with a suitable alkyl halide or activated alcohol (such as OMs or OTs) in the presence of an organic base (such as TEA) or NaH at temperatures between 0° C. and 200° C., to yield a compound of formula (I), wherein R$^{1a}$ is alkyl; or
(b) reacting the secondary amine with a suitable alkyl aldehyde in the presence of an organic acid (such as AcOH) and reducing agent (such as NaBH$_3$CN or STAB) at room temperature or elevated temperature (up to 100° C.), to yield a compound of formula (I), wherein R$^{1a}$ is alkyl.

Additionally a compound of formula (I), wherein n1=0 and $X^4$ is C(O)O may comprise a further step comprising of;

(a) reacting the carbamate compound of formula (I) with a primary or secondary amine in the presence of base (such as DIPEA) at room temperature or elevated temperatures of up to 200° C.), to yield a compound of formula (I) with a respective urea group ($X^4$=C(O)N($R^{1a}$)).

The method may comprise the further steps where compounds of formula (I), wherein the meanings are as indicated above and $R^2$ has a potentially chemically reactive group, are further modified as follows:

(a) reacting a suitable alcohol or (hetero)aryl alcohol with a strong base (such as NaH or $^t$BuOK) and the resulting alkoxide or (hetero)aryloxide reacted (usually between room temperature and 180° C.) with the halide or activated alcohol (sulfonate) substituent of $R^2$, to yield a compound of formula (I); or (b) reacting a halide or activated alcohol (sulfonate) substituent of $R^2$ in a Suzuki reaction using a palladium phosphine catalyst (such as that formed from $Pd_2(dba)_3$ and tricyclohexylphosphine) and suitable boronate ester or boronic acid (usually at room temperature to 150° C.) in the presence of a base (such as $K_3PO_4$ or $K_2CO_3$), to yield a compound of formula (I); or (c) reacting the compound of formula (I) with a primary or secondary amine optionally in the presence of base (such as DIPEA or $K_2CO_3$) at room temperature or elevated temperatures of up to 200° C., to yield a compound of formula (I).

The method may comprise the further steps where compounds of formula (I), wherein the meanings are as indicated above and $R^2$ includes a primary or secondary amine, are further modified as follows:

(a) reacting the amine of a compound of formula (I) with a (hetero)aromatic halide at elevated temperature (up to 120° C.) in the presence of palladium catalysed coupling reagents (such as $Pd_2(dba)_3$, BINAP and $^t$BuOK) to yield compounds of formula (I).

The same reaction types may apply for compounds of the present invention, where in formula (I) m is other than 0.

The method may comprise the further step where compounds of formula (I) represented by formula (XVI), wherein the meanings are as indicated above, are further modified as follows;

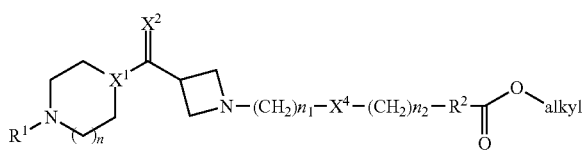

(XVI)

(a) reacting the ester group with a Grignard reagent (such as MeMgBr), optionally in the presence of lithium chloride, at a temperature usually between −78° C. and 150° C., to yield a compound of formula (I);

(b) saponifying the ester group using aqueous base (such as aqueous lithium hydroxide) and coupling the resulting acid with an amine of formula HN($R^4R^{4a}$) using amide coupling reagents (such as HOBt and HBTU or HOBt and EDCI) usually between 0° C. and 85° C. to yield a compound of formula (I); or (c) reacting the ester group with an amine of formula HN($R^4R^{4a}$) in the presence of a solution of $AlMe_3$, usually between 0° C. and 85° C. to yield a compound of formula (I).

The method may comprise the further step where compounds of formula (I) represented by formula (XVII), wherein the meanings are as indicated above, are further modified as follows;

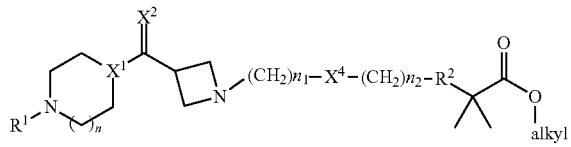

(XVII)

(a) reducing the ester group (usually with LAH) at temperatures ranging from −50 to 100° C., to yield a compound of formula (I).

The same reaction types may apply for compounds of the present invention, where in formula (I) m is other than 0.

EXAMPLES

Biological Evaluation:
Cell-lines Used to Characterize Invented Compounds In Vitro
CHO—K1 cell line expressing human H3 receptors were purchased from Euroscreen (Gosselies, Belgium, Cat. no.: ES-392-C)

Human H3 receptor-expressing cell-lines were grown in Ham's F12 [Sigma, Cat. no. N6658], supplemented with 10% FBS [Sigma, Cat. no. F9665], 400 µg/ml G418 [Sigma, Cat. no. N1876] and 250 µg/ml Zeocin [Invitrogen, Cat. no. 46-0509]) according to the protocol provided by Euroscreen.

cAMP Quantification Protocol for Human H3 Receptor Testing

The assay measures the ability of test compounds to inhibit Histamine receptor agonist-induced decrease of intracellular free cAMP (receptor is $G_i$ coupled).

Specifically, a cAMP quantification assay system from DiscoveRx (cAMP XS+; Cat. no. 90-0075) was used.

For the cAMP assay, confluent cells were detached from the culture vessels with 1× trypsin-EDTA solution (Sigma), and seeded into 384-well Costar plates (white, clear bottom, Cat. no. 3707) at a density of 10,000 cells per well. Cells were seeded in a volume of 50 µl in medium without antibiotics and incubated overnight in a humidified atmosphere with 5% $CO_2$ at 37° C. The cAMP assay was performed according to the protocol provided by DiscoveRx.

The cell culture medium was removed and the cells washed once with PBS (50 µl per well). The plates were emptied by inversion and 7.5 µl/well of compound in PBS (containing 1 mM IBMX and 0.03% BSA) were added and incubated for 30 min at 37° C.

Subsequent 7.5 µl/well specific agonist solution was added and the plates for another 30 min incubated at 37° C.

The following agonist solution is used for the individual cell-lines:
hH3: 100 nM histamine, 10 µM forskolin in PBS (containing 1 mM IBMX and 0.03% BSA)

After the incubation with the agonist, 5 µl/well cAMP XS antibody solution was added followed by 20 µl/well Gal/EII/Lysis (1:5:19)+ED (1:1). The plates were incubated for one hour at room temperature and afterwards 20 µl/well EA reagent was added. The luminescence was developed for approximately three hours at room temperature and the plates were read out using a 'BMG Novostar' plate reader.

Assaying of Compounds

Test compounds were assayed at 8 concentrations in triplicate. Serial 10-fold dilutions in 100% DMSO were made at a 100-times higher concentration than the final concentration. and then diluted with a 2 step protocol in assay buffer to reach the required assay concentrations and 1% DMSO.

The specific compounds exemplified below were categorized by the following potency ranges ($IC_{50}$ values):
A: <50 nM; B: >50 nM to 100 nM; C: >100 nM to 5000 nM.

Synthesis of Compounds:

Analytical Methods

NMR Spectrometers Used:

Bruker DRX 500 MHz NMR
Bruker AVANCE 400 MHz NMR
Bruker DPX 250 MHz NMR
Bruker DPX 360 MHz NMR Configuration of the Bruker DRX 500 MHz NMR High performance digital NMR spectrometer, 2-channel microbay console and Windows XP host workstation running Topspin version 1.3.

Equipped with:

Oxford instruments magnet 11.74 Tesla (500 MHz proton resonance frequency)

B-VT 3000 temperature controller

GRASP II gradient spectroscopy accessory for fast acquisition of 2D pulse sequences Deuterium lock switch for gradient shimming 5 mm Broad Band Inverse geometry double resonance probe with automated tuning and matching (BBI ATMA). Allows $^1H$ observation with pulsing/decoupling of nuclei in the frequency range $^{15}N$ and $^{31}P$ with $^2H$ lock and shielded z-gradient coils.

Configuration of the Bruker DPX 250 MHz NMR

High performance one bay Bruker 250 MHz digital two channel NMR spectrometer console and Windows XP host workstation running XwinNMR version 3.5.

Equipped with:

Oxford instruments magnet 5.87 Tesla (250 MHz proton resonance frequency)

B-VT 3300 variable temperature controller unit

Four nucleus (QNP) switchable probe for observation of $^1H$, $^{13}C$, $^{19}F$ and $^{31}P$ with $^2H$ lock Configuration of the Bruker AVANCE 400 MHz NMR High performance one bay Bruker AVANCE 400 MHz digital two channel NMR spectrometer console Equipped with:

Bruker magnet 9.40 Tesla (400 MHz proton resonance frequency)

B-VT 3200 variable temperature controller unit

GRASP II gradient spectroscopy accessory for the generation of one field gradient of up to 50 Gauss $cm^{-1}$ Four nucleus (QNP) switchable probe for observation of $^1H$, $^{13}C$, $^{19}F$ and $^{31}P$ with $^2H$ lock with z-gradient coils for gradient spectroscopy.

LCMS Methods Used

Example compounds and their intermediates were analysed by HPLC-MS using a combination of the following methods.

LCMS Method A (2 min Method)

| | Generic 2 minute method | |
|---|---|---|
| Column | Atlantis dC18 | |
| | 2.1 × 30 mm, 3 um | |
| Mobile phase | A = Formic acid (aq) 0.1% | |
| | B = Formic acid | |
| | (acetonitrile) 0.1% | |
| Flow rate | 1 mL/min | |
| Injection volume | 3 ul | |
| Detector | 215 nm (nominal) | |
| Gradient | Time (min) | % Organic |
| | 0 | 5 |
| | 1.50 | 100 |
| | 1.60 | 100 |
| | 1.61 | 5 |

LCMS Method B (3 min Method)

| | Standard 3 minute method | |
|---|---|---|
| Column | Atlantis dC18 | |
| | 2.1 × 50 mm, 5 um | |
| Mobile phase | A = Formic acid (aq) 0.1% | |
| | B = Formic acid | |
| | (acetonitrile) 0.1% | |
| Flow rate | 1 mL/min | |
| Injection volume | 3 ul | |
| Detector | 215 nm (nominal) | |
| Gradient | Time (min) | % Organic |
| | 0 | 5 |
| | 2.5 | 100 |
| | 2.7 | 100 |
| | 2.71 | 5 |
| | 3.0 | 5 |

LCMS Method C (7 min Method)

| | High resolution method | |
|---|---|---|
| Column | Waters Atlantis dC18 | |
| | 100 × 2.1 mm, 3 µm column | |
| | 40° C. | |
| Mobile phase | A - 0.1% Formic acid (water) | |
| | B - 0.1% Formic acid (acetonitrile) | |
| Flow rate | 0.6 mL/min | |
| Injection volume | 3 ul | |
| Detector | 215 nm (nominal) | |
| Gradient | Time (min) | % Organic |
| | 0.00 | 5 |
| | 5.00 | 100 |
| | 5.40 | 100 |
| | 5.42 | 5 |
| | 7.00 | 5 |

LCMS Method D (7 min Method)

|  | High pH method, high resolution |  |
| --- | --- | --- |
| Column | Phenomenex Gemini C18 2.0 × 100 mm, 3 um 50° C. | |
| Mobile phase | A = 2 mM Amm. Bicarbonate, buffered to pH 10 B = Acetonitrile | |
| Flow rate | 0.5 ml/min | |
| Injection volume | 3 ul | |
| Detector | 215 nm (nominal) | |

| Gradient | Time (mins) | % Organic |
| --- | --- | --- |
|  | 0 | 5 |
|  | 5.50 | 100 |
|  | 5.90 | 100 |
|  | 5.92 | 5 |

LCMS Method E (10 min Method)

| Column | Chromolith Speed Rod RP-18c 4.6 × 50 mm |
| --- | --- |
| Mobile phase | A - Buffer + Acetonitrile (95:5) Buffer: 0.01% ammonium acetate pH 5.00 (water) B - acetonitrile |
| Flow rate | 1.5 mL/min |
| Injection volume | 10 ul |
| Detector | PDA detector Detection: Spectrum Max |

| Gradient | Time (min) | % Organic |
| --- | --- | --- |
|  | 0.00 | 5 |
|  | 0.60 | 5 |
|  | 5.00 | 95 |
|  | 8.00 | 95 |
|  | 8.50 | 5 |
|  | 10.0 | 5 |

LCMS Method F (15 min Method)

| Column | Waters X-terra MS C-18 4.6 × 50 mm, 5 micron |
| --- | --- |
| Mobile phase | A - Buffer + Acetonitrile (95:5) Buffer: 0.01% ammonium acetate pH 5.00 (water) B - acetonitrile |
| Flow rate | 1.0 mL/min |
| Injection volume | 10 ul |
| Detector | PDA detector Detection: Spectrum Max |

| Gradient | Time (min) | % Organic |
| --- | --- | --- |
|  | 0.00 | 5 |
|  | 1.00 | 5 |
|  | 7.00 | 95 |
|  | 12.0 | 95 |
|  | 13.0 | 5 |
|  | 15.0 | 5 |

Preparative HPLC Methods Used:

Where indicated, Example compounds and their intermediates were purified by one of or any combination of the following methods.

Prep Method 1 (Low pH)

| Column | Waters SunFire Prep C18 OBD 5 um 19 × 100 mm |
| --- | --- |
| Mobile Phase | A, TFA (aq) 0.1% B, TFA (CH₃CN) 0.1% |

Prep Method 2 (FTE High pH)

| Column | Phenomenex Gemini C18 NX 5 u 100 × 21.2 mm |
| --- | --- |
| Mobile Phase | A, 2 mM ammonium bicarbonate, buffered to pH 10 B, Acetonitrile: 2 mM ammonium bicarbonate 95:5 |

Prep Method 3 (Low pH)

| Column | Waters SunFire Prep C18 OBD 5 um 19 × 100 mm |
| --- | --- |
| Mobile Phase | A, $HCO_2H$ (aq) 0.1% B, $HCO_2H$ (MeOH) 0.1% |

Prep Method 4 (FTE prep)

| Column | Waters SunFire Prep C18 OBD 5 um 19 × 100 mm |
| --- | --- |
| Mobile Phase | A, $H_2O$ B, $CH_3CN$ |

Prep Method 5 (Neutral)

| Column | Waters SunFire Prep C18 OBD 5 um 19 × 100 mm |
| --- | --- |
| Mobile Phase | A, $H_2O$ B, MeOH |

Compound Naming

All compounds are named using ACD Labs 10.0 naming software which conforms to IUPAC naming protocols. Some compounds are isolated as TFA, formic acid or fumaric acid salts, which is not reflected by the chemical name. Within the meaning of the present invention the chemical name represents the compound in neutral form as well as its TFA, formic acid or fumaric acid salt or any other salt, especially pharmaceutically acceptable salt, if applicable.

List Of Abbreviations
AcOH acetic acid
bR s broad singlet
Boc tert-butoxycarbonyl
BINAP 2,2'-bis(diphenylphosphino)-1,1'binaphthyl
$^t$BuOK potassium tert-butoxide
ca. circa cat catalytic
CDI 1,1'-carbonyldiimidazole
Chloroform-d deuterated chloroform
CDCl₃ deuterated chloroform
DCC dicyclohexylcarbodiimide
DCE 1,2-dichloroethane
DCM dichloromethane
DIPEA N,N-diisopropylethylamine
DMAP N,N-4-dimethylaminopyridine
EDCI 1-ethyl-3-(3-dimethylaminopropyl)carbodiimide hydrochloride
eq equivalent
Ether diethyl ether
Et₂O diethyl ether
EtOAc ethyl acetate
EtOH ethanol
FCC flash column chromatography
h hours
HCl hydrochloric acid
HOBt 1-hydroxybenzotriazole
HBTU o-benzotriazol-1-yl-N,N,N',N'-tetramethyluronium tetrafluoroborate
IBX 1-hydroxy-1,2-benziodoxol-3(1h)-one 1-oxide
LAH lithium aluminium hydride
LCMS liquid chromatography and mass spectrometry
MeCN acetonitrile
MeOH methanol
MeOD dueterated methanol
MsCl methanesulfonyl chloride
m multiplet
min(s) minute(s)
ml millilitre
mL millilitre
mol/M mole/molar
MW molecular weight
NaH sodium hydride
NMR nuclear magnetic resonance
NaBH₃CN sodium cyanoborohydride
NaBH₄ sodium borohydride
OMs methanesulfonate
OTs para-toluenesulfonate
Pd₂(dba)₃ bis(dibenzylideneacetone)palladium(0)
PBr₃ tribromophospine
PMA phosphomolibdic acid
PPh₃ triphenylphosphine
PS-DIPEA polymer-supported N,N-diisopropylethylamine
Rt retention time
RT room temperature
STAB sodium triacetoxyborohydride
thio-CDI thio-carbonyl diimidazole
TBAF tetra-n-butylammonium fluoride
TBAI tetra-n-butylammonium iodide
TBDMSCl tert-butyldimethylsilyl chloride
TEA triethylamine
TFA 2,2,2-trifluoroacetic acid
TFE 2,2,2-trifluoroethanol
THF tetrahydrofuran
TLC thin layer chromatography
TMS trimethylsilyl
wt weight Route 1

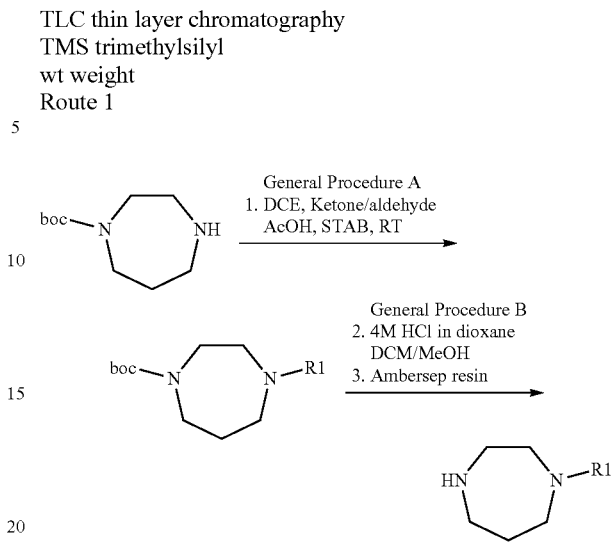

General Procedure A:

Preparation of tert-butyl 4-cyclobutyl-1,4-diazepane-1-carboxylate

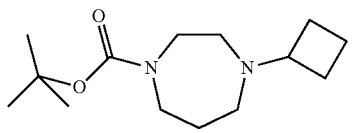 [SMILES: CC(C)(C)OC(=O)N1CCCN(C2CCC2)CC1]

To a stirred solution of [1,4]diazepane-1-carboxylic acid tert-butyl ester (5 g, 24.97 mmol) in DCE (70 ml) at 20 to 25° C. was added cyclobutanone (1.75 g, 24.97 mmol) followed by acetic acid (1.5 g, 24.97 mmol) dropwise. The resulting mixture was stirred at 20 to 25° C. for ca. 2 h. Sodium triacetoxyborohydride (7.94 g, 37.46 mmol) was added in 9 portions, keeping the temperature in the range of 20 to 25° C. The resulting suspension was stirred at 20 to 25° C. overnight. Saturated aqueous NaHCO₃ (80 ml) was added in four portions and the biphasic mixture stirred at 20 to 25° C. for ca. 0.5 h. The organic layer was separated, washed with water (20 ml) and the aqueous phase back extracted at pH 9 with DCM (20 ml). The combined organic phases were dried (Na₂SO₄), filtered and concentrated at reduced pressure to provide the title compound (6.1 g, 96% yield) as yellow oil.

LCMS data: Calculated MH⁺ (255). Found 100% [2(M-Boc)]H⁺ m/z (307), Rt=1.4 min.

NMR data: ¹H NMR (400 MHz, MeOD) δ ppm 3.38-3.52 (4H, m), 2.86-2.98 (1H, m), 2.40-2.54 (4H, m), 2.02-2.12 (2H, m), 1.77-1.92 (4H, m), 1.61-1.75 (2H, m), 1.46 (9 H, s).

General Procedure B:

Preparation of 1-cyclobutyl-1,4-diazepane

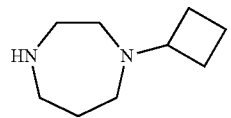 [SMILES: C1CC(N2CCCNCC2)C1]

To a stirred solution of tert-butyl 4-cyclobutyl-1,4-diazepane-1-carboxylate (6.1 g, 23.98 mmol) in DCM (70 ml) at 20 to 25° C. was added a solution of 4M HCl in dioxane (30 ml, 120 mmol) dropwise. The resulting mixture was stirred at 20 to 25° C. for ca. 2 h. MeOH (6 ml) was added and the resulting mixture stirred at 20 to 25° C. for 1 to 2 days. The solvent was removed at reduced pressure and the resulting gummy residue slurried in ether (100 ml) for 0.5 h. The solvent was evaporated and the residue slurried in ether/MeOH (10:1, 66 ml). The resulting white solid was collected by filtration, suspended in DCM (150 ml) and treated with 2M NaOH. The aqueous phase was extracted with DCM until complete transfer of product in the organic layer, as monitored by TLC analysis (eluent, DCM/MeOH/conc.NH$_3$ (90:10:1); stain, PMA) was achieved. The combined organic phases were dried (Na$_2$SO$_4$), filtered and concentrated at reduced pressure to provide the title compound (2.67 g, 73% yield) as orange oil.

LCMS data: Calculated MH$^+$ (155). Found 100% (MH$^+$) m/z 155, Rt=0.44 min.

NMR data: $^1$H NMR (400 MHz, Chloroform-d) δ ppm 2.85-2.97 (5 H, m), 2.43-2.53 (4 H, m), 1.97-2.08 (2 H, m), 1.52-1.91 (7 H, m).

Route 2

To a 0° C. stirred solution of 3-azetidine carboxylic acid (500 mg, 4.95 mmol) in 2 M K$_2$CO$_3$ aqueous (5 ml) and dioxane (5 ml), benzyl chlorocarbonate (929 mg/0.78 ml, 5.45 mmol) was added dropwise. The reaction mixture was allowed to warm to RT and stirred for 15 hours. The reaction was monitored by TLC. Upon completion the reaction mixture was quenched with piperazine (42 mg, 0.50 mmol), concentrated at reduced pressure and treated with 2 M aqueous HCl (10 ml). The aqueous layer was extracted with EtOAc (5×10 ml), the phases separated, dried (MgSO$_4$), filtered and concentrated at reduced pressure. The crude orange oil was purified by silica FCC to give the title compound (760 mg, 65% yield) as a white solid.

LCMS data (reaction IPC): Calculated MH$^+$ (236). Found 7% (MH$^+$) m/z 236, Rt=1.09 min.

NMR data: $^1$H NMR (500 MHz, Chloroform-d) δ ppm 8.49 (1 H, br. s.), 7.30-7.42 (5 H, m), 5.10-5.15 (2 H, m), 4.18-4.27 (4 H, m), 3.43 (1 H, m).

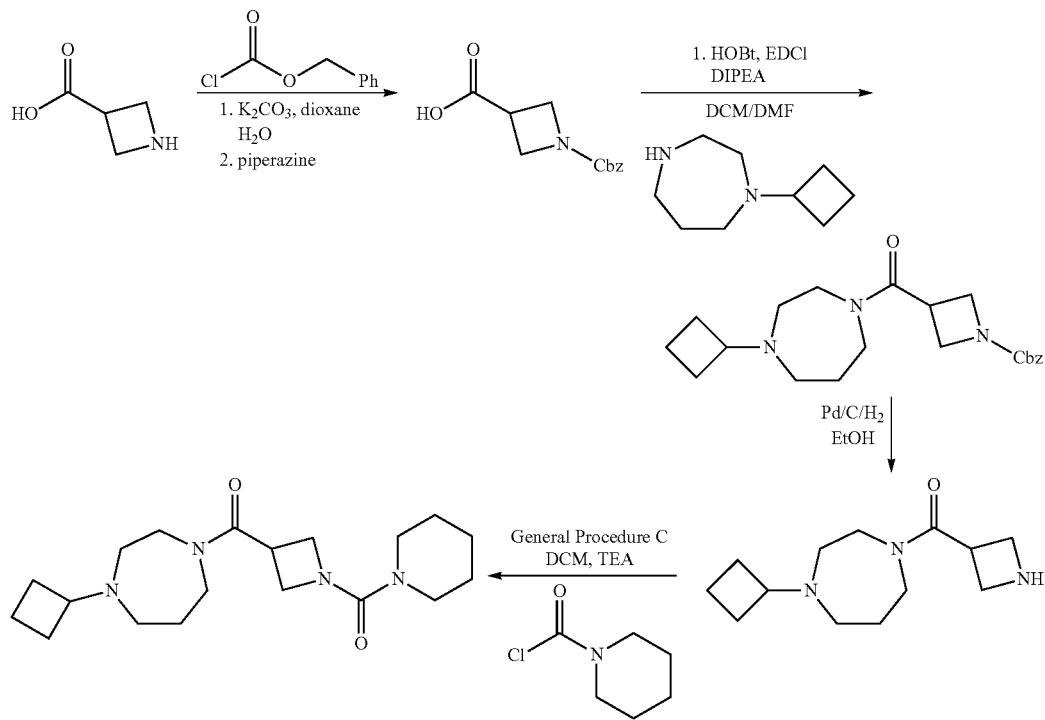

Preparation of benzyl 3-[(4-cyclobutyl-1,4-diazepan-1-yl)carbonyl]azetidine-1-carboxylate Example 1

Preparation of benzyl 3-[(4-cyclobutyl-1,4-diazepan-1-yl)carbonyl]azetidine-1-carboxylate. Potency Range A

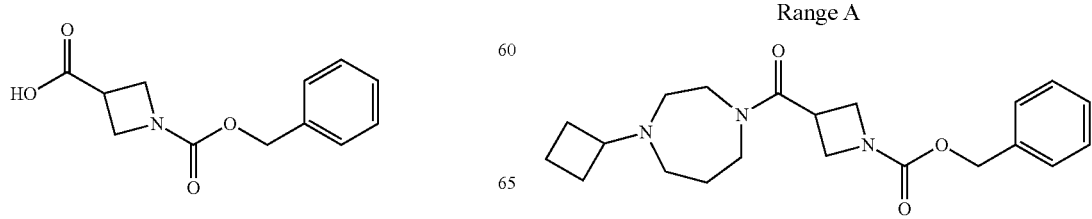

To a stirred solution of 1-[(benzyloxy)carbonyl]azetidine-3-carboxylic acid (500 mg, 2.13 mmol) in DMF/DCM (1:10) (11 ml) was added HOBt (287 mg, 2.13 mmol) and EDCI (490 mg, 2.56 mmol). The resulting suspension was stirred at RT for 10 mins before dropwise addition of 1-cyclobutyl-1,4-diazepane (328 mg, 2.13 mmol) in DCM (3 ml). After stirring for 16 h at RT the reaction was shown to be complete by TLC and the solvent was evaporated at reduced pressure. The residue was treated with saturated aqueous NaHCO$_3$ (10 ml) and the resulting aqueous extracted with EtOAc (3×7.5 ml). The combined organic phases were dried (MgSO$_4$), filtered and concentrated at reduced pressure. Purification by silica FCC (eluting with 99:1 to 97:3 gradient of DCM/2M NH$_3$ in MeOH) provided the title compound (475 mg, 60% yield) as a yellow oil.

LCMS data: Calculated MH$^+$ (372). Found 97% (MH$^+$) m/z 372, Rt=2.51 min (Method C).

NMR data: $^1$H NMR (500 MHz, CHLOROFORM-d) δ ppm 7.29-7.41 (5 H, m), 5.10 (2 H, s), 4.19-4.47 (2 H, m), 4.07-4.18 (2 H, m), 3.59-3.71 (2 H, m), 3.48-3.58 (1 H, m), 3.33 (2 H, m), 2.85 (1 H, m), 2.45-2.56 (2 H, m), 2.34-2.45 (2 H, m), 1.97-2.10 (2 H, m), 1.73-1.92 (4 H, m), 1.58-1.73 (2 H, m).

Preparation of 1-(azetidin-3-ylcarbonyl)-4-cyclobutyl-1,4-diazepane

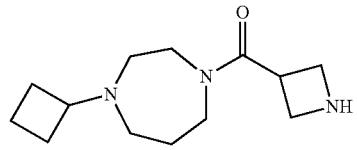 [SMILES: O=C(C1CNC1)N1CCCN(C2CCC2)CC1]

To a solution of benzyl 3-[(4-cyclobutyl-1,4-diazepan-1-yl)carbonyl]azetidine-1-carboxylate (420 mg, 1.13 mmol) in EtOH (10 ml) was added 5% Pd—C (42 mg, 10% wt/wt). The flask was evacuated and the vacuum purged with N$_2$ gas. The flask was evacuated again and the vacuum purged with H$_2$ gas. The reaction was complete after 16 h, as shown by $^1$H NMR. The suspension was filtered through Celite® with MeOH washings (3×5 ml), and the combined filtrate dried (MgSO$_4$), filtered and concentrated at reduced pressure to give the title compound (248 mg, 93% yield) as a viscous pale yellow oil.

LCMS data: Calculated MH$^+$ (238). Found (MH$^+$) m/z 238 Rt=2.91-3.02 min (Method D).

NMR data: $^1$H NMR (500 MHz, CHLOROFORM-d) δ ppm 4.01-4.08 (2 H, m), 3.72-3.80 (1 H, m), 3.67-3.72 (2 H, m), 3.60-3.67 (2 H, m), 3.33-3.38 (2 H, m), 2.86 (1 H, m), 2.48 (2 H, td, J=10.3, 5.0 Hz), 2.35-2.44 (3 H, m), 1.99-2.09 (2 H, m), 1.75-1.90 (4 H, m), 1.57-1.72 (2 H, m).

General Procedure C:

Example 2

Preparation of 1-cyclobutyl-4-{[1-(piperidin-1-ylcarbonyl)azetidin-3-yl]carbonyl}-1,4-diazepane. Potency Range A

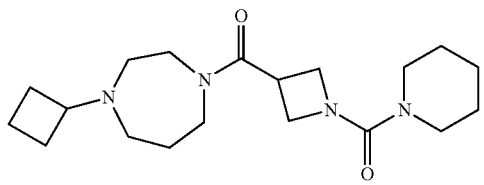 [SMILES: O=C(C1CN(C(=O)N2CCCCC2)C1)N1CCCN(C2CCC2)CC1]

To a stirred 0° C. solution of 1-(azetidin-3-ylcarbonyl)-4-cyclobutyl-1,4-diazepane (20 mg, 0.084 mmol) in DCM (1 ml) and TEA (0.023 ml, 0.17 mmol) was added dropwise piperidine-1-carbonyl chloride (14.9 mg, 0.013 ml, 0.10 mmol). The reaction was stirred for 1 h and then allowed to warm to RT and the progress monitored by LCMS. After 1 h the reaction was quenched with water (5 ml), extracted with DCM (2×10 ml), dried (MgSO$_4$), filtered and concentrated at reduced pressure. Purification by silica FCC (eluting with 99:1 to 96:4 gradient of DCM/2M NH$_3$ in MeOH) provided impure title compound (22 mg, 78%) as brown oil. Re-purification by preparative HPLC provided the title compound (3 mg, 10% yield) as a colourless oil.

LCMS data: Calculated MH$^+$ (348). Found 95% (MH$^+$) m/z 348, Rt=2.19 min (Method D).

NMR data: $^1$H NMR (500 MHz, CHLOROFORM-d) δ ppm 4.08-4.20 (2 H, m), 3.97-4.06 (2 H, m), 3.56 (2 H, m), 3.36-3.48 (1 H, m), 3.24-3.31 (2 H, m), 3.16-3.22 (4 H, m), 2.72-2.83 (1 H, m), 2.42 (2 H, m), 2.34 (2 H, m), 1.96 (2 H, m), 1.77 (4 H, m), 1.49-1.66 (10 H, m), 1.38-1.48 (4 H, m).

The following compound was prepared as described in Route 2, General Procedure C above.

Example 3

Preparation of 1-cyclobutyl-4-{[1-(morpholin-4-ylcarbonyl)azetidin-3-yl]carbonyl}-1,4-diazepane. Potency Range A

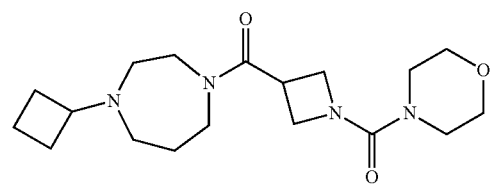 [SMILES: O=C(C1CN(C(=O)N2CCOCC2)C1)N1CCCN(C2CCC2)CC1]

In a similar fashion (Route 2, GP C), 1-(azetidin-3-ylcarbonyl)-4-cyclobutyl-1,4-diazepane (30 mg, 0.126 mmol) and morpholine-4-carbonyl chloride (23 mg, 0.151 mmol) gave the title compound (6.6 mg, 15% yield) as colourless oil after purification by silica FCC (eluting with 99:1 to 96:4 gradient of DCM/2M NH$_3$ in MeOH).

LCMS data: Calculated MH$^+$ (351). Found 95% (MH$^+$) m/z 351, Rt=3.15 min (Method D).

NMR data: $^1$H NMR (250 MHz, CHLOROFORM-d) δ ppm 4.13-4.23 (2 H, m), 4.04 (2 H, m), 3.54-3.63 (6 H, m), 3.36-3.52 (1 H, m), 3.27 (6 H, m), 2.71-2.85 (1 H, m), 2.42 (2 H, m), 2.29-2.38 (2 H, m), 1.90-2.04 (2 H, m), 1.43-1.87 (10 H, m).

Route 3

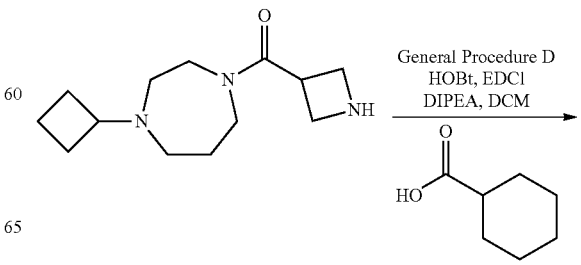

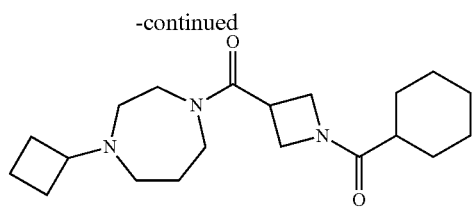

General Procedure D:

Example 4

Preparation of 1-cyclobutyl-4-{[1-(cyclohexylcarbonyl)azetidin-3-yl]carbonyl}-1,4-diazepane. Potency Range A

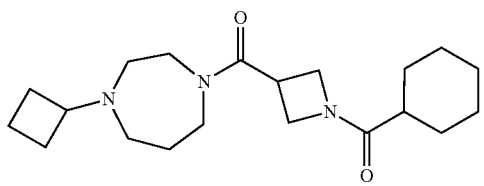

To a stirred solution of cyclohexanecarboxylic acid (10.8 mg, 0.084 mmol) in DCM/DMF (1.1 ml) was added HOBt (11.4 mg, 0.084 mmol) and EDCI (16.1 mg, 0.084 mmol). After 10 mins a solution of 1-(azetidin-3-ylcarbonyl)-4-cyclobutyl-1,4-diazepane (20 mg, 0.084 mmol) in DCM (1 ml) and DIPEA (0.01 ml, 0.084 mmol) was added dropwise. After 15 h the solvent was evaporated at reduced pressure and purified by silica FCC (eluting with 99:1 to 95:5 gradient of DCM/2M NH$_3$ in MeOH) to give the title compound (24 mg, 82% yield) as brown oil.

LCMS data: Calculated MH$^+$ (348). Found 100% (MH$^+$) m/z 348 and (MNa$^+$) 370.1, Rt=2.19 min (Method C).

NMR data: $^1$H NMR (500 MHz, CHLOROFORM-d) δ ppm 4.57 (1 H, m), 4.13-4.23 (2 H, m), 4.05 (1 H, m), 3.56-3.74 (2 H, m), 3.52 (1 H, m), 3.29-3.41 (2 H, m), 2.81-2.90 (1 H, m), 2.49-2.57 (1 H, m), 2.43-2.49 (2 H, m), 2.34-2.42 (1 H, m), 2.15 (1 H, m), 2.03 (2 H, m), 1.89 (2 H, m), 1.75-1.85 (4 H, m), 1.57-1.72 (4 H, m), 1.38-1.54 (2 H, m), 1.15-1.32 (4 H, m).

The following compounds were prepared as described in Route 3, General Procedure D above.

Example 5

Preparation of 1-cyclobutyl-4-{[1-(tetrahydro-2H-pyran-4-ylcarbonyl)azetidin-3-yl]carbonyl}-1,4-diazepane. Potency Range A

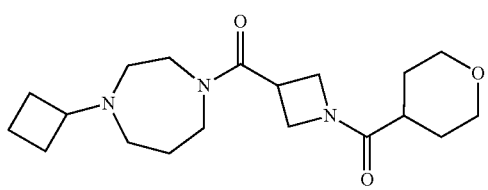 [SMILES: O=C(C1CN(C(=O)C2CCOCC2)C1)N1CCCN(C2CCC2)CC1]

In a similar fashion (Route 3, GP D), tetrahydro-2H-pyran-4-carboxylic acid (16.4 mg, 0.13 mmol) and 1-(azetidin-3-ylcarbonyl)-4-cyclobutyl-1,4-diazepane (30 mg, 0.13 mmol) gave the title compound (15 mg, 34% yield) as colourless oil.

LCMS data: Calculated MH$^+$ (349). Found 99% (MH$^+$) m/z 349, Rt=3.14 min (Method C).

NMR data: $^1$H NMR (500 MHz, CHLOROFORM-d) δ ppm 4.59-4.65 (1 H, m), 4.14-4.27 (2 H, m), 3.96-4.10 (3 H, m), 3.49-3.76 (3 H, m), 3.29-3.46 (4 H, m), 2.81-2.91 (1 H, m), 2.34-2.58 (5 H, m), 1.99-2.08 (2 H, m), 1.74-1.93 (7 H, m), 1.53-1.74 (3 H, m).

Example 6

Preparation of 4-({3-[(4-cyclobutyl-1,4-diazepan-1-yl)carbonyl]azetidin-1-yl}carbonyl)benzonitrile. Potency Range A

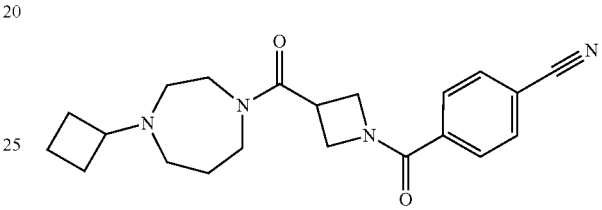

In a similar fashion (Route 3, GP D), 4-cyanobenzoic acid (18.5 mg, 0.13 mmol) and 1-(azetidin-3-ylcarbonyl)-4-cyclobutyl-1,4-diazepane (30 mg, 0.13 mmol) gave the title compound (15 mg, 34% yield) as viscous orange brown oil.

LCMS data: Calculated MH$^+$ (366). Found 99% (WO m/z 366, Rt=3.58 min (Method D).

NMR data: $^1$H NMR (500 MHz, CHLOROFORM-d) δ ppm 7.71-7.77 (4 H, m), 4.72 (1 H, m), 4.38-4.47 (1 H, m), 4.32 (2 H, m), 3.58-3.75 (3 H, m), 3.35-3.40 (2 H, m), 2.83-2.91 (1 H, m), 2.34-2.58 (4 H, m), 2.04 (2 H, m), 1.74-1.94 (5 H, m), 1.56-1.73 (2H, m).

Example 7

Preparation of methyl 5-({3-[(4-cyclobutyl-1,4-diazepan-1-yl)carbonyl]azetidin-1-yl}carbonyl)pyridine-2-carboxylate. Potency Range A

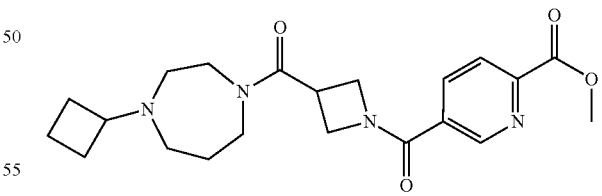

In a similar fashion (Route 3, GP D), 6-(methoxycarbonyl)pyridine-3-carboxylic acid (200 mg, 1.10 mmol) and 1-(azetidin-3-ylcarbonyl)-4-cyclobutyl-1,4-diazepane (262 mg, 1.10 mmol) gave the title compound (173 mg, 39% yield) as white solid.

LCMS data: Calculated MH$^+$ (401). Found 100% (MH$^+$) m/z 401, Rt=3.31 min (Method D).

NMR data: $^1$H NMR (500 MHz, CHLOROFORM-d) δ ppm 8.96 (1 H, m), 8.18-8.27 (1 H, m), 8.09-8.18 (1 H, m), 4.74 (1 H, m), 4.27-4.50 (3 H, m), 4.03 (3 H, s), 3.57-3.75 (3

H, m), 3.32-3.43 (2 H, m), 2.87 (1 H, s), 2.47-2.57 (2 H, m), 2.42 (2 H, m), 1.98-2.10 (2 H, m), 1.76-1.93 (4 H, m), 1.57-1.72 (2 H, m).

Route 4

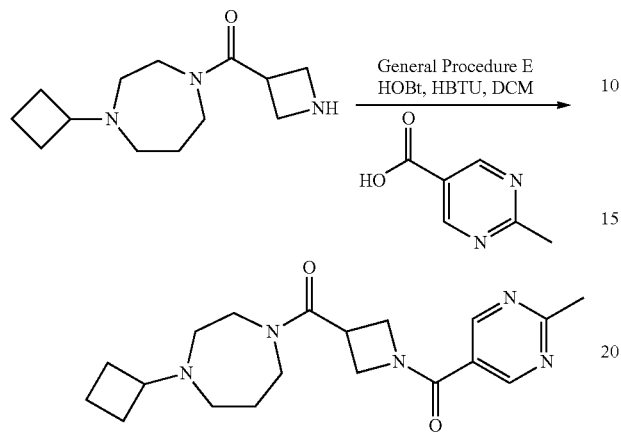

General Procedure E:

Example 8

Preparation of 1-cyclobutyl-4-({1-[(2-methylpyrimidin-5-yl)carbonyl]azetidin-3-yl}carbonyl)-1,4-diazepane. Potency Range A

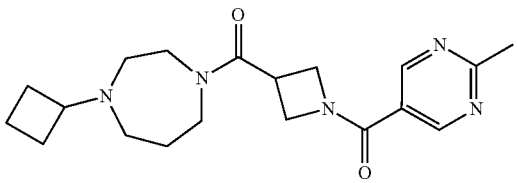 [SMILES: Cc1ncc(C(=O)N2CC(C(=O)N3CCCN(C4CCC4)CC3)C2)cn1]

To a stirred solution of 2-methylpyrimidine-5-carboxylic acid (23 mg, 0.17 mmol) in DCM (3 ml) was added HOBt (23 mg, 0.17 mmol) and HBTU (64 mg, 0.17 mmol). After 3 hours, a solution of 1-(Azetidin-3-ylcarbonyl)-4-cyclobutyl-1,4-diazepane (48 mg, 0.17 mmol), in DCM (1 ml) was added and the yellow suspension gradually dissolved to give a yellow solution. The reaction mixture was quenched with saturated NaHCO$_3$ (1 ml) and the aqueous layer extracted with DCM (3×5 ml). The combined organic layers were dried (MgSO$_4$), filtered and concentrated at reduced pressure. Purification by silica FCC (eluting with 99:1 to 95:5 gradient of DCM/2M NH$_3$ in MeOH) gave the title compound (17.4 mg, 29% yield) as pale yellow oil.

LCMS data: Calculated MH$^+$ (358). Found 99% (MH$^+$) m/z 358, Rt=3.05 min (Method D).

NMR data: $^1$H NMR (500 MHz, CHLOROFORM-d) δ ppm 8.89 (2 H, m), 4.77 (1 H, m), 4.36-4.44 (2 H, m), 4.27-4.34 (1 H, m), 3.58-3.72 (3 H, m), 3.33-3.38 (2 H, m), 2.85 (1 H, m), 2.77 (3 H, s), 2.46-2.52 (2 H, m), 2.37-2.43 (2 H, m), 2.02 (2 H, m), 1.87 (1 H, m), 1.74-1.84 (3 H, m), 1.58-1.70 (2 H, m).

The following compounds were prepared as described in Route 4, General Procedure E above.

Example 9

Preparation of 1-cyclobutyl-4-({1-[(5-methylpyrazin-2-yl)carbonyl]azetidin-3-yl}carbonyl)-1,4-diazepane. Potency Range A

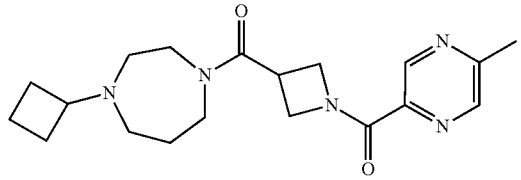 [SMILES: Cc1cnc(C(=O)N2CC(C(=O)N3CCCN(C4CCC4)CC3)C2)cn1]

In a similar fashion (Route 4, GP E), 5-methylpyrazine-2-carboxylic acid (23 mg, 0.17 mmol) and 1-(azetidin-3-ylcarbonyl)-4-cyclobutyl-1,4-diazepane (40 mg, 0.17 mmol) gave the title compound (22 mg, 34% yield) as pale yellow oil.

LCMS data: Calculated MH$^+$ (358). Found 98% (MH$^+$) m/z 358, Rt=2.05 min (Method D).

NMR data: $^1$H NMR (500 MHz, CHLOROFORM-d) δ ppm 9.15 (1 H, s), 8.37 (1 H, s), 4.92 (1 H, m), 4.82 (1 H, m), 4.32-4.45 (2 H, m), 3.57-3.75 (3 H, m), 3.33-3.42 (2 H, m), 2.86 (1 H, m), 2.60 (3 H, s), 2.33-2.57 (4 H, m), 2.11-2.31 (1 H, m), 1.97-2.08 (2 H, m), 1.87-1.94 (1 H, m), 1.74-1.87 (3 H, m), 1.61 (2 H, m).

Example 10

Preparation of 1-cyclobutyl-4-({1-[(6-methylpyridin-3-yl)carbonyl]azetidin-3-yl}carbonyl)-1,4-diazepane. Potency Range A

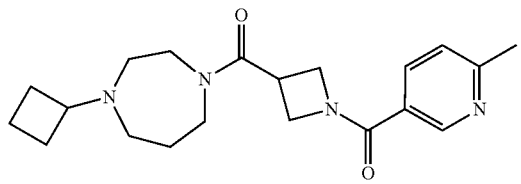 [SMILES: Cc1ccc(C(=O)N2CC(C(=O)N3CCCN(C4CCC4)CC3)C2)cn1]

In a similar fashion (Route 4, GP E), 6-methylpyridine-3-carboxylic acid (200 mg, 1.46 mmol) and 1-(azetidin-3-ylcarbonyl)-4-cyclobutyl-1,4-diazepane (0.346 mg, 1.46 mmol) gave the title compound (219 mg, 42% yield) as white solid.

LCMS data: Calculated MH$^+$ (357). Found 100% (WO m/z 357, RT=3.34 min (Method D).

NMR data: $^1$H NMR (500 MHz, CHLOROFORM-d) δ ppm 8.76 (1 H, d, J=1.8 Hz), 7.90 (1 H, dd, J=8.1, 2.0 Hz), 7.23 (1 H, d, J=8.1 Hz), 4.75 (1 H, m), 4.35-4.46 (2 H, m), 4.28-4.36 (1 H, m), 3.59-3.74 (3 H, m), 3.33-3.42 (2 H, m), 2.82-2.92 (1 H, m), 2.61 (3 H, s), 2.48-2.54 (2 H, m), 2.39-2.46 (2 H, m), 2.00-2.10 (2 H, m), 1.74-1.93 (4 H, m), 1.58-1.74 (2 H, m).

Example 11

Preparation of 1-cyclobutyl-4-[(1-{[4-(tetrahydro-2H-pyran-4-yloxy)phenyl]carbonyl}azetidin-3-yl)carbonyl]-1,4-diazepane. Potency Range A

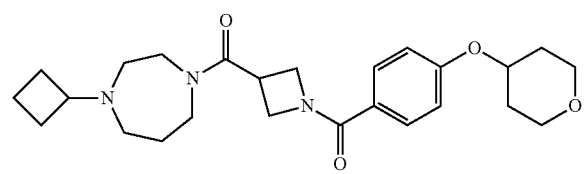 [SMILES: O=C(c1ccc(OC2CCOCC2)cc1)N1CC(C(=O)N2CCCN(C3CCC3)CC2)C1]

In a similar fashion (Route 4, GP E) 4-(tetrahydropyran-4-yloxy)benzoic acid (50 mg, 0.23 mmol) and 1-(azetidin-3-ylcarbonyl)-4-cyclobutyl-1,4-diazepane (53 mg, 0.23 mmol) gave the title compound (57 mg, 57%).

LCMS data: Calculated MH$^+$ (442). Found 97% (MH$^+$) m/z 442, Rt=2.79 min (Method C).

NMR data: $^1$H NMR (500 MHz, CHLOROFORM-d) δ ppm 7.63 (2 H, d, J=8.7 Hz), 6.92 (2 H, d, J=8.9 Hz), 4.70-4.85 (1 H, m), 4.50-4.64 (1 H, m), 4.20-4.47 (3 H, m), 3.93-4.06 (2 H, m), 3.54-3.78 (5 H, m), 3.30-3.44 (2 H, m), 2.80-2.95 (1 H, m), 2.32-2.62 (4H, m), 1.97-2.12 (4 H, m), 1.74-1.96 (6 H, m), 1.60-1.74 (2 H, m).

Example 12

Preparation of 1-cyclobutyl-4-[(1-{[6-(1H-imidazol-1-yl)pyridin-3-yl]carbonyl}azetidin-3-yl)carbonyl]-1,4-diazepane. Potency Range A

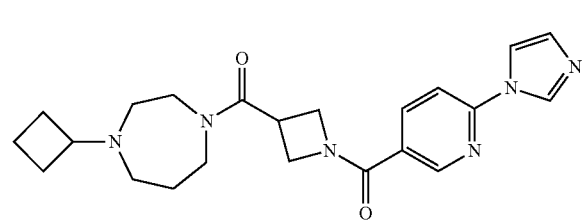 [SMILES: O=C(c1ccc(-n2ccnc2)nc1)N1CC(C(=O)N2CCCN(C3CCC3)CC2)C1]

In a similar fashion (Route 4 GP E) 6-(1H-imidazol-1-yl)nicotinic acid (26 mg, 0.14 mmol) and 1-(azetidin-3-ylcarbonyl)-4-cyclobutyl-1,4-diazepane (30 mg, 0.13 mmol) gave the title compound (16 mg, 31%).

LCMS data: Calculated MH$^+$ (409). Found 100% (MH$^+$) m/z 409, Rt=3.38 min (Method D).

NMR data: $^1$H NMR (500 MHz, CHLOROFORM-d) δ ppm 8.75 (1H, d, J=1.7 Hz), 8.41 (1 H, s), 8.17 (1H, dd, J=8.5, 1.2 Hz), 7.68 (1H, s), 7.43 (1H, d, J=8.5 Hz), 7.23 (1H, s), 4.83 (1H, m.), 4.40-4.51 (2H, m), 4.27-4.39 (1H, m), 3.56-3.79 (3H, m), 3.40 (2H, m.), 2.82-2.96 (1H, m), 2.53 (4H, m.), 2.04-2.11 (2H, m), 1.49-1.99 (6H, m).

Example 13

Preparation of 1-cyclobutyl-4-[(1-{[6-(1H-1,2,4-triazol-1-yl)pyridin-3-yl]carbonyl}azetidin-3-yl)carbonyl]-1,4-diazepane. Potency Range A

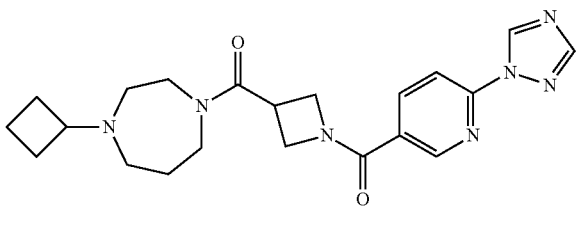 [SMILES: O=C(c1ccc(-n2cncn2)nc1)N1CC(C(=O)N2CCCN(C3CCC3)CC2)C1]

In a similar fashion (Route 4, GP E), 6-(1H-1,2,4-triazol-1-yl)nicotinic acid (26 mg, 0.14 mmol) and 1-(azetidin-3-ylcarbonyl)-4-cyclobutyl-1,4-diazepane (30 mg, 0.13 mmol) gave the title compound (16 mg, 31%).

LCMS data: Calculated MH$^+$ (410). Found 100% (MH$^+$) m/z 410, Rt=3.46 min (Method D).

$^1$H NMR (500 MHz, MeOD) δ ppm 9.42 (1H, s), 8.81 (1H, d, J=2.0 Hz), 8.31 (1H, dd, J=8.5, 2.2 Hz), 8.24 (1H, s), 8.05 (1H, d, J=8.5 Hz), 4.62 (2H, m), 4.38-4.52 (1 H, m), 4.23-4.38 (1 H, m), 3.85-4.02 (1 H, m), 3.60-3.75 (2 H, m), 3.40-3.57 (2 H, m), 2.84-3.02 (1 H, m), 2.52-2.71 (2 H, m), 2.39-2.51 (2 H, m), 2.01-2.16 (2 H, m), 1.77-1.96 (4 H, m), 1.56-1.77 (2 H, m).

Example 14

Preparation of 1-cyclobutyl-4-[(1-{[6-(1H-pyrazol-1-yl)pyridin-3-yl]carbonyl}azetidin-3-yl)carbonyl]-1,4-diazepane. Potency Range A

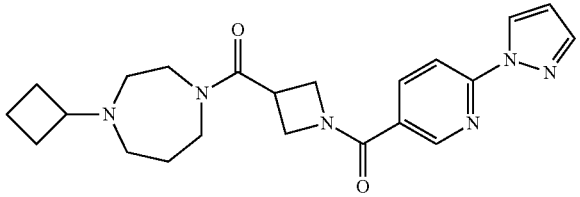 [SMILES: O=C(c1ccc(-n2cccn2)nc1)N1CC(C(=O)N2CCCN(C3CCC3)CC2)C1]

In a similar fashion (Route 4 GP E), 6-(1H-Pyrazol-1-yl)nicotinic acid (50 mg, 0.26 mmol) and 1-(azetidin-3-ylcarbonyl)-4-cyclobutyl-1,4-diazepane (57 mg, 0.24 mmol) gave the title compound (4.7 mg, 5%) after preparative HPLC (Method 2).

LCMS data: Calculated MH$^+$ (409). Found 98% (MH$^+$) m/z 409, Rt=4.02 min (Method D).

NMR data: $^1$H NMR (500 MHz, MeOD) δ ppm 8.74 (1 H, d, J=1.8 Hz), 8.66 (1 H, d, J=2.7 Hz), 8.21 (1 H, dd, J=8.5, 2.3 Hz), 8.04 (1 H, d, J=8.7 Hz), 7.80 (1 H, s), 6.50-6.63 (1 H, m), 4.62 (2 H, d, J=7.3 Hz), 4.37-4.48 (1 H, m), 4.28-4.37 (1 H, m), 3.83-3.99 (1 H, m), 3.60-3.74 (2 H, m), 3.43-3.55 (2 H, m), 2.84-3.03 (1 H, m), 2.41-2.63 (4 H, m), 2.01-2.13 (2 H, m), 1.79-1.97 (4 H, m), 1.57-1.76 (2 H, m).

Route 5

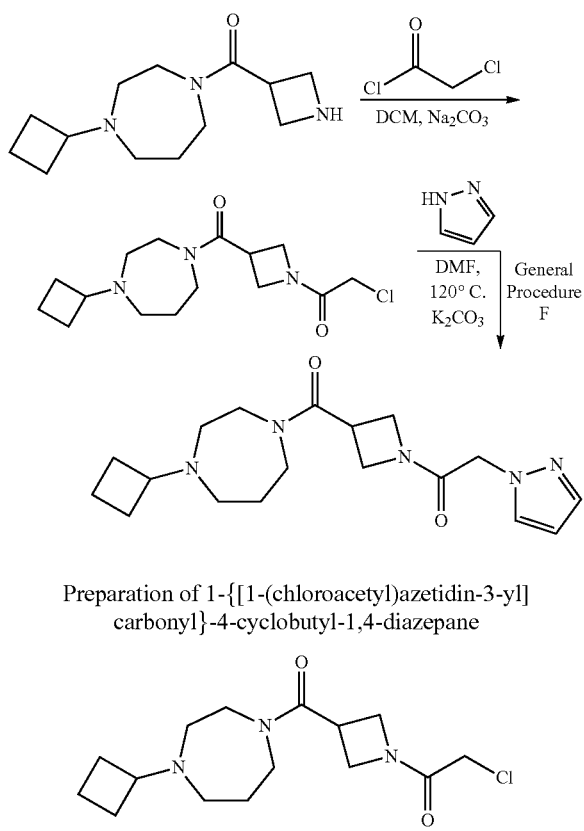

Preparation of 1-{[1-(chloroacetyl)azetidin-3-yl]carbonyl}-4-cyclobutyl-1,4-diazepane

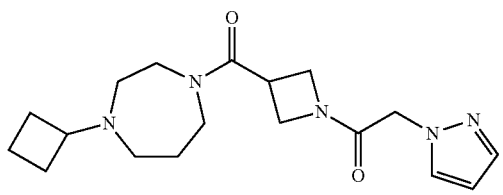 [SMILES: O=C(Cn1cccn1)N1CC(C(=O)N2CCCN(C3CCC3)CC2)C1]

To a solution of 1-(azetidin-3-ylcarbonyl)-4-cyclobutyl-1,4-diazepane (330 mg, 1.39 mmol) and Na$_2$CO$_3$ (590 mg, 5.56 mmol) in dichloromethane (10 ml) at 0° C. was added chloroacetyl chloride (107 μl, 1.39 mmol). After 10 mins the reaction temperature was raised to RT and stirred for a further hour. The reaction was then filtered and concentrated at reduced pressure to give the title compound as colourless oil (411 mg, 91% yield), which was used without further purification.

LCMS data: Calculated MH$^+$ (314). Found 81% (MH$^+$) m/z 314, Rt=3.38 min.

NMR data: $^1$H NMR (500 MHz, CDCl$_3$) δ ppm 4.54-4.65 (1 H, m), 4.25-4.37 (1 H, m), 4.06-4.24 (2 H, m), 3.77-3.89 (2 H, m), 3.47-3.76 (3 H, m), 3.20-3.37 (2 H, m), 2.74-2.89 (1 H, m), 2.28-2.59 (4 H, m), 1.70-2.04 (6 H, m), 1.49-1.68 (2 H, m).

General Procedure F:

Example 15

Preparation of 1-cyclobutyl-4-{[1-(1H-pyrazol-1-ylacetyl)azetidin-3-yl]carbonyl}-1,4-diazepane. Potency Range A

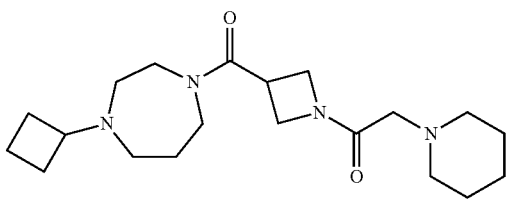 [SMILES: O=C(CN1CCCCC1)N1CC(C(=O)N2CCCN(C3CCC3)CC2)C1]

A solution of 1-{[1-(chloroacetyl)azetidin-3-yl]carbonyl}-4-cyclobutyl-1,4-diazepane (40 mg, 0.13 mol), K$_2$CO$_3$ (20 mg, 0.14 mmol) and pyrazole (9 mg, 0.13 mmol) was heated at 120° C. in DMF (2 ml) in a sealed tube for 16 hrs. The solvent was evaporated at reduced pressure and purified by silica FCC (using a gradient of eluents; DCM/MeOH/NH$_3$ 99:1:1 to 92:8:1) to give the title compound (18 mg, 40% yield) as pale brown oil.

LCMS data: Calculated MH$^+$ (346). Found 79% (MH$^+$) m/z 346, Rt=3.23 min (Method D).

NMR data—estimated ~90% purity: $^1$H NMR (500 MHz, CDCl$_3$) δ ppm 7.49-7.58 (2 H, m), 6.32 (1 H, m), 4.70-4.88 (2 H, m), 4.29-4.39 (1 H, m), 4.11-4.28 (2 H, m), 3.95-4.09 (1 H, m), 3.45-3.72 (3 H, m), 3.25-3.38 (2 H, m), 2.79-2.92 (1 H, m), 2.30-2.57 (4 H, m), 2.03 (2 H, m), 1.72-1.96 (4 H, m), 1.54-1.72 (2 H, m).

Route 6

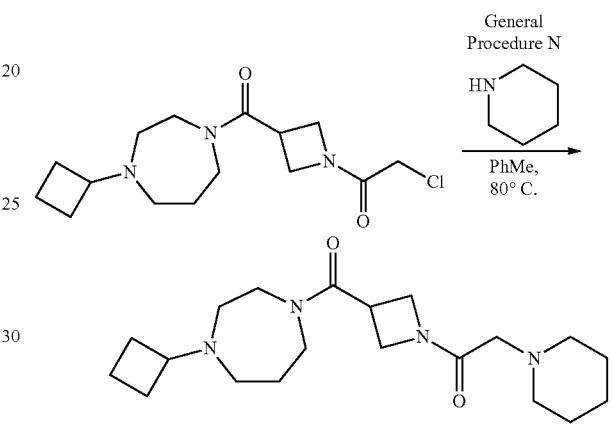

General Procedure N:

Example 16

Preparation of 1-cyclobutyl-4-{[1-(piperidin-1-ylacetyl)azetidin-3-yl]carbonyl}-1,4-diazepane. Potency Range A A solution of 1-{[1-(chloroacetyl)azetidin-3-yl]carbonyl}-4-cyclobutyl-1,4-diazepane (40 mg, 0.13 mmol) and piperidine (38 μl, 0.38 mmol) in toluene (2 ml) was heated at 80° C. for 4 hrs in a sealed tube then cooled to RT. The reaction was diluted with DCM (30 ml), washed with a saturated aqueous solution of NaHCO$_3$ (2×15 ml), dried (MgSO$_4$), filtered and concentrated at reduced pressure. The residue was purified by silica FCC (using a gradient of eluents; DCM/MeOH/NH$_3$ 99:1:1 to 92:8:1) to give the title compound (25 mg, 53% yield) as a colourless oil.

LCMS data: Calculated MH$^+$ (363). Found 85% (MH$^+$) m/z 363, Rt=3.74 min (Method D).

NMR data: $^1$H NMR (500 MHz, CDCl$_3$) δ ppm 4.55-4.65 (1 H, m), 4.30-4.40 (1 H, m), 4.06-4.24 (2 H, m), 3.47-3.73 (3

H, m), 3.28-3.40 (2 H, m), 2.92-3.06 (2 H, m), 2.80-2.90 (1 H, m), 2.30-2.58 (8 H, m), 1.98-2.08 (2 H, m), 1.73-1.93 (4 H, m), 1.50-1.73 (6 H, m), 1.34-1.46 (2 H, m).

The following compound was prepared as described in Route 6, General Procedure N above.

Example 17

Preparation of 1-cyclobutyl-4-{[1-(morpholin-4-ylacetyl)azetidin-3-yl]carbonyl}-1,4-diazepane. Potency Range A

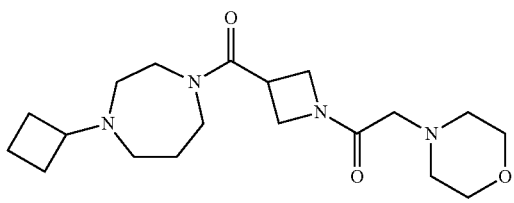 [SMILES: O=C(CN1CCOCC1)N1CC(C(=O)N2CCCN(C3CCC3)CC2)C1]

In a similar fashion (Route 6, GP N), 1-{[1-(chloroacetyl)azetidin-3-yl]carbonyl}-4-cyclobutyl-1,4-diazepane (100 mg, 0.32 mmol) and morpholine (83 mg, 0.95 mmol) gave the title compound (8.8 mg, 8%) as a colourless oil after purification by preparative HPLC (Method 2).

LCMS data: Calculated MH$^+$ (365). Found 99% (MH$^+$) m/z 365, Rt=3.06 min (Method D).

NMR data: $^1$H NMR (500 MHz, MeOD) δ ppm 4.43-4.51 (2 H, m), 4.15-4.23 (1 H, m), 4.06-4.15 (1 H, m), 3.77-3.87 (1 H, m), 3.67-3.73 (4 H, m), 3.58-3.67 (2 H, m), 3.41-3.51 (2 H, m), 3.07 (2 H, s), 2.87-3.00 (1 H, m), 2.41-2.63 (8 H, m), 2.02-2.13 (2 H, m), 1.78-1.95 (4 H, m), 1.61-1.76 (2 H, m).

Example 18

Preparation of 1-cyclobutyl-4-({1-[(1,1-dioxidothiomorpholin-4-yl)acetyl]azetidin-3-yl}carbonyl)-1,4-diazepane. Potency Range A

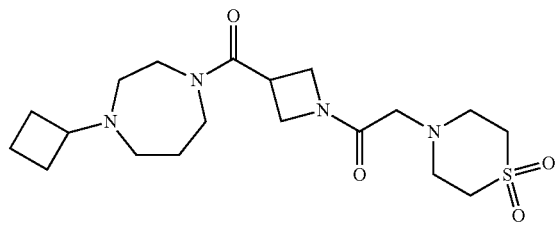 [SMILES: O=C(CN1CCS(=O)(=O)CC1)N1CC(C(=O)N2CCCN(C3CCC3)CC2)C1]

In a similar fashion (Route 6, GP N), 1-{[1-(chloroacetyl)azetidin-3-yl]carbonyl}-4-cyclobutyl-1,4-diazepane (150 mg, 0.47 mmol) and thiomorpholine-1,1-dioxide (130 mg, 0.75 mmol) gave the title compound (7.9 mg, 3%) as a colourless oil after purification by preparative HPLC (Method 2).

LCMS data: Calculated MH$^+$ (413). Found 100% (MH$^+$) m/z 413, Rt=3.00 min (Method D).

NMR data: $^1$H NMR (500 MHz, MeOD) δ ppm 4.37-4.54 (2 H, m), 4.16-4.27 (1 H, m), 4.07-4.15 (1 H, m), 3.69-3.89 (2 H, m), 2.67-3.69 (18 H, m), 2.16-2.32 (2 H, m), 1.89-2.16 (4 H, m), 1.67-1.87 (2 H, m).

Example 19

Preparation of 1-cyclobutyl-4-({1-[(3,3-difluoropyrrolidin-1-yl)acetyl]azetidin-3-yl}carbonyl)-1,4-diazepane. Potency Range A

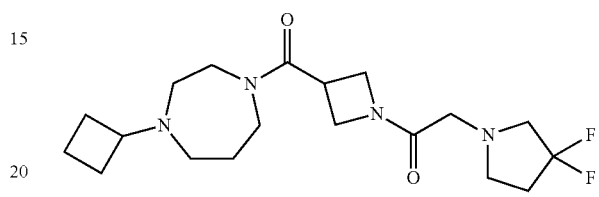

In a similar fashion (Route 6, GP N), 1-{[1-(chloroacetyl)azetidin-3-yl]carbonyl}-4-cyclobutyl-1,4-diazepane (150 mg, 0.47 mmol) and 3,3-difluoropyrrolidine hydrochloride (111 mg, 0.75 mmol) gave the title compound (6.3 mg, 3%) as colourless oil after purification by preparative HPLC (Method 2).

LCMS data: Calculated MH$^+$ (385). Found 100% (MH$^+$) m/z 385, Rt=3.56 min (Method D).

NMR data: $^1$H NMR (500 MHz, MeOD) δ ppm 4.37-4.52 (2 H, m), 4.04-4.30 (3 H, m), 3.65-3.91 (3 H, m), 3.37-3.65 (4 H, m), 3.28-3.37 (2 H, m), 2.83-3.19 (6 H, m), 2.08-2.43 (8 H, m), 1.69-1.93 (2 H, m).

Example 20

Preparation of 1-cyclobutyl-4-({1-[(4,4-difluoropiperidin-1-yl)acetyl]azetidin-3-yl}carbonyl)-1,4-diazepane. Potency Range A

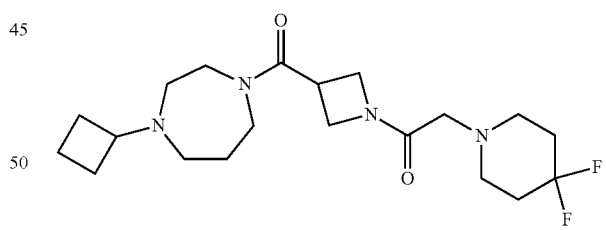

In a similar fashion (Route 6, GP N), 1-{[1-(chloroacetyl)azetidin-3-yl]carbonyl}-4-cyclobutyl-1,4-diazepane (150 mg, 0.47 mmol) and 4,4-difluoropiperidine hydrochloride (90 mg, 0.57 mmol) gave the title compound (7.3 mg, 4%) as colourless oil after purification by preparative HPLC (Method 2).

LCMS data: Calculated MH$^+$ (399). Found 90% (MH$^+$) m/z 399, Rt=3.68 min (Method D).

NMR data: $^1$H NMR (500 MHz, CHLOROFORM-d) δ ppm 4.63 (1 H, m), 4.17-4.34 (2 H, m), 4.06-4.17 (1 H, m), 3.51-3.77 (3 H, m), 3.29-3.43 (2 H, m), 3.04-3.13 (2 H, m), 2.81-2.93 (1 H, m), 2.35-2.77 (8 H, m), 1.75-2.14 (10 H, m), 1.55-1.75 (2 H, m).

Route 7

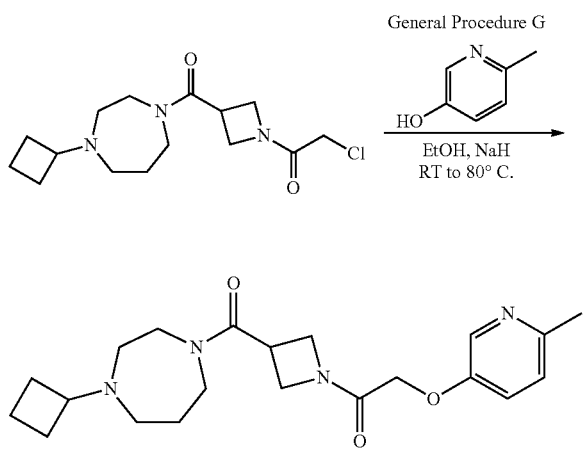

General Procedure G:

Example 21

Preparation of 1-cyclobutyl-4-[(1-{[(6-methylpyridin-3-yl)oxy]acetyl}azetidin-3-yl)carbonyl]-1,4-diazepane. Potency Range A

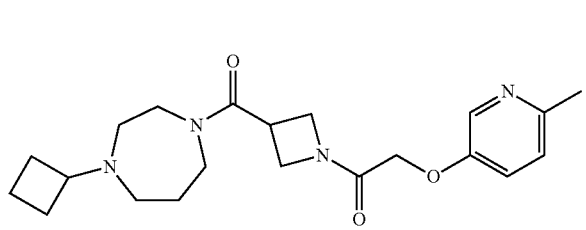 [SMILES: Cc1ccc(OCC(=O)N2CC(C(=O)N3CCCN(C4CCC4)CC3)C2)cn1]

To a stirred solution of 3-hydroxy-6-methylpyridine (28 mg, 0.26 mmol) in EtOH (1 ml) was added NaH (8 mg of a 60% dispersion in mineral oil, 0.19 mmol). When evolution of gas had ceased the solution was added to 1-{[1-(chloroacetyl)azetidin-3-yl]carbonyl}-4-cyclobutyl-1,4-diazepane (40 mg, 0.13 mmol) in EtOH (1 ml) at RT and the reaction was then heated at 80° C. in a sealed tube for 4 hrs. After cooling to RT and quenching with water (1 ml), the mixture was diluted with DCM (30 ml) and washed with a saturated solution of NaHCO$_3$ (2×15 ml), dried (MgSO$_4$), filtered and concentrated at reduced pressure. The residue was purified by silica FCC (using a gradient of eluents; DCM/MeOH/NH$_3$ 99:1:1 to 90:10:1) to give the title compound (18 mg, 36% yield) as colourless oil.

LCMS data: Calculated MH$^+$ (387). Found 94% (MH$^+$) m/z 387, Rt=3.50 min (Method D).

NMR data: $^1$H NMR (500 MHz, CDCl$_3$) δ ppm 8.19 (1 H, d, J=2.7 Hz), 7.04-7.16 (2 H, m), 4.64-4.74 (1 H, m), 4.52-4.63 (2 H, m), 4.35-4.43 (1 H, m), 4.14-4.29 (2 H, m), 3.53-3.72 (3 H, m), 3.24-3.40 (2 H, m), 2.77-2.90 (1 H, m), 2.29-2.57 (7 H, m), 1.95-2.08 (2 H, m), 1.71-1.94 (4 H, m), 1.52-1.71 (2 H, m).

The following compound was prepared as described in Route 7, General Procedure G above.

Example 22

Preparation of 4-(2-{3-[(4-cyclobutyl-1,4-diazepan-1-yl)carbonyl]azetidin-1-yl}-2-oxoethoxy)benzonitrile. Potency Range A

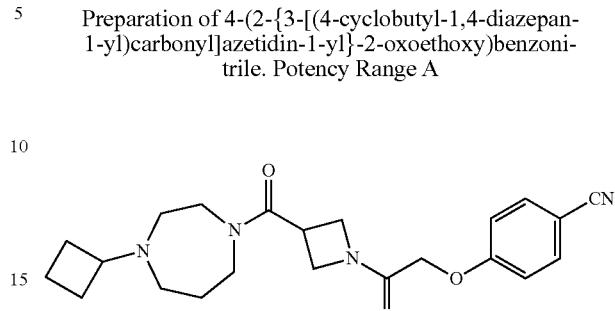

In a similar fashion (Route 7, GP G), 4-cyanophenol (30 mg, 0.26 mmol) and 1-{[1-(chloroacetyl)azetidin-3-yl]carbonyl}-4-cyclobutyl-1,4-diazepane (40 mg, 0.13 mmol) gave the title compound (5 mg, 10% yield) as colourless oil after purification by preparative HPLC.

LCMS data: Calculated MH$^+$ (397). Found 99% (MH$^+$) m/z 397, Rt=3.82 min. (Method D).

NMR data: $^1$H NMR (500 MHz, CDCl$_3$) δ ppm 7.69 (2 H, d, J=8.9 Hz), 7.11 (2 H, d, J=8.9 Hz), 4.74 (2 H, s), 4.45-4.56 (2 H, m), 4.20-4.29 (1 H, m), 4.14-4.20 (1 H, m), 3.81-3.91 (1 H, m), 3.56-3.76 (2 H, m), 3.42-3.52 (2 H, m), 2.97-3.21 (1 H, m), 2.48-2.82 (4 H, m), 2.06-2.21 (2 H, m), 1.82-2.02 (4 H, m), 1.62-1.80 (2 H, m).

Route 8

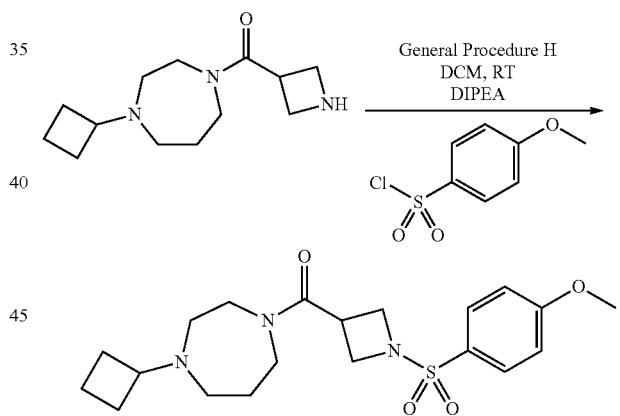

General Procedure H:

Example 23

Preparation of 1-cyclobutyl-4-({1-[(4-methoxyphenyl)sulfonyl]azetidin-3-yl}carbonyl)-1,4-diazepane. Potency Range B

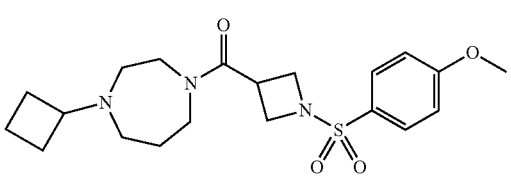 [SMILES: COc1ccc(S(=O)(=O)N2CC(C(=O)N3CCCN(C4CCC4)CC3)C2)cc1]

To a stirred solution of 1-(azetidin-3-ylcarbonyl)-4-cyclobutyl-1,4-diazepane (40 mg, 0.169 mmol) in DCM (4 ml) was added DIPEA (0.056 ml, 0.34 mmol) and 4-methoxybenzenesulfonyl chloride (38 mg, 0.185 mmol) at RT. After stirring for 16 hrs at RT the reaction was quenched by addition of MeOH (0.5 ml) and the solvent removed at reduced pressure. Purification by preparative HPLC (Method 1) provided the TFA salt in ~90% purity by $^1$H NMR. Re-purification by silica FCC (using a gradient of eluents; DCM/MeOH/NH$_3$ 98:2:0.5 to 95:5:0.5) gave the title compound (25 mg, 36% yield) as colourless oil.

LCMS data: Calculated MH$^+$ (408). Found 99% (MH$^+$) m/z 408, Rt=4.20 min (Method D).

$^1$H NMR (500 MHz, MeOD) δ ppm 7.69-7.91 (2 H, m), 7.17 (2 H, d, J=8.9 Hz), 3.82-3.99 (7 H, m), 3.55-3.68 (1 H, m), 3.45-3.53 (2 H, m), 3.32 (3 H, s), 2.89 (1 H, m), 2.48-2.54 (1 H, m), 2.43-2.47 (1 H, m), 2.37-2.43 (2 H, m), 1.99-2.13 (2 H, m), 1.77-1.89 (3 H, m), 1.75 (1 H, dt, J=11.6, 5.8 Hz), 1.59-1.71 (2H, m).

The following compounds were prepared as described in Route 8, General Procedure H above.

Example 24

Preparation of 1-cyclobutyl-4-{[1-(cyclohexylsulfonyl)azetidin-3-yl]carbonyl}-1,4-diazepane. Potency Range A

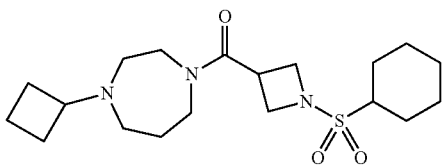 [SMILES: O=C(C1CN(S(=O)(=O)C2CCCCC2)C1)N1CCCN(C2CCC2)CC1]

In a similar fashion (Route 8, GP H), 1-(azetidin-3-ylcarbonyl)-4-cyclobutyl-1,4-diazepane (50 mg, 0.21 mmol) and cyclohexanesulfonyl chloride (42.3 mg, 0.23 mmol) gave the title compound (32 mg, 40% yield) as colourless oil.

LCMS data: Calculated MH$^+$ (384). Found 99% (MH$^+$) m/z 384, Rt=4.44 min (Method D).

$^1$H NMR (500 MHz, MeOD) δ ppm 4.17 (2 H, m), 4.03 (2 H, m), 3.74-3.82 (1 H, m), 3.58-3.67 (2 H, m), 3.39-3.47 (2 H, m), 2.87-3.00 (2 H, m), 2.55 (2 H, m), 2.47 (2 H, m), 2.02-2.18 (4 H, m), 1.78-1.94 (6 H, m), 1.60-1.76 (3 H, m), 1.40-1.52 (2 H, m), 1.34 (2 H, m), 1.17-1.26 (1 H, m).

Example 25

Preparation of 1-cyclobutyl-4-({1-[(cyclopentylmethyl)sulfonyl]azetidin-3-yl}carbonyl)-1,4-diazepane. Potency Range A

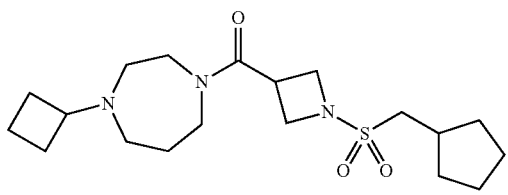 [SMILES: O=C(C1CN(S(=O)(=O)CC2CCCC2)C1)N1CCCN(C2CCC2)CC1]

In a similar fashion (Route 8, GP H), 1-(azetidin-3-ylcarbonyl)-4-cyclobutyl-1,4-diazepane (50 mg, 0.21 mmol) and cyclopentylmethanesulfonyl chloride (42.3 mg, 0.23 mmol) gave the title compound (26 mg, 32% yield) as colourless oil.

LCMS data: Calculated MH$^+$ (384). Found 98% (MH$^+$) m/z 384, Rt=4.47 min (Method D).

$^1$H NMR (500 MHz, MeOD) δ ppm 4.15 (2 H, m), 4.05 (2 H, m), 3.75-3.82 (1 H, m), 3.59-3.65 (2 H, m), 3.41-3.46 (2 H, m), 3.11 (2 H, m), 2.93 (1 H, m), 2.52-2.58 (2 H, m), 2.44-2.50 (2 H, m), 2.27-2.37 (1 H, m), 2.04-2.12 (2 H, m), 1.93-2.01 (2 H, m), 1.81-1.91 (4 H, m), 1.65-1.74 (4 H, m), 1.55-1.64 (2 H, m).

Example 26

Preparation of 1-cyclobutyl-4-{[1-(phenylsulfonyl)azetidin-3-yl]carbonyl}-1,4-diazepane. Potency Range A

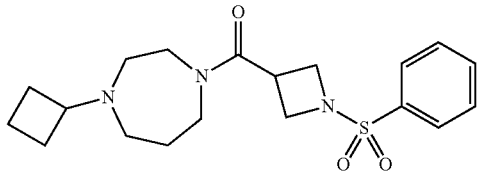 [SMILES: O=C(C1CN(S(=O)(=O)c2ccccc2)C1)N1CCCN(C2CCC2)CC1]

In a similar fashion (Route 8, GP H), 1-(azetidin-3-ylcarbonyl)-4-cyclobutyl-1,4-diazepane (50 mg, 0.21 mmol) and benzenesulfonyl chloride (40.9 mg, 0.23 mmol) gave the title compound (18 mg, 23% yield) as colourless oil.

LCMS data: Calculated MH$^+$ (378). Found 98% (MH$^+$) m/z 378, Rt=4.15 min (Method D).

$^1$H NMR (500 MHz, MeOD) δ ppm 7.83-7.91 (2 H, m), 7.71-7.78 (1 H, m), 7.65-7.70 (2 H, m), 3.95-4.01 (2 H, m), 3.92 (2 H, m), 3.57-3.66 (1 H, m), 3.45-3.51 (2 H, m), 3.33-3.35 (1 H, m), 3.32 (2 H, m), 2.83-2.95 (1 H, m), 2.48-2.51 (1 H, m), 2.42-2.46 (1 H, m), 2.40 (2 H, m), 2.01-2.10 (2 H, m), 1.78-1.87 (3 H, m), 1.60-1.76 (3 H, m).

Example 27

Preparation of 4-({3-[(4-cyclobutyl-1,4-diazepan-1-yl)carbonyl]azetidin-1-yl}sulfonyl)benzonitrile. Potency Range A

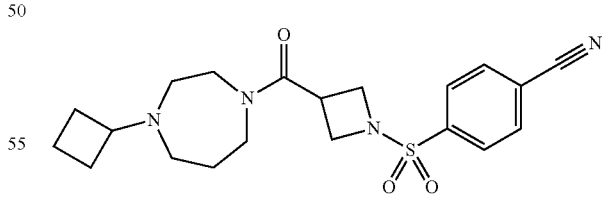

In a similar fashion (Route 8, GP H), 1-(azetidin-3-ylcarbonyl)-4-cyclobutyl-1,4-diazepane (50 mg, 0.21 mmol) and 4-cyanobenzenesulfonyl chloride (46.7 mg, 0.23 mmol) gave the title compound (45 mg, 53% yield) as colourless oil.

LCMS data: Calculated MH$^+$ (403). Found 100% (MH$^+$) m/z 403, Rt=4.17 min (Method D).

$^1$H NMR (500 MHz, MeOD) δ ppm 7.99-8.08 (4 H, m), 4.01-4.08 (2 H, m), 3.95 (2 H, m), 3.66 (1 H, m), 3.45-3.51 (2 H, m), 3.33-3.38 (2 H, m), 2.84-2.96 (1 H, m), 2.48-2.53 (1 H, m), 2.43-2.46 (1 H, m), 2.38-2.43 (2 H, m), 2.02-2.11 (2 H, m), 1.78-1.87 (3 H, m), 1.75 (1 H, m), 1.60-1.71 (2 H, m).

Route 9

General Procedure I

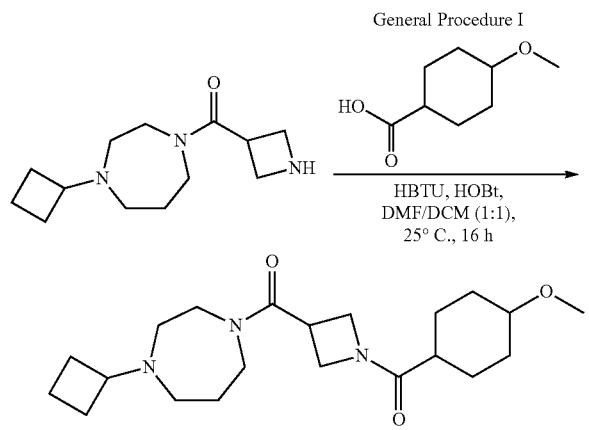

General Procedure I:

Example 28

Preparation of 1-cyclobutyl-4-({1-[(4-methoxycyclohexyl)carbonyl]azetidin-3-yl}carbonyl)-1,4-diazepane. Potency Range A

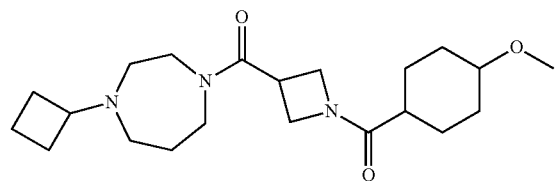 [SMILES: COC1CCC(C(=O)N2CC(C(=O)N3CCCN(C4CCC4)CC3)C2)CC1]

To a stirred solution of 4-methoxycyclohexane carboxylic acid (20 mg, 0.13 mmol) in DMF/DCM (1:1) (2 ml) was added HOBt (38 mg, 0.28 mmol) and HBTU (96 mg, 0.25 mmol) and the reaction mixture stirred for 15 mins at RT. 1-(Azetidin-3-ylcarbonyl)-4-cyclobutyl-1,4-diazepane (30 mg, 0.13 mmol) in DCM (1 ml) was added and the reaction mixture stirred at RT for 16 hrs. Upon completion, the reaction mixture was evaporated at reduced pressure and purified by silica gel FCC (using DCM/MeOH/NH$_3$; 95:5:0.5 to 90:10:1 as eluent) to give the title compound as colourless oil and as a 1:1 mixture of diastereoisomers by $^1$H NMR spectroscopy (5.2 mg, 11% yield).

LCMS data: Diastereoisomer A—Calculated MH$^+$ (378). Found 43% (MH$^+$) m/z 378, Rt=3.50 min. Method D.

Diastereoisomer B—Calculated MH$^+$ (378). Found 55% (MH$^+$) m/z 378, Rt=3.68 min. Method D.

NMR data: $^1$H NMR (500 MHz, MeOD) δ ppm 4.34-4.49 (2 H, m), 4.11-4.20 (1 H, m), 4.00-4.09 (1 H, m), 3.79 (1 H, m), 3.56-3.68 (2 H, m), 3.40-3.52 (3 H, m), 3.35 (1 H, s), 3.29 (2 H, s), 2.93 (1 H, m), 2.42-2.63 (4 H, m), 2.19-2.39 (1 H, m), 2.03-2.16 (3 H, m), 1.94-2.02 (1 H, m), 1.60-1.93 (8 H, m), 1.41-1.56 (3 H, m), 1.13-1.28 (1 H, m).

The following compounds were prepared as described in Route 9, General Procedure I above.

Example 29

Preparation of 1-cyclobutyl-4-({1-[(4,4-difluorocyclohexyl)carbonyl]azetidin-3-yl}carbonyl)-1,4-diazepane. Potency Range A

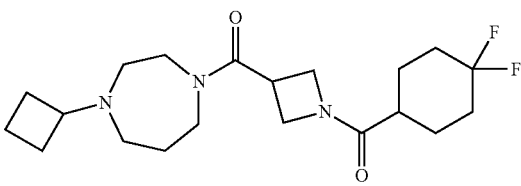 [SMILES: O=C(C1CN(C(=O)C2CCC(F)(F)CC2)C1)N1CCCN(C2CCC2)CC1]

In a similar fashion (Route 9, GP I), 4,4-difluorocyclohexane carboxylic-acid (21 mg, 0.13 mmol) and 1-(azetidin-3-ylcarbonyl)-4-cyclobutyl-1,4-diazepane (30 mg, 0.13 mmol) gave the title compound as colourless oil (5.7 mg, 12% yield).

LCMS data: Calculated MH$^+$ (384). Found 90% (MH$^+$) m/z 384, Rt=3.87 min (Method D).

NMR data: $^1$H NMR (500 MHz, MeOD) δ ppm 4.36-4.49 (2 H, m), 4.13-4.20 (1 H, m), 4.06 (1 H, m), 3.74-3.86 (1 H, m), 3.56-3.72 (2 H, m), 3.37-3.53 (2 H, m), 2.78-3.05 (1 H, m), 2.36-2.64 (5 H, m), 2.03-2.17 (4 H, m), 1.59-1.99 (12 H, m).

Example 30

Preparation of 1-cyclobutyl-4-[(1-{[4-(3,5-dimethyl-1H-pyrazol-1-yl)phenyl]carbonyl}azetidin-3-yl)carbonyl]-1,4-diazepane. Potency Range A

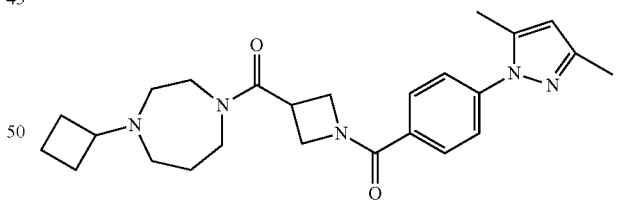

In a similar fashion (Route 9, GP I), 4-(3,5-dimethyl[1H]-pyrazol-1-yl)benzoic acid (27 mg, 0.13 mmol) and 1-(azetidin-3-ylcarbonyl)-4-cyclobutyl-1,4-diazepane (30 mg, 0.13 mmol) gave the title compound as colourless oil (7.1 mg, 13% yield) after purification by preparative HPLC.

LCMS data: Calculated MH$^+$ (436). Found 91% (MH$^+$) m/z 436, Rt=2.65 min (Method C).

NMR data: $^1$H NMR (500 MHz, MeOD) δ ppm 7.82 (2 H, d, J=8.5 Hz), 7.58 (2 H, d, J=8.5 Hz), 6.13 (1 H, s), 4.62 (2 H, d), 4.13-4.50 (3 H, m), 3.90 (1 H, d), 3.66-3.83 (2 H, m), 3.46-3.65 (5 H, m), 2.87-3.16 (2 H, m), 2.35-2.44 (2 H, m), 2.34 (3 H, s), 2.27 (3 H, s), 2.18-2.26 (2 H, m), 2.03-2.18 (1 H, m), 1.74-1.93 (2 H, m).

Example 31

Preparation of 1-cyclobutyl-4-[(1-{[4-(5-methyl-1,3,4-oxadiazol-2-yl)phenyl]carbonyl}azetidin-3-yl)carbonyl]-1,4-diazepane. Potency Range A

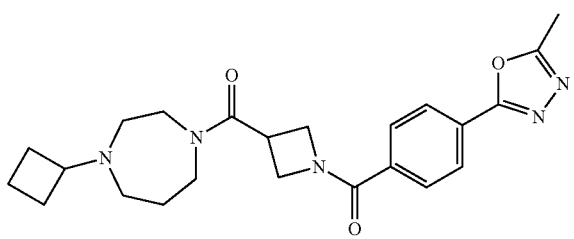 [SMILES: Cc1nnc(-c2ccc(C(=O)N3CC(C(=O)N4CCCN(C5CCC5)CC4)C3)cc2)o1]

In a similar fashion (Route 9, GP I), 4-(5-dimethyl-1,3,4-oxadiazol-2-yl)benzoic acid (26 mg, 0.13 mmol) and 1-(azetidin-3-ylcarbonyl)-4-cyclobutyl-1,4-diazepane (30 mg, 0.13 mmol) gave the title compound (5.6 mg, 10% yield) as colourless oil.

LCMS data: Calculated MH$^+$ (424). Found 98% (MH$^+$) m/z 424, Rt=3.57 min (Method D).

NMR data: $^1$H NMR (500 MHz, MeOD) δ ppm 8.15 (2 H, d, J=8.4 Hz), 7.86 (2 H, d, J=8.4 Hz), 4.52-4.64 (2 H, m), 4.38-4.47 (1 H, m), 4.29-4.37 (1 H, m), 3.86-3.95 (1 H, m), 3.60-3.72 (2 H, m), 3.44-3.54 (2 H, m), 2.95 (1 H, m), 2.66 (3 H, s), 2.54-2.62 (2 H, m), 2.38-2.54 (2 H, m), 2.04-2.19 (2 H, m), 1.81-1.96 (4 H, m), 1.60-1.76 (2 H, m).

Example 32

Preparation of 1-cyclobutyl-4-{[1-(cyclopropylacetyl)azetidin-3-yl]carbonyl}-1,4-diazepane. Potency Range A

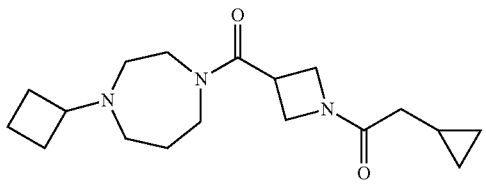 [SMILES: O=C(CC1CC1)N1CC(C(=O)N2CCCN(C3CCC3)CC2)C1]

In a similar fashion (Route 9, GP I), cyclopropyl acetic acid (13 mg, 0.13 mmol) and 1-(azetidin-3-ylcarbonyl)-4-cyclobutyl-1,4-diazepane (30 mg, 0.13 mmol) gave the title compound (5.3 mg, 13% yield) as colourless oil.

LCMS data: Calculated MH$^+$ (320). Found 93% (MH$^+$) m/z 320, Rt=2.07 min (Method D).

NMR data: $^1$H NMR (500 MHz, MeOD) δ ppm 4.32-4.41 (2 H, m), 4.14-4.21 (1 H, m), 4.06-4.12 (1 H, m), 3.74-3.84 (1 H, m), 3.58-3.70 (2 H, m), 3.43-3.52 (2 H, m), 2.93-3.08 (1 H, m), 2.55-2.69 (3 H, m), 2.47-2.55 (1 H, m), 2.10-2.16 (2 H, m), 2.08 (2 H, d, J=7.0 Hz), 1.81-1.98 (4 H, m), 1.62-1.78 (2 H, m), 0.94-1.05 (1 H, m), 0.49-0.57 (2 H, m), 0.18 (2 H, m).

Example 33

Preparation of 1-cyclobutyl-4-{[1-(cyclohexylacetyl)azetidin-3-yl]carbonyl}-1,4-diazepane. Potency Range A

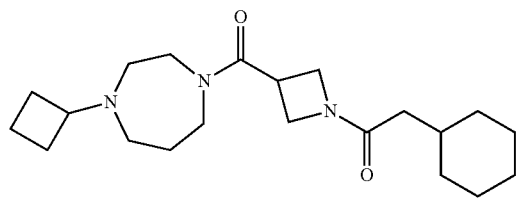 [SMILES: O=C(CC1CCCCC1)N1CC(C(=O)N2CCCN(C3CCC3)CC2)C1]

In a similar fashion (Route 9, GP I), cyclohexylacetic acid (18 mg, 0.13 mmol) and 1-(azetidin-3-ylcarbonyl)-4-cyclobutyl-1,4-diazepane (30 mg, 0.13 mmol) gave the title compound as a colourless oil (11.5 mg, 25% yield) after purification by preparative HPLC.

LCMS data: Calculated MH$^+$ (362). Found 99% (MH$^+$) m/z 362, Rt=2.68 min (Method C).

NMR data: $^1$H NMR (500 MHz, MeOD) δ ppm 4.32-4.47 (2 H, m), 4.14-4.27 (2 H, m), 4.03-4.13 (1 H, m), 3.66-3.86 (3 H, m), 3.41-3.63 (4 H, m), 2.89-3.13 (2 H, m), 2.35 (2 H, m), 2.20-2.30 (3 H, m), 2.06-2.17 (1 H, m), 2.02 (2 H, m), 1.62-1.93 (8 H, m), 1.12-1.37 (3 H, m), 0.91-1.06 (2 H, m).

Example 34

Preparation of 4-(2-{3-[(4-cyclobutyl-1,4-diazepan-1-yl)carbonyl]azetidin-1-yl}-2-oxoethyl)benzonitrile. Potency Range A

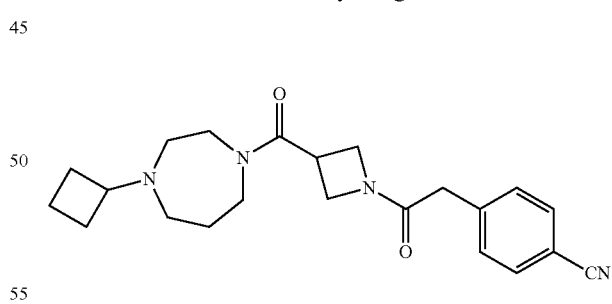

In a similar fashion (Route 9, GP I), 4-cyanophenylacetic acid (20 mg, 0.13 mmol) and 1-(azetidin-3-ylcarbonyl)-4-cyclobutyl-1,4-diazepane (30 mg, 0.13 mmol) gave the title compound as colourless oil (3.9 mg, 8% yield) after purification by preparative HPLC.

LCMS data: Calculated MH$^+$ (381). Found 92% (MH$^+$) m/z 381, Rt=2.36 min (Method C).

NMR data: $^1$H NMR (500 MHz, MeOD) δ ppm 7.69 (2 H, d, J=8.2 Hz), 7.46 (2 H, d, J=8.2 Hz), 4.36-4.57 (2 H, m), 4.16-4.30 (2 H, m), 4.08-4.15 (1 H, m), 3.66-3.88 (3 H, m), 3.62 (2 H, s), 3.46-3.60 (4 H, m), 2.89-3.13 (2 H, m), 2.32-2.42 (2 H, m), 2.18-2.30 (3 H, m), 2.01-2.18 (1 H, m), 1.73-1.93 (2 H, m).

Example 35

Preparation of 1-cyclobutyl-4-[(1-{[4-(1,3-thiazol-2-yl)phenyl]carbonyl}azetidin-3-yl)carbonyl]-1,4-diazepane. Potency Range A

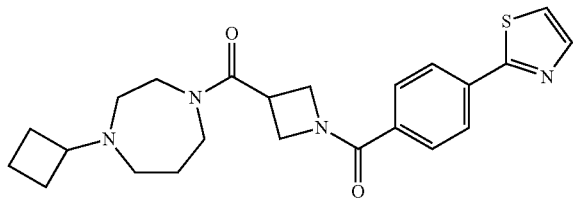 [SMILES: O=C(c1ccc(-c2nccs2)cc1)N1CC(C(=O)N2CCCN(C3CCC3)CC2)C1]

In a similar fashion (Route 9, GP I), 4-(1,3-thiazol-4-yl)benzoic acid (46 mg, 0.22 mmol) and 1-(azetidin-3-ylcarbonyl)-4-cyclobutyl-1,4-diazepane (50 mg, 0.21 mmol) gave the title compound (5 mg, 6% yield) as pale yellow oil after purification by preparative HPLC (Method 2).

LCMS data: Calculated MH$^+$ (425). Found 100% (MH$^+$) m/z 425, Rt=4.08 min (LCMS method D).

$^1$H NMR (500 MHz, MeOD) δ ppm 8.01-8.09 (2 H, m), 7.92 (1 H, d, J=3.2 Hz), 7.77 (2 H, d, J=8.2 Hz), 7.68 (1 H, d, J=3.2 Hz), 4.51-4.62 (2 H, m), 4.26-4.45 (2 H, m), 3.83-3.93 (1 H, m), 3.59-3.71 (2 H, m), 3.42-3.52 (2 H, m), 2.91-3.09 (1 H, m), 2.45-2.69 (4 H, m), 2.01-2.16 (2 H, m), 1.79-1.98 (4 H, m), 1.59-1.77 (2 H, m).

Example 36

Preparation of 1-cyclobutyl-4-[(1-{[4-(2-methyl-1,3-thiazol-4-yl)phenyl]carbonyl}azetidin-3-yl)carbonyl]-1,4-diazepane. Potency Range A

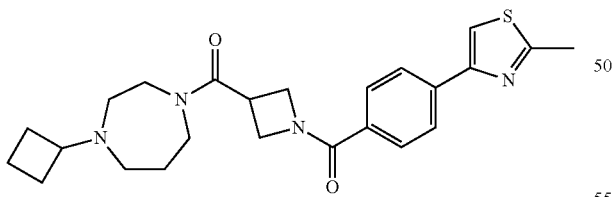

In a similar fashion (Route 9, GP I), 4-(2-methyl-1,3-thiazol-4-yl)benzoic acid (250 mg, 1.15 mmol) and 1-(azetidin-3-ylcarbonyl)-4-cyclobutyl-1,4-diazepane (210 mg, 0.89 mmol) gave the title compound (30 mg, 8% yield) as pale yellow oil after purification by preparative HPLC (Method 2).

LCMS data: Calculated MH$^+$ (439). Found 97% (MH$^+$) m/z 439, Rt=4.24 min (LCMS method D).

$^1$H NMR (500 MHz, MeOD) δ ppm 7.99 (2 H, d, J=8.4 Hz), 7.78 (1 H, s), 7.71 (2 H, d, J=8.4 Hz), 4.52-4.61 (2 H, m), 4.25-4.42 (2 H, m), 3.88 (1 H, m), 3.59-3.76 (2 H, m), 3.43-3.55 (2 H, m), 3.01-3.27 (1 H, m), 2.73-2.83 (5 H, m), 2.55-2.72 (2 H, m), 2.07-2.21 (2 H, m), 1.81-2.06 (4 H, m), 1.60-1.81 (2 H, m).

Example 37

Preparation of 1-cyclobutyl-4-[(1-{[4-(5-methyl-1,2,4-oxadiazol-3-yl)phenyl]carbonyl}azetidin-3-yl)carbonyl]-1,4-diazepane. Potency Range A

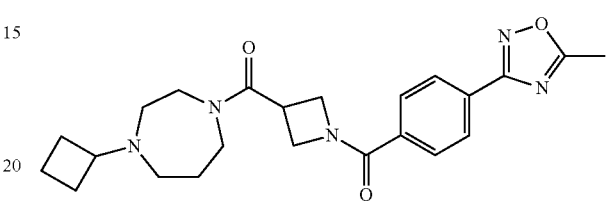

In a similar fashion (Route 9, GP I), 4-(5-methyl-1,2,4-oxadiazol-3-yl)benzoic acid (100 mg, 0.49 mmol) and 1-(azetidin-3-ylcarbonyl)-4-cyclobutyl-1,4-diazepane (140 mg, 0.59 mmol) gave the title compound (3.6 mg, 1.5% yield) as pale yellow oil after purification by preparative HPLC (Method 2).

LCMS data: Calculated MH$^+$ (424). Found 100% (MH$^+$) m/z 424, Rt=2.50 min (LCMS method C).

$^1$H NMR (500 MHz, MeOD) δ ppm 8.14 (2 H, m), 7.80 (2 H, d, J=8.2 Hz), 4.49-4.62 (2 H, m), 4.25-4.44 (2 H, m), 3.78-3.94 (1 H, m), 3.55-3.73 (2 H, m), 3.41-3.54 (2 H, m), 2.90-3.04 (1 H, m), 2.67 (3 H, s), 2.42-2.65 (4 H, m), 2.04-2.14 (2 H, m), 1.77-1.97 (4 H, m), 1.60-1.76 (2 H, m).

Example 38

Preparation of 1-cyclobutyl-4-[(1-{[4-(1-methylethyl)phenyl]carbonyl}azetidin-3-yl)carbonyl]-1,4-diazepane. Potency Range A

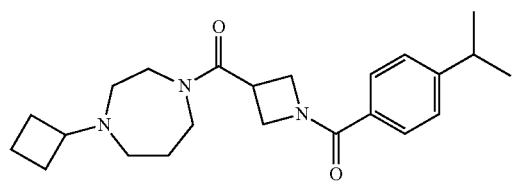 [SMILES: CC(C)c1ccc(C(=O)N2CC(C(=O)N3CCCN(C4CCC4)CC3)C2)cc1]

In a similar fashion (Route 9, GP I), 4-(1-methylethyl)benzoic acid (86 mg, 0.52 mmol) and 1-(azetidin-3-ylcarbonyl)-4-cyclobutyl-1,4-diazepane (125 mg, 0.52 mmol) gave the title compound (24 mg, 12% yield) as pale yellow oil after purification by preparative HPLC (Method 2).

LCMS data: Calculated MH$^+$ (384). Found 98% (MH$^+$) m/z 384, Rt=4.50 min (LCMS method D).

$^1$H NMR (500 MHz, CHLOROFORM-d) δ ppm 7.57 (2 H, d, J=8.2 Hz), 7.26 (2 H, m), 4.63-4.81 (1 H, m), 4.18-4.47 (3 H, m), 3.52-3.81 (3 H, m), 3.29-3.44 (2 H, m), 2.77-2.99 (2 H, m), 2.30-2.63 (4 H, m), 1.97-2.10 (2 H, m), 1.73-1.95 (4 H, m), 1.51-1.73 (2 H, m), 1.25 (6 H, d, J=7.0 Hz).

Example 39

Preparation of 1-cyclobutyl-4-({1-[(4-phenoxyphenyl)carbonyl]azetidin-3-yl}carbonyl)-1,4-diazepane. Potency Range A

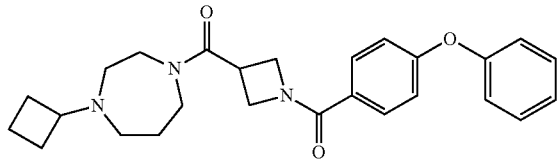 [SMILES: O=C(c1ccc(Oc2ccccc2)cc1)N1CC(C(=O)N2CCCN(C3CCC3)CC2)C1]

In a similar fashion (Route 9, GP I), 4-phenoxybenzoic acid (112 mg, 0.52 mmol) and 1-(azetidin-3-ylcarbonyl)-4-cyclobutyl-1,4-diazepane (125 mg, 0.53 mmol) gave the title compound (34 mg, 15% yield) as pale yellow oil after purification by preparative HPLC (Method 2).

LCMS data: Calculated MH$^+$ (434). Found 100% (MH$^+$) m/z 434, Rt=4.57 min (LCMS method D).

$^1$H NMR (500 MHz, CHLOROFORM-d) δ ppm 7.59-7.68 (2 H, m), 7.34-7.42 (2 H, m), 7.13-7.21 (1 H, m), 7.02-7.08 (2 H, m), 6.95-7.01 (2 H, m), 4.63-4.83 (1 H, m), 4.17-4.50 (3 H, m), 3.53-3.81 (3 H, m), 3.27-3.46 (2 H, m), 2.79-2.99 (1 H, m), 2.29-2.68 (4 H, m), 1.99-2.12 (2 H, m), 1.52-1.99 (6 H, m).

Example 40

Preparation of 1-cyclobutyl-4-[(1-{[4-(1H-pyrazol-1-yl)phenyl]carbonyl}azetidin-3-yl)carbonyl]-1,4-diazepane. Potency Range A

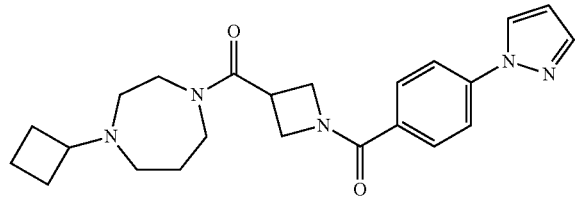 [SMILES: O=C(c1ccc(-n2cccn2)cc1)N1CC(C(=O)N2CCCN(C3CCC3)CC2)C1]

In a similar fashion (Route 9, GP I), 4-(1H-pyrazol-1-yl)benzoic acid (100 mg, 0.52 mmol) and 1-(azetidin-3-ylcarbonyl)-4-cyclobutyl-1,4-diazepane (125 mg, 0.52 mmol) gave the title compound (31 mg, 14% yield) as pale yellow oil after purification by preparative HPLC (Method 2).

LCMS data: Calculated MH$^+$ (408). Found 93% (MH$^+$) m/z 408, Rt=3.84 min (LCMS method D).

$^1$H NMR (500 MHz, CHLOROFORM-d) δ ppm 7.98 (1 H, d, J=2.6 Hz), 7.68-7.82 (5 H, m), 6.49 (1 H, m), 4.75 (1 H, m), 4.21-4.48 (3 H, m), 3.56-3.77 (3 H, m), 3.28-3.44 (2 H, m), 2.85 (1 H, m), 2.31-2.59 (4 H, m), 1.96-2.31 (2 H, m), 1.73-1.96 (4 H, m), 1.52-1.73 (2 H, m).

Example 41

Preparation of 1-cyclobutyl-4-[(1-{[4-(3-methyl-1,2,4-oxadiazol-5-yl)phenyl]carbonyl}azetidin-3-yl)carbonyl]-1,4-diazepane. Potency Range A

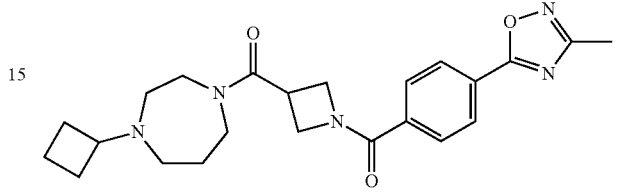

In a similar fashion (Route 9, GP I), 4-(3-methyl-1,2,4-oxadiazol-5-yl)benzoic acid (100 mg, 0.49 mmol) and 1-(azetidin-3-ylcarbonyl)-4-cyclobutyl-1,4-diazepane (119 mg, 0.50 mmol) gave the title compound (8 mg, 4% yield) as pale yellow oil after purification by preparative HPLC (Method 2).

LCMS data: Calculated MH$^+$ (424). Found 92% (MH$^+$) m/z 424, Rt=3.90 min (LCMS method D).

$^1$H NMR (500 MHz, CHLOROFORM-d) δ ppm 8.17 (2 H, d, J=8.5 Hz), 7.80 (2 H, d, J=8.2 Hz), 4.71-4.80 (1 H, m), 4.27-4.48 (3 H, m), 3.58-3.84 (3 H, m), 3.40 (2 H, m), 2.88 (1 H, m), 2.33-2.65 (7 H, m), 2.01-2.11 (2 H, m), 1.87 (2 H, m), 1.55-1.77 (4 H, m).

Example 42

Preparation of 1-cyclobutyl-4-[(1-{[4-(4,4-dimethyl-4,5-dihydro-1,3-oxazol-2-yl)phenyl]carbonyl}azetidin-3-yl)carbonyl]-1,4-diazepane. Potency Range A

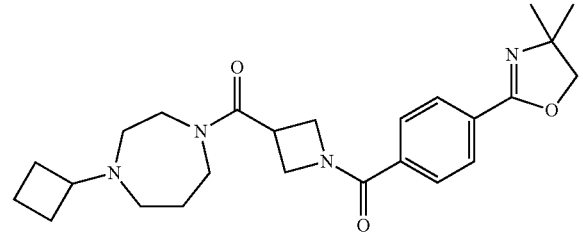 [SMILES: CC1(C)COC(c2ccc(C(=O)N3CC(C(=O)N4CCCN(C5CCC5)CC4)C3)cc2)=N1]

In a similar fashion (Route 9, GP I), 4-(4,4-dimethyl-4,5-dihydro-1,3-oxazol-2-yl)benzoic acid (12 mg, 0.05 mmol) and 1-(azetidin-3-ylcarbonyl)-4-cyclobutyl-1,4-diazepane (20 mg, 0.09 mmol) gave the title compound (3 mg, 13% yield) as pale yellow oil.

LCMS data: Calculated MH$^+$ (439). Found 95% (MH$^+$) m/z 439, Rt=2.36 min (LCMS method C).

$^1$H NMR (500 MHz, MeOD) δ ppm 8.00 (2 H, d, J=8.4 Hz), 7.74 (2 H, d, J=8.2 Hz), 4.53 (2 H, d, J=7.6 Hz), 4.27-4.41 (2 H, m), 4.23 (2 H, s), 3.84-3.92 (1 H, m), 3.60-3.66 (2 H, m), 3.44-3.48 (2 H, m), 2.88-2.97 (1 H, m), 2.52-2.59 (2 H, m), 2.43-2.49 (2 H, m), 2.04-2.11 (2 H, m), 1.82-1.90 (4 H, m), 1.62-1.73 (2 H, m), 1.39 (6 H, s).

Example 43

Preparation of 1-cyclobutyl-4-({1-[(6-methylpyridin-3-yl)acetyl]azetidin-3-yl}carbonyl)-1,4-diazepane. Potency Range A

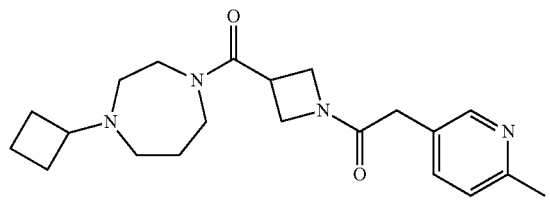 [SMILES: Cc1ccc(CC(=O)N2CC(C(=O)N3CCCN(C4CCC4)CC3)C2)cn1]

In a similar fashion (Route 9, GP I), 1-(azetidin-3-ylcarbonyl)-4-cyclobutyl-1,4-diazepane (137 mg, 0.57 mmol) and (6-methylpyridin-3-yl)acetic acid (73 mg, 0.48 mmol) gave the title compound (16 mg, 9%) as colourless oil after purification by preparative HPLC (Method 2). LCMS data: Calculated MH$^+$ (371). Found 100% (MH$^+$) m/z 371, Rt=3.41 min (Method D).

NMR data: $^1$H NMR (500 MHz, MeOD) δ ppm 8.31 (1 H, d, J=1.7 Hz), 7.65 (1 H, dd, J=8.0, 2.1 Hz), 7.27 (1 H, d, J=8.1 Hz), 4.39-4.51 (2 H, m), 4.15-4.23 (1 H, m), 4.05-4.15 (1 H, m), 3.75-3.88 (1 H, m), 3.56-3.69 (2 H, m), 3.53 (2 H, s), 3.41-3.50 (2 H, m), 2.88-3.01 (1 H, m), 2.39-2.61 (7 H, m), 2.04-2.13 (2 H, m), 1.77-1.96 (4 H, m), 1.59-1.76 (2 H, m).

Example 44

Preparation of 1-cyclobutyl-4-({1-[(4-pyridin-3-ylphenyl)carbonyl]azetidin-3-yl}carbonyl)-1,4-diazepane. Potency Range A

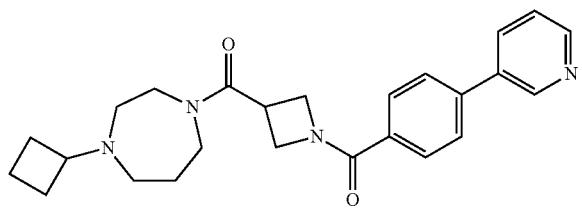 [SMILES: O=C(c1ccc(-c2cccnc2)cc1)N1CC(C(=O)N2CCCN(C3CCC3)CC2)C1]

In a similar fashion (Route 9, GP I), 1-(azetidin-3-ylcarbonyl)-4-cyclobutyl-1,4-diazepane (118 mg, 0.50 mmol) and 4-pyrid-3-ylbenzoic acid (100 mg, 0.50 mmol) gave the title compound (39 mg, 19%) after purification by preparative HPLC (Method 2).

LCMS data: Calculated MH$^+$ (419). Found 100% (MH$^+$) m/z 419, Rt=3.82 min (Method C).

NMR data: $^1$H NMR (500 MHz, CHLOROFORM-d) δ ppm 8.86 (1 H, d, J=2.0 Hz), 8.63 (1 H, dd, J=4.8, 1.4 Hz), 7.90 (1 H, dt, J=7.9, 2.0 Hz), 7.77 (2 H, d, J=8.4 Hz), 7.63 (2 H, d, J=8.2 Hz), 7.40 (1 H, dd, J=7.9, 4.8 Hz), 4.71-4.84 (1 H, m), 4.35-4.49 (2 H, m), 4.26-4.35 (1 H, m), 3.57-3.80 (3 H, m), 3.31-3.45 (2 H, m), 2.81-2.95 (1 H, m), 2.34-2.63 (4 H, m), 1.99-2.11 (2 H, m), 1.75-1.99 (4 H, m), 1.55-1.75 (2 H, m).

Example 45

Preparation of 1-cyclobutyl-4-({1-[(4-pyridin-4-ylphenyl)carbonyl]azetidin-3-yl}carbonyl)-1,4-diazepane. Potency Range A

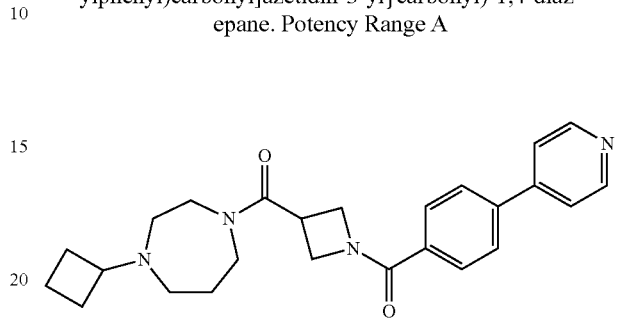

In a similar fashion (Route 9, GP I), 1-(azetidin-3-ylcarbonyl)-4-cyclobutyl-1,4-diazepane (118 mg, 0.50 mmol) and 4-pyrid-4-ylbenzoic acid (100 mg, 0.50 mmol) gave the title compound (25 mg, 12%).

LCMS data: Calculated MH$^+$ (419). Found 100% (MH$^+$) m/z 419, Rt=3.82 min (Method C). NMR data: $^1$H NMR (500 MHz, CHLOROFORM-d) δ ppm 8.68 (2 H, d, J=5.0 Hz), 7.75 (2H, d, J=8.1 Hz), 7.68 (2 H, d, J=8.1 Hz), 7.51 (2 H, d, J=5.3 Hz), 4.75 (1 H, m), 4.34-4.50 (2 H, m), 4.24-4.33 (1 H, m), 3.57-3.96 (3 H, m), 3.34-3.52 (2 H, m), 3.04-3.13 (1 H, m), 2.69 (4 H, m), 2.04-2.26 (5 H, m), 1.91-2.01 (1 H, m), 1.59-1.77 (2 H, m).

Example 46

Preparation of 1-cyclobutyl-4-[(1-{[3-(2-methyl-1,3-thiazol-4-yl)phenyl]carbonyl}azetidin-3-yl)carbonyl]-1,4-diazepane. Potency Range A

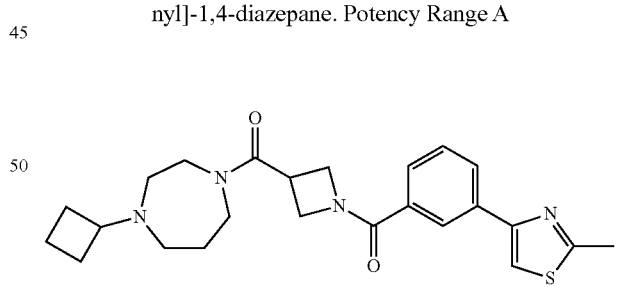

In a similar fashion (Route 9, GP I), 1-(azetidin-3-ylcarbonyl)-4-cyclobutyl-1,4-diazepane (100 mg, 0.42 mmol) and 3-(2-methyl-1,3-thiazol-4-yl)benzoic acid (92 mg, 0.42 mmol) gave the title compound (55 mg, 34%).

LCMS data: Calculated MH$^+$ (439). Found 99% (MH$^+$) m/z 439, Rt=2.58 min (Method C).

NMR data: $^1$H NMR (500 MHz, CHLOROFORM-d) δ ppm 8.10 (1 H, s), 7.97 (1 H, d, J=7.9 Hz), 7.54 (1 H, d, J=7.8 Hz), 7.40-7.46 (1 H, m), 7.36 (1 H, s), 4.69 (1 H, d, J=8.1 Hz), 4.25-4.43 (3 H, m), 3.56-3.74 (3 H, m), 3.31-3.38 (2 H, m), 2.87 (1 H, s), 2.74 (3 H, s), 2.33-2.61 (4 H, m), 1.97-2.06 (2 H, m), 1.74-1.94 (4 H, m), 1.59 (2 H, s).

Example 47

Preparation of 2-({3-[(4-cyclobutyl-1,4-diazepan-1-yl)carbonyl]azetidin-1-yl}carbonyl)-1H-benzimidazole

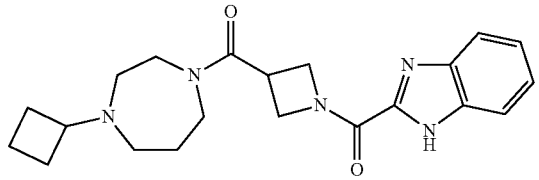 [SMILES: O=C(c1nc2ccccc2[nH]1)N1CC(C(=O)N2CCCN(C3CCC3)CC2)C1]

In a similar fashion (Route 9, GP I), 1-(azetidin-3-ylcarbonyl)-4-cyclobutyl-1,4-diazepane (100 mg, 0.42 mmol) and 1H-1,3-benzimidazole-2-carboxylic acid (69 mg, 0.42 mmol) gave the title compound (26 mg, 10%) after purification by preparative HPLC (Method 1) as the TFA salt.

LCMS data: Calculated MH$^+$ (382). Found 100% (MH$^+$) m/z 382, Rt=2.42 min (Method C).

NMR data: $^1$H NMR (500 MHz, MeOD) δ ppm 7.63-7.72 (2 H, m), 7.29-7.43 (2 H, m), 4.86-5.08 (2 H, m), 4.33-4.53 (2 H, m), 4.13-4.30 (1 H, m), 3.42-4.01 (8 H, m), 2.86-3.15 (2 H, m), 2.07-2.43 (6 H, m), 1.72-1.93 (2 H, m).

Example 48

Preparation of 5-({3-[(4-cyclobutyl-1,4-diazepan-1-yl)carbonyl]azetidin-1-yl}carbonyl)-1-methyl-1H-benzimidazole

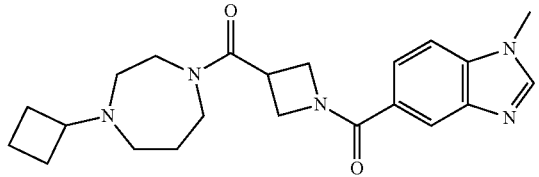 [SMILES: Cn1cnc2cc(C(=O)N3CC(C(=O)N4CCCN(C5CCC5)CC4)C3)ccc21]

In a similar fashion (Route 9, GP I), 1-(azetidin-3-ylcarbonyl)-4-cyclobutyl-1,4-diazepane (100 mg, 0.42 mmol) and 1-methyl-benzimidazole-5-carboxylic acid (76 mg, 0.42 mmol) gave the title compound (35 mg, 21%) after purification by preparative HPLC (Method 2).

LCMS data: Calculated MH$^1$ (396). Found (MH$^1$) m/z 396, Rt=3.51 min (Method D).

NMR data: Purity by NMR >95%. $^1$H NMR (500 MHz, MeOD) δ ppm 8.21 (1 H, s), 7.95 (1 H, s), 7.55-7.69 (2 H, m), 4.54 (2 H, m), 4.36 (1 H, m), 4.24-4.32 (1 H, m), 3.89 (3 H, s), 3.80-3.88 (1 H, m), 3.54-3.66 (2 H, m), 3.39-3.47 (2 H, m), 2.88 (1 H, m), 2.47-2.56 (2 H, m), 2.36-2.46 (2 H, m), 2.01-2.08 (2 H, m), 1.75-1.89 (4 H, m), 1.57-1.70 (2 H, m).

Example 49

Preparation of 5-({3-[(4-cyclobutyl-1,4-diazepan-1-yl)carbonyl]azetidin-1-yl}carbonyl)-1-methyl-1H-benzotriazole

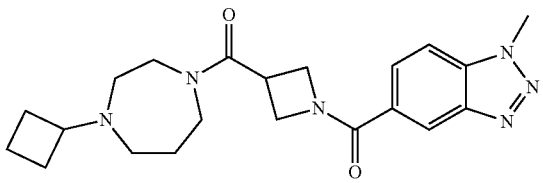 [SMILES: Cn1nnc2cc(C(=O)N3CC(C(=O)N4CCCN(C5CCC5)CC4)C3)ccc21]

In a similar fashion (Route 9, GP I), 1-(azetidin-3-ylcarbonyl)-4-cyclobutyl-1,4-diazepane (100 mg, 0.42 mmol) and 1-methyl-1,2,3-benzotriazole-5-carboxylic acid (75 mg, 0.42 mmol) gave the title compound (40 mg, 24%) after purification by preparative HPLC (Method 2).

LCMS data: Calculated MH$^1$ (397). Found 98% (MH$^1$) m/z 397, Rt=3.49 min (Method D).

NMR data: $^1$H NMR (500 MHz, MeOD) δ ppm 8.27 (1 H, s), 7.84 (2 H, s), 4.53-4.64 (2 H, m), 4.28-4.47 (5 H, m), 3.82-3.96 (1 H, m), 3.55-3.73 (2 H, m), 3.39-3.53 (2 H, m), 2.82-2.97 (1 H, m), 2.50-2.61 (2 H, m), 2.39-2.50 (2 H, m), 2.00-2.12 (2 H, m), 1.76-1.93 (4 H, m), 1.57-1.75 (2 H, m).

Example 50

Preparation of 7-({3-[(4-cyclobutyl-1,4-diazepan-1-yl)carbonyl]azetidin-1-yl}carbonyl)imidazo[1,2-α]pyridine

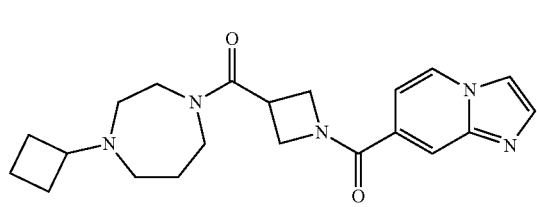 [SMILES: O=C(c1ccn2ccnc2c1)N1CC(C(=O)N2CCCN(C3CCC3)CC2)C1]

In a similar fashion (Route 9, GP I), 1-(azetidin-3-ylcarbonyl)-4-cyclobutyl-1,4-diazepane (175 mg, 0.74 mmol) and imidazo[1,2-a]pyridine-7-carboxylic acid (120 mg, 0.74 mmol) gave the title compound (34 mg, 9%) after purification by preparative HPLC (Method 2).

LCMS data: Calculated MH$^+$ (382). Found 100% (MH$^+$) m/z 382, Rt=3.37 min (Method D).

NMR data: $^1$H NMR (500 MHz, MeOD) δ ppm 8.53 (1 H, d, J=7.0 Hz), 7.97 (1 H, s), 7.85 (1 H, s), 7.72 (1 H, s), 7.18 (1 H, d, J=7.0 Hz), 4.55-4.70 (2 H, m), 4.24-4.46 (2 H, m), 3.83-3.97 (1 H, m), 3.58-3.68 (2 H, m), 3.41-3.53 (2 H, m), 2.86-2.99 (1 H, m), 2.42-2.63 (4 H, m), 2.01-2.13 (2 H, m), 1.77-1.98 (4 H, m), 1.56-1.76 (2 H, m)

Example 51

Preparation of 1-cyclobutyl-4-{[1-(1H-1,2,4-triazol-3-ylcarbonyl)azetidin-3-yl]carbonyl}-1,4-diazepane

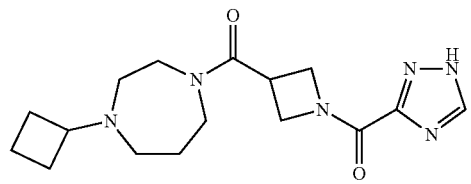 [SMILES: O=C(c1nc[nH]n1)N1CC(C(=O)N2CCCN(C3CCC3)CC2)C1]

In a similar fashion (Route 9, GP I), 1-(azetidin-3-ylcarbonyl)-4-cyclobutyl-1,4-diazepane (100 mg, 0.42 mmol) and 1,2,4-triazole-3-carboxylic acid (47 mg, 0.42 mmol) gave the title compound (45 mg, 32%) after purification by preparative HPLC (Method 2).

LCMS data: Calculated MH$^+$ (333). Found 100% (MH$^+$) m/z 333, Rt=2.24 min (Method D).

NMR data: $^1$H NMR (500 MHz, MeOD) δ ppm 8.44 (1 H, s), 4.74-4.87 (2 H, m), 4.26-4.42 (2 H, m), 3.84-3.97 (1 H, m), 3.56-3.73 (2 H, m), 3.46-3.53 (2 H, m), 2.88-3.04 (1 H, m), 2.56-2.66 (2 H, m), 2.43-2.56 (2 H, m), 2.02-2.16 (2 H, m), 1.80-1.99 (4 H, m), 1.59-1.79 (2 H, m)

Example 52

Preparation of 1-cyclobutyl-4-({1-[(1-methyl-1H-pyrazol-4-yl)carbonyl]azetidin-3-yl}carbonyl)-1,4-diazepane

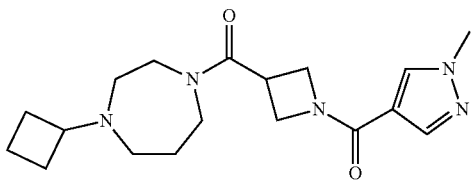 [SMILES: Cn1cc(C(=O)N2CC(C(=O)N3CCCN(C4CCC4)CC3)C2)cn1]

In a similar fashion (Route 9, GP I), 1-(azetidin-3-ylcarbonyl)-4-cyclobutyl-1,4-diazepane (25 mg, 0.11 mmol) and 1-methyl-pyrazole-4-carboxylic acid (13 mg, 0.11 mmol) gave the title compound (10 mg, 26%) after purification by preparative HPLC (Method 2).

LCMS data: Calculated MH$^+$ (346). Found 100% (MH$^+$) m/z 346, Rt=1.83 min (Method C).

NMR data: $^1$H NMR (500 MHz, MeOD) δ ppm 8.03 (1 H, s), 7.78 (1 H, s), 4.52-4.63 (2 H, m), 4.24-4.33 (1 H, m), 4.14-4.23 (1 H, m), 3.90 (3 H, s), 3.82-3.89 (1 H, m), 3.56-3.67 (2 H, m), 3.42-3.51 (2 H, m), 2.84-2.96 (1 H, m), 2.49-2.59 (2 H, m), 2.39-2.49 (2 H, m), 2.02-2.12 (2 H, m), 1.77-1.93 (4 H, m), 1.58-1.72 (2 H, m).

Route 10

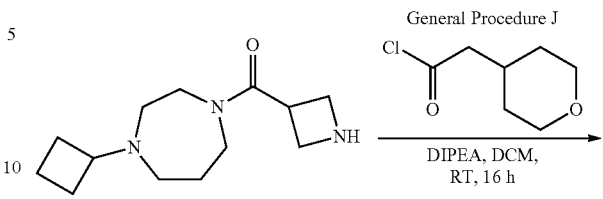

General Procedure J:

Example 53

Preparation of 1-cyclobutyl-4-{[1-(tetrahydro-2H-pyran-4-ylacetyl)azetidin-3-yl]carbonyl}-1,4-diazepane. Potency Range C

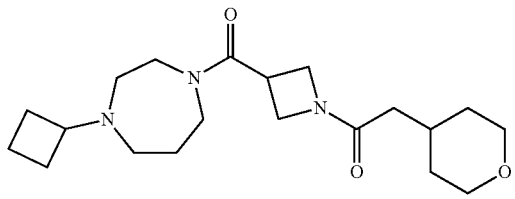 [SMILES: O=C(CC1CCOCC1)N1CC(C(=O)N2CCCN(C3CCC3)CC2)C1]

To a stirred solution of 1-(azetidin-3-ylcarbonyl)-4-cyclobutyl-1,4-diazepane (30 mg, 0.13 mmol) and DIPEA (42 µl, 0.25 mmol) in DCM (1 ml) was added tetrahydropyran-4-yl acetyl chloride (21 mg, 0.13 mmol) in DCM (1 ml). The reaction mixture stirred at RT for 16 hrs. Upon completion, water and 1M HCl were added and the reaction mixture was washed with DCM (3×5 ml). The combined organic phases were dried (MgSO$_4$), filtered and concentrated at reduced pressure. The residue was purified by preparative HPLC to afford the title compound as colourless oil (1.2 mg, 3% yield).

LCMS data: Calculated MH$^+$ (364). Found 95% (MH$^+$) m/z 364, Rt=3.33 min (Method D).

NMR data: $^1$H NMR (500 MHz, MeOD) δ ppm 4.31-4.49 (2 H, m), 4.14-4.29 (2 H, m), 4.10 (1 H, m), 3.92 (3 H, m), 3.67-3.86 (2 H, m), 3.56 (1 H, m), 3.46-3.53 (1 H, m), 3.39-3.46 (3 H, m), 3.23 (1 H, m), 3.01-3.15 (1 H, m), 2.88-3.01 (1 H, m), 2.32-2.45 (1 H, m), 2.17-2.32 (2 H, m), 2.14 (1 H, m), 2.08-2.11 (1 H, m), 1.94-2.06 (2 H, m), 1.74-1.92 (1 H, m), 1.65 (2 H, m), 1.25-1.46 (5 H, m).

The following compound was prepared as described in Route 10, General Procedure J above.

Example 54

Preparation of 1-({1-[(4-chlorophenyl)acetyl]azetidin-3-yl}carbonyl)-4-cyclobutyl-1,4-diazepane. Potency Range A

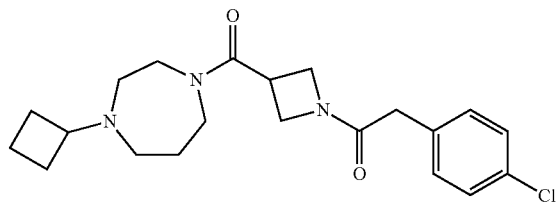 [SMILES: O=C(Cc1ccc(Cl)cc1)N1CC(C(=O)N2CCCN(C3CCC3)CC2)C1]

In a similar fashion (Route 10, GP J), 1-(azetidin-3-ylcarbonyl)-4-cyclobutyl-1,4-diazepane (100 mg, 0.42 mmol) and 4-chlorobenzeneacetyl chloride (88 mg, 0.46 mmol) gave the title compound (55 mg, 34%).

LCMS data: Calculated MH$^+$ (390). Found 100% (MH$^+$) m/z 390, Rt=2.54 min (Method C).

NMR data: $^1$H NMR (500 MHz, CHLOROFORM-d) δ ppm 7.26-7.34 (2 H, m), 7.22 (2 H, d, J=8.2 Hz), 4.52-4.60 (1 H, m), 4.15-4.24 (2 H, m), 4.04-4.14 (1 H, m), 3.75-3.82 (1 H, m), 3.65-3.74 (1 H, m), 3.51-3.62 (1 H, m), 3.29-3.47 (4 H, m), 2.87-3.01 (1 H, m), 2.41-2.77 (4 H, m), 1.96-2.13 (4 H, m), 1.84-1.91 (2 H, m), 1.59-1.77 (2 H, m).

Example 55

1-cyclobutyl-4-[(1-{[4-(methylsulfonyl)phenyl]carbonyl}azetidin-3-yl)carbonyl]-1,4-diazepane. Potency Range A

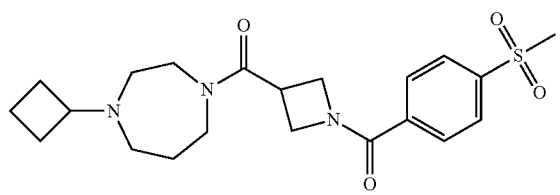 [SMILES: CS(=O)(=O)c1ccc(C(=O)N2CC(C(=O)N3CCCN(C4CCC4)CC3)C2)cc1]

In a similar fashion (Route 10, GP J), 1-(azetidin-3-ylcarbonyl)-4-cyclobutyl-1,4-diazepane (50 mg, 0.21 mmol) and 4-(methylsulfonyl)benzoyl chloride (51 mg, 0.23 mmol) gave the title compound as the TFA salt (22.7 mg, 20%) after purification by silica FCC (eluting with 96:3.6:0.4 of DCM/MeOH/NH$_3$) followed by preparative HPLC (Method 1).

LCMS data: Calculated MH$^+$ (420). Found 100% (MH$^+$) m/z 420, Rt=2.11 min (Method C).

NMR data: $^1$H NMR (500 MHz, CHLOROFORM-d) δ ppm 8.04 (2 H, d, J=8.2 Hz), 7.84 (2 H, d, J=7.6 Hz), 4.61-4.80 (1 H, m), 4.23-4.55 (4 H, m), 3.51-3.77 (5 H, m), 3.27-3.48 (2 H, m), 3.11 (3 H, s), 2.14-2.90 (8 H, m), 1.88-2.00 (1 H, m), 1.68-1.84 (1 H, m).

Route 11

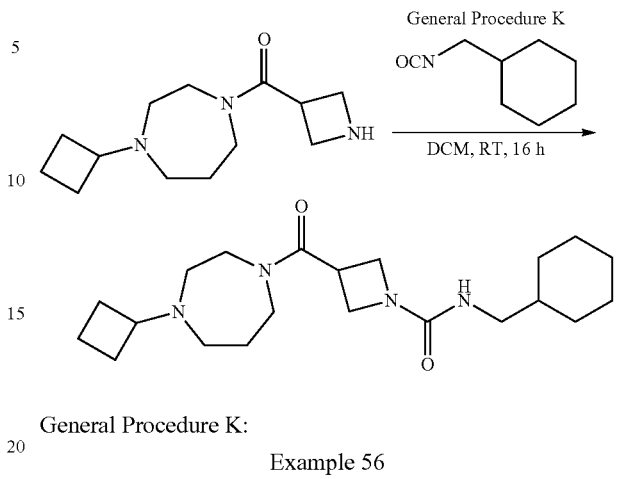

General Procedure K:

Example 56

Preparation of 3-[(4-cyclobutyl-1,4-diazepan-1-yl)carbonyl]-N-(cyclohexylmethyl)azetidine-1-carboxamide. Potency Range A

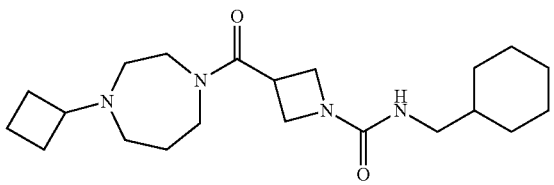 [SMILES: O=C(NCC1CCCCC1)N1CC(C(=O)N2CCCN(C3CCC3)CC2)C1]

To a stirred solution of 1-(azetidin-3-ylcarbonyl)-4-cyclobutyl-1,4-diazepane (30 mg, 0.13 mmol) in DCM (1 ml) was added cyclohexanemethyl isocyanate (18 µl, 0.13 mmol) in DCM (1 ml). The reaction mixture was stirred at RT for 16 hrs then evaporated at reduced pressure and the resulting crude material purified by silica FCC (using a gradient of eluents; 99:1:1 to 90:10:1 DCM:MeOH:7M NH$_3$ in MeOH) to provide the title compound as colourless oil (39 mg, 82% yield).

LCMS data: Calculated MH$^+$ (377). Found 96% (MH$^+$) m/z 377, Rt=4.18 min (Method D).

NMR data: $^1$H NMR (250 MHz, CHLOROFORM-d) δ ppm 4.12-4.25 (3 H, m), 3.98-4.11 (2 H, m), 3.58-3.72 (2 H, m), 3.44-3.58 (2 H, m), 3.26-3.43 (2 H, m), 3.03 (2 H, t, J=6.4 Hz), 2.75-2.94 (1 H, m), 2.29-2.62 (4 H, m), 1.97-2.17 (2 H, m), 1.78-1.96 (3 H, m), 1.53-1.78 (6 H, m), 1.43 (1 H, m), 1.03-1.34 (4 H, m), 0.71-1.02 (2 H, m).

The following compounds were prepared as described in Route 11, General Procedure K above.

Example 57

Preparation of 3-[(4-cyclobutyl-1,4-diazepan-1-yl)carbonyl]-N-(tetrahydro-2H-pyran-4-ylmethyl)azetidine-1-carboxamide. Potency Range A

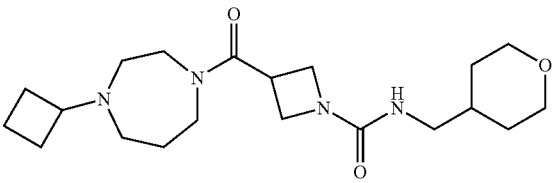 [SMILES: O=C(NCC1CCOCC1)N1CC(C(=O)N2CCCN(C3CCC3)CC2)C1]

In a similar fashion (Route 11, GP K), 4-(isocyanatomethyl)tetrahydropyran (18 mg, 0.13 mmol) and 1-(azetidin-3-ylcarbonyl)-4-cyclobutyl-1,4-diazepane (30 mg, 0.13 mmol) gave the title compound (36 mg, 74% yield) as colourless oil.

LCMS data: Calculated MH+ (379). Found 90% (MH+) m/z 379, Rt=1.91 min (Method C).

NMR data: ¹H NMR (500 MHz, CHLOROFORM-d) δ ppm 4.14-4.27 (3 H, m), 4.02-4.13 (2 H, m), 3.97 (2 H, m), 3.60-3.71 (2 H, m), 3.54 (1 H, m), 3.29-3.43 (4 H, m), 3.10 (2 H, m), 2.79-2.94 (1 H, m), 2.46-2.55 (2 H, m), 2.36-2.46 (2 H, m), 2.04 (2 H, m), 1.77-1.95 (4 H, m), 1.50-1.77 (5 H, m), 1.22-1.38 (2 H, m).

Example 58

Preparation of 3-[(4-cyclobutyl-1,4-diazepan-1-yl)carbonyl]-N-(4-fluorobenzyl)azetidine-1-carboxamide. Potency Range A

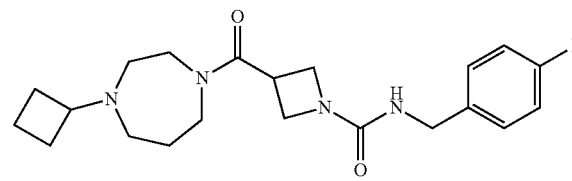

In a similar fashion (Route 11, GP K), 4-fluorobenzylisocyanate (16.1 μl, 0.13 mmol) and 1-(azetidin-3-ylcarbonyl)-4-cyclobutyl-1,4-diazepane (30 mg, 0.13 mmol) gave the title compound (25.5 mg, 52% yield) as colourless oil.

LCMS data: Calculated MH+ (389). Found 92% (MH+) m/z 389, Rt=2.48 min (Method C).

NMR data: ¹H NMR (500 MHz, CHLOROFORM-d) δ ppm 7.23-7.30 (2 H, m), 6.98-7.05 (2 H, m), 4.40-4.46 (1 H, m), 4.34-4.38 (2 H, m), 4.19-4.28 (2 H, m), 4.04-4.11 (2 H, m), 3.61-3.68 (2 H, m), 3.50-3.59 (1 H, m), 3.31-3.38 (2 H, m), 2.80-2.91 (1 H, m), 2.46-2.52 (2 H, m), 2.37-2.45 (2 H, m), 1.99-2.09 (2 H, m), 1.75-1.92 (4 H, m), 1.56-1.74 (2 H, m).

Example 59

Preparation of N-(4-cyanophenyl)-3-[(4-cyclobutyl-1,4-diazepan-1-yl)carbonyl]azetidine-1-carboxamide. Potency Range A

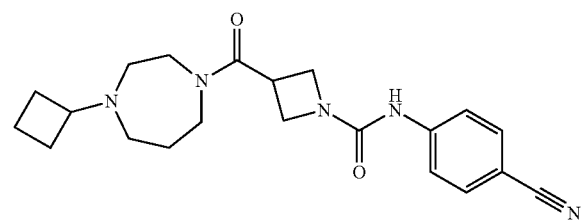

In a similar fashion (Route 11, GP K), 1-(azetidin-3-ylcarbonyl)-4-cyclobutyl-1,4-diazepane (150 mg, 0.63 mmol) and 4-cyanophenyl isocyanate (136 mg, 0.95 mmol) gave the title compound (20 mg, 8%) as colourless oil after purification by preparative HPLC (Method 2).

LCMS data: Calculated MH+ (382). Found 99% (MH+) m/z 382, Rt=3.84 min (Method D).

NMR data: ¹H NMR (500 MHz, CHLOROFORM-d) δ ppm 7.48-7.62 (4 H, m), 6.36 (1 H, s), 4.30-4.42 (2 H, m), 4.15-4.28 (2 H, m), 3.54-3.73 (3 H, m), 3.32-3.43 (2 H, m), 2.88 (1 H, m), 2.37-2.60 (4 H, m), 2.01-2.10 (2 H, m), 1.75-1.99 (4 H, m), 1.51-1.76 (2 H, m).

Route 12

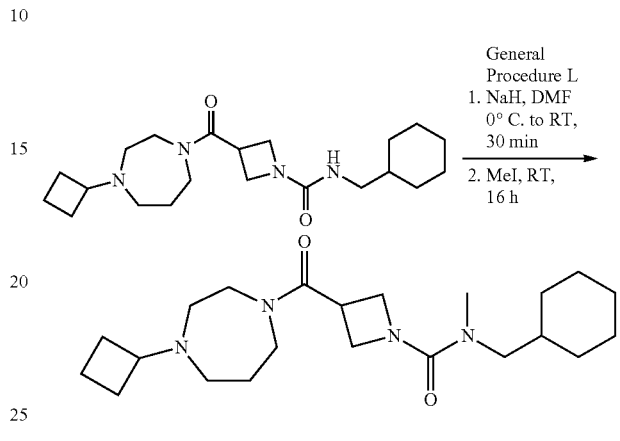

General Procedure L:

Example 60

Preparation of 3-[(4-cyclobutyl-1,4-diazepan-1-yl)carbonyl]-N-(cyclohexylmethyl)-N-methylazetidine-1-carboxamide. Potency Range A

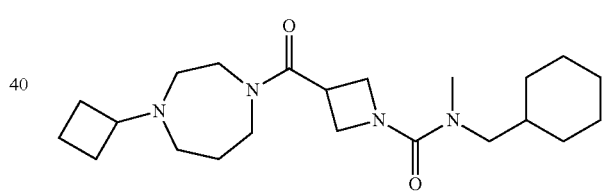

To a stirred solution of 3-[(4-cyclobutyl-1,4-diazepan-1-yl)carbonyl]-N-(cyclohexylmethyl)azetidine-1-carboxamide (26 mg, 0.069 mmol) in dry DMF (1 ml) at 0° C. under a nitrogen atmosphere was added sodium hydride (4.1 mg of a 60% dispersion in mineral oil, 0.103 mmol). The resulting suspension was stirred at 0° C. for 30 min. Methyl iodide (4.3 μl, 0.069 mmol) was added and the reaction mixture allowed to warm to RT and was stirred for 16 hrs. The reaction mixture was poured onto ice-water, extracted with EtOAc (3×5 ml), the combined organics washed with brine (5 ml), dried (MgSO₄), filtered and concentrated at reduced pressure. Purification by preparative HPLC provided the title compound (5.6 mg, 21% yield) as colourless oil.

LCMS data: Calculated MH+ (391). Found 94% (MH+) m/z 391, Rt=2.97 min (Method C).

NMR data: ¹H NMR (500 MHz, MeOD) δ ppm 4.16 (4 H, m), 3.93-4.11 (1 H, m), 3.64-3.86 (3 H, m), 3.41-3.63 (4 H, m), 3.10 (2 H, m), 3.00-3.08 (1 H, m), 2.90-3.00 (1 H, m), 2.87 (3 H, s), 2.31-2.43 (2 H, m), 2.17-2.30 (3 H, m), 1.98-2.17 (1 H, m), 1.79-1.93 (2 H, m), 1.58-1.78 (6 H, m), 1.12-1.35 (3 H, m), 0.84-1.04 (2 H, m).

The following compounds were prepared as described in Route 12, General Procedure L above.

Example 61

Preparation of 3-[(4-cyclobutyl-1,4-diazepan-1-yl)carbonyl]-N-methyl-N-(tetrahydro-2H-pyran-4-ylmethyl)azetidine-1-carboxamide. Potency Range A

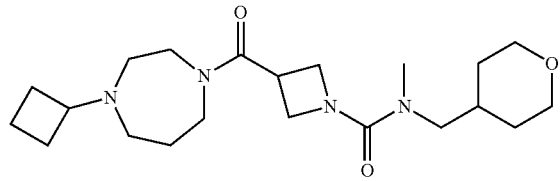

In a similar fashion (Route 12, GP L), 3-[(4-cyclobutyl-1,4-diazepan-1-yl)carbonyl]-N-(tetrahydro-2H-pyran-4-ylmethyl)azetidine-1-carboxamide (24.9 mg, 0.066 mmol), sodium hydride (3.9 mg of a 60% dispersion in mineral oil, 0.099 mmol) and methyl iodide (4.1 μl, 0.066 mmol) gave the title compound (4.2 mg, 16% yield) as colourless oil.

LCMS data: Calculated MH$^+$ (393). Found 94% (MH$^+$) m/z 393, Rt=2.20 min (Method C).

NMR data: $^1$H NMR (500 MHz, MeOD) δ ppm 4.12-4.29 (4 H, m), 3.97-4.12 (1 H, m), 3.94 (2 H, m), 3.66-3.87 (3 H, m), 3.46-3.63 (4 H, m), 3.36-3.43 (2 H, m), 3.14-3.22 (2 H, m), 2.93-3.12 (2 H, m), 2.91 (3 H, s), 2.32-2.46 (2 H, m), 2.17-2.31 (3 H, m), 2.00-2.16 (1 H, m), 1.75-1.99 (3 H, m), 1.50-1.68 (2 H, m), 1.19-1.35 (2 H, m).

Example 62

Preparation of 3-[(4-cyclobutyl-1,4-diazepan-1-yl)carbonyl]-N-(4-fluorobenzyl)-N-methylazetidine-1-carboxamide. Potency Range A

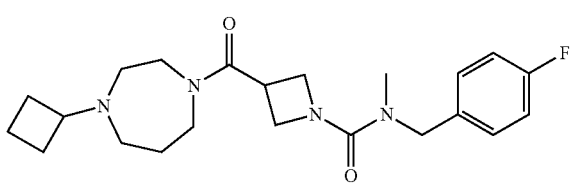 [SMILES: CN(Cc1ccc(F)cc1)C(=O)N1CC(C(=O)N2CCCN(C3CCC3)CC2)C1]

In a similar fashion (Route 12, GP L), 3-[(4-cyclobutyl-1,4-diazepan-1-yl)carbonyl]-N-(4-fluorobenzyl)azetidine-1-carboxamide (18 mg, 0.046 mmol), sodium hydride (2.8 mg of a 60% dispersion in mineral oil, 0.070 mmol) and methyl iodide (2.9 μl, 0.046 mmol) gave the title compound (4.3 mg, 23% yield) as colourless oil.

LCMS data: Calculated MH$^+$ (403). Found 90% (MH$^+$) m/z 403, Rt=2.72 min (Method C).

NMR data: $^1$H NMR (500 MHz, MeOD) δ ppm 7.19-7.41 (2 H, m), 6.93-7.16 (2 H, m), 4.44 (2 H, s), 4.14-4.25 (4 H, m), 3.64-3.95 (3 H, m), 3.40-3.62 (5 H, m), 3.05 (1 H, m), 2.90-3.01 (1 H, m), 2.83 (3 H, s), 2.31-2.54 (2 H, m), 2.18-2.31 (3 H, m), 1.98-2.17 (1 H, m), 1.68-1.93 (2 H, m).

Example 63

Preparation of 3-[(4-cyclobutyl-1,4-diazepan-1-yl)carbonyl]-N-(4-fluorobenzyl)-N-methylazetidine-1-carboxamide. Potency Range A

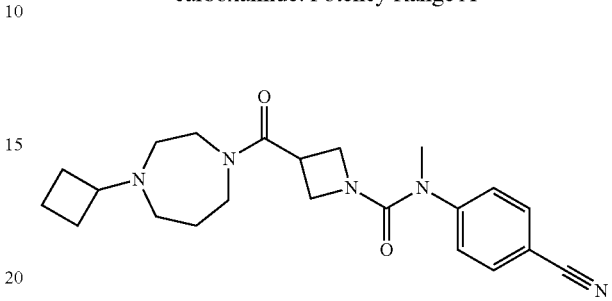

In a similar fashion (Route 12, GP L), N-(4-cyanophenyl)-3-[(4-cyclobutyl-1,4-diazepan-1-yl)carbonyl]azetidine-1-carboxamide (80 mg, 0.21 mmol) and methyl iodide (16 μl, 0.25 mmol) gave the title compound (2.7 mg, 3%) as colourless oil after purification by preparative HPLC (Method 2).

LCMS data: Calculated MH$^+$ (396). Found 100% (MH$^+$) m/z 396, Rt=3.77 min (Method D).

NMR data: $^1$H NMR (500 MHz, CHLOROFORM-d) δ ppm 7.65 (2 H, d, J=8.4 Hz), 7.33 (2 H, d, J=8.5 Hz), 3.90-4.02 (2 H, m), 3.51-3.83 (4 H, m), 3.20-3.45 (6 H, m), 2.79-2.99 (1 H, m), 2.26-2.66 (4 H, m), 2.02 (2 H, m), 1.45-1.97 (6 H, m).

Example 64

Preparation of N-(4-cyanobenzyl)-3-[(4-cyclobutyl-1,4-diazepan-1-yl)carbonyl]-N-methylazetidine-1-carboxamide. Potency Range A

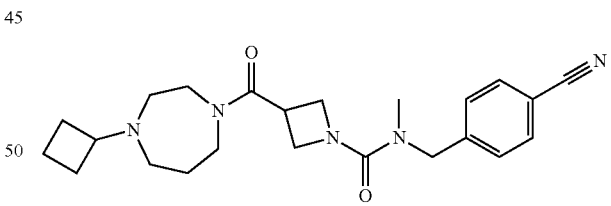

In a similar fashion (Route 12, GP L), N-(4-cyanobenzyl)-3-[(4-cyclobutyl-1,4-diazepan-1-yl)carbonyl]azetidine-1-carboxamide (35 mg, 88 μmol) and methyl iodide (68 μl, 105 μmol) gave the title compound (1.1 mg, 0.3%) as colourless oil after purification by preparative HPLC (Method 2).

LCMS data: Calculated MH$^+$ (410). Found 100% (MH$^+$) m/z 410, Rt=2.53 min (Method D).

NMR data: $^1$H NMR (500 MHz, MeOD) δ ppm 7.72 (2 H, d, J=8.1 Hz), 7.45 (2 H, d, J=8.1 Hz), 4.50-4.62 (2 H, m), 4.14-4.26 (4 H, m), 3.71-3.80 (1 H, m), 3.59-3.71 (2 H, m), 3.42-3.52 (2 H, m), 3.31-3.39 (2 H, m), 2.86 (3 H, s), 2.48-2.75 (3 H, m), 2.05-2.19 (2 H, m), 1.81-2.00 (4 H, m), 1.62-1.79 (2 H, m).

Route 13

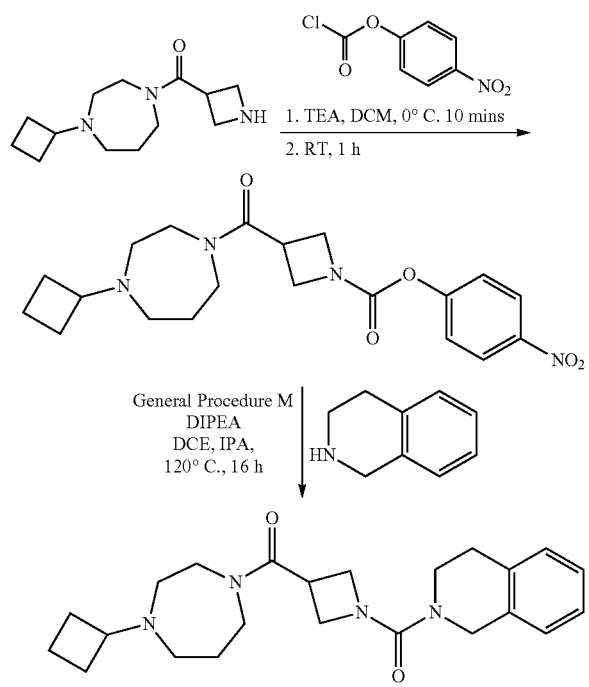

Preparation of 4-nitrophenyl 3-[(4-cyclobutyl-1,4-diazepan-1-yl)carbonyl]azetidine-1-carboxylate

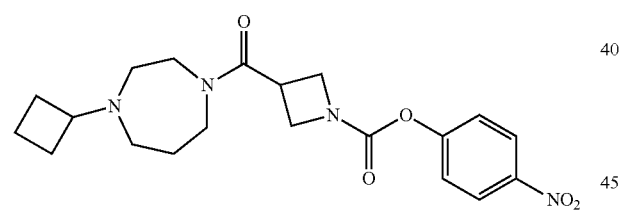

To a solution of 1-(azetidin-3-ylcarbonyl)-4-cyclobutyl-1,4-diazepane (208 mg, 0.88 mmol) and TEA (146 μl, 1.05 mmol) in dichloromethane (5 ml) at 0° C. was added 4-nitrophenylchloroformate (176 mg, 0.88 mmol). After 10 minutes the reaction temperature was raised to RT and after a further hour the mixture was diluted with dichloromethane (30 ml), washed with 1M aq. K$_2$CO$_3$ (2×15 ml), dried (MgSO$_4$), filtered and concentrated at reduced pressure. The residue was purified by silica FCC (using a gradient of eluents 99:1:1 to 92:8:1 DCM/MeOH/2M NH$_3$ in MeOH) to give the title compound (206 mg, 58% yield) as yellow oil.

LCMS data: Calculated MH$^+$ (403). Found 99% (MH$^+$) m/z 403, Rt=4.36 min.

NMR data: $^1$H NMR (500 MHz, CDCl$_3$) δ ppm 8.20-8.31 (2 H, m), 7.29-7.37 (2 H, m), 4.51-4.65 (1 H, m), 4.19-4.42 (3 H, m), 3.56-3.77 (3 H, m), 3.29-3.43 (2 H, m), 2.80-2.94 (1 H, m), 2.35-2.62 (4 H, m), 1.99-2.09 (2 H, m), 1.75-1.95 (4 H, m), 1.52-1.75 (2 H, m).

General Procedure M:

Example 65

Preparation of 2-({3-[(4-cyclobutyl-1,4-diazepan-1-yl)carbonyl]azetidin-1-yl}carbonyl)-1,2,3,4-tetrahydroisoquinoline. Potency Range A

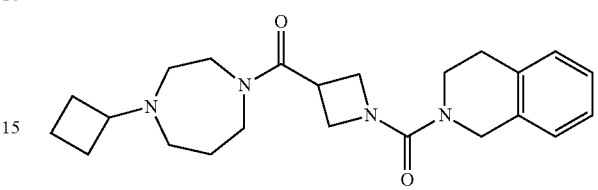

4-Nitrophenyl 3-[(4-cyclobutyl-1,4-diazepan-1-yl)carbonyl]azetidine-1-carboxylate (50 mg, 0.12 mmol), 1,2,3,4-tetrahydroisoquinoline (25 μl, 0.19 mmol) and DIPEA (42 μl, 0.24 mmol) were stirred in 1,2-dichloroethane (2 ml) and isopropanol (1 ml) at 120° C. in a sealed tube for 16 hrs. The mixture was then cooled to RT, diluted with dichloromethane (30 ml) and washed with 1M aq. K$_2$CO$_3$ (2×15 ml), dried (MgSO$_4$), filtered and concentrated at reduced pressure. The residue was purified by silica FCC (eluting with 99:1:1 to 92:8:1 gradient of DCM/MeOH/2M NH$_3$ in MeOH) to give the title compound (9 mg, 19% yield) as colourless oil.

LCMS data: Calculated MH$^+$ (397). Found 88% (MH$^+$) m/z 397, Rt=4.26 min (Method D).

NMR data: $^1$H NMR (500 MHz, CDCl$_3$) δ ppm 7.05-7.23 (4 H, m), 4.50 (2 H, s), 4.23-4.35 (2 H, m), 4.11-4.23 (2 H, m), 3.61-3.72 (2 H, m), 3.46-3.61 (3 H, m), 3.31-3.39 (2 H, m), 2.80-2.92 (3 H, m), 2.34-2.57 (4 H, m), 1.98-2.10 (2 H, m), 1.53-1.96 (6 H, m).

The following compound was prepared as described in Route 13, General Procedure M above.

Example 66

Preparation of N-(4-cyanobenzyl)-3-[(4-cyclobutyl-1,4-diazepan-1-yl)carbonyl]azetidine-1-carboxamide. Potency Range A

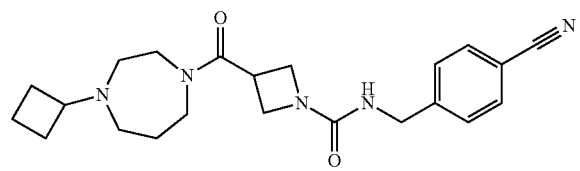 [SMILES: N#Cc1ccc(CNC(=O)N2CC(C(=O)N3CCCN(C4CCC4)CC3)C2)cc1]

In a similar fashion (Route 13, GP M), 4-nitrophenyl 3-[(4-cyclobutyl-1,4-diazepan-1-yl)carbonyl]azetidine-1-carboxylate (100 mg, 0.25 mmol) and 4-cyanobenzylamine hydrochloride (46 mg, 0.27 mmol) gave the title compound (7 mg, 7% yield) as colourless oil after purification by preparative HPLC (Method 2).

LCMS data: Calculated MH$^+$ (396). Found 96% (MH$^+$) m/z 396, Rt=3.75 min (Method D).

NMR data: $^1$H NMR (500 MHz, MeOD) δ ppm 7.64-7.71 (2 H, m), 7.47 (2 H, d, J=8.4 Hz), 4.38 (2 H, s), 4.08-4.20 (4 H, m), 3.74-3.84 (1 H, m), 3.57-3.70 (2 H, m), 3.40-3.52 (2 H, m), 2.87-3.00 (1 H, m), 2.52-2.62 (2 H, m), 2.42-2.52 (2 H, m), 2.02-2.14 (2 H, m), 1.79-1.94 (4 H, m), 1.58-1.78 (2 H, m).

Route 14

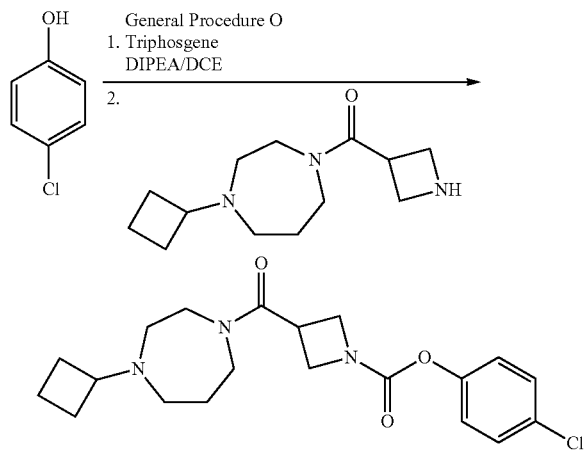

General Procedure O:

Example 67

Preparation of 4-chlorophenyl 3-[(4-cyclobutyl-1,4-diazepan-1-yl)carbonyl]azetidine-1-carboxylate. Potency Range A

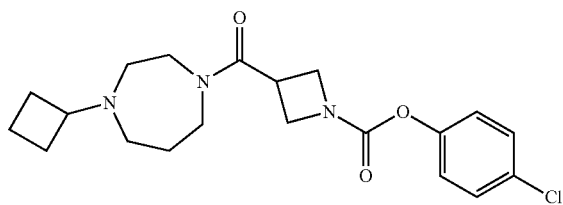 [SMILES: O=C(Oc1ccc(Cl)cc1)N1CC(C(=O)N2CCCN(C3CCC3)CC2)C1]

A stirred solution of 4-chlorophenol (200 mg, 1.56 mmol) and triphosgene (460 mg, 1.56 mmol) in DCE (5 ml) was cooled to 0° C. and DIPEA (2.16 ml, 12.4 mmol) added. The resulting solution was stirred at 0° C. for 90 minutes then 1-(azetidin-3-ylcarbonyl)-4-cyclobutyl-1,4-diazepane (367 mg, 1.56 mmol) in DCE (2 ml) was added. The resulting mixture was heated at 100° C. for 12 hours then cooled to room temperature and diluted with DCM (25 ml) and water (30 ml). The organic phase was separated and the aqueous phase extracted with DCM (3×25 ml). The organics were combined, dried (MgSO$_4$), filtered and concentrated at reduced pressure. The residue was purified by FCC (98:2:1 DCM:MeOH:NH$_3$) followed by preparative HPLC (Method 2) to yield the title compound (1.4 mg, 0.2% yield).

LCMS data: Calculated MH$^+$ (392). Found 100% (MH$^+$) m/z 392, Rt=2.86 min (Method C).

NMR data: $^1$H NMR (500 MHz, MeOD) δ ppm 7.30-7.40 (2 H, m), 6.99-7.19 (2 H, m), 4.35 (2 H, m), 4.19 (2 H, m), 3.80-3.88 (1 H, m), 3.59-3.67 (2 H, m), 3.43-3.48 (2 H, m), 2.94 (1 H, m), 2.56 (2 H, m), 2.45-2.50 (2 H, m), 2.04-2.10 (2 H, m), 1.81-1.92 (4 H, m), 1.62-1.72 (2 H, m).

The following compound was prepared as described in Route 14, General Procedure O above.

Example 68

Preparation of 6-methylpyridin-3-yl 3-[(4-cyclobutyl-1,4-diazepan-1-yl)carbonyl]azetidine-1-carboxylate. Potency Range A

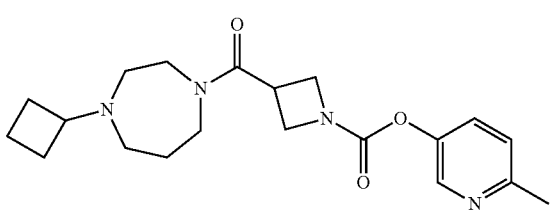 [SMILES: Cc1ccc(OC(=O)N2CC(C(=O)N3CCCN(C4CCC4)CC3)C2)cn1]

In a similar fashion (Route 14, GP O), 1-(azetidin-3-ylcarbonyl)-4-cyclobutyl-1,4-diazepane (430 mg, 1.83 mmol) and 3-hydroxy-6-methylpyridine (200 mg, 1.83 mmol) gave the title compound (0.6 mg, 0.1%) as colourless oil after purification by preparative HPLC (Method 2).

LCMS data: Calculated MH$^+$ (373). Found (MH$^+$) m/z 373. The product eluted in the solvent front. (Method C).

NMR data: $^1$H NMR (500 MHz, MeOD) δ ppm 8.22 (1 H, d, J=2.6 Hz), 7.51 (1 H, dd, J=8.5, 2.7 Hz), 7.30 (1 H, d, J=8.4 Hz), 4.31-4.48 (2 H, m), 4.21 (2 H, m), 3.86 (1 H, m), 3.57-3.71 (2 H, m), 3.43-3.49 (2 H, m), 2.94 (1 H, m), 2.54-2.65 (2 H, m), 2.50 (3 H, s), 2.43-2.48 (2 H, m), 2.03-2.12 (2 H, m), 1.77-1.95 (4 H, m), 1.56-1.73 (2 H, m).

Example 69

Preparation of 4-cyanophenyl 3-[(4-cyclobutyl-1,4-diazepan-1-yl)carbonyl]azetidine-1-carboxylate. Potency Range A

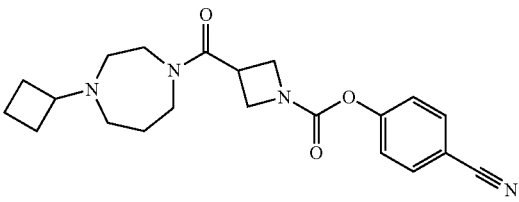 [SMILES: N#Cc1ccc(OC(=O)N2CC(C(=O)N3CCCN(C4CCC4)CC3)C2)cc1]

In a similar fashion (Route 14, GP O), 1-(azetidin-3-ylcarbonyl)-4-cyclobutyl-1,4-diazepane (200 mg, 1.26 mmol) and 4-cyanophenol (150 mg, 1.26 mmol) gave the title compound (6 mg, 1%) after purification by preparative HPLC (Method 2).

LCMS data: Calculated MH$^+$ (383). Found (MH$^+$) m/z 383. The product was not stable to the LCMS conditions giving several UV peaks (Method C).

NMR data: $^1$H NMR (500 MHz, CHLOROFORM-d) δ ppm 7.64-7.69 (2 H, m), 7.24-7.29 (2 H, m), 4.56 (1 H, m), 4.20-4.39 (3 H, m), 3.60-3.81 (3 H, m), 3.39 (3 H, m), 2.81-2.96 (1 H, m), 2.34-2.66 (4 H, m), 2.01-2.13 (2 H, m), 1.76 2.01 (3 H, m), 1.53-1.76 (3 H, m).

Route 15

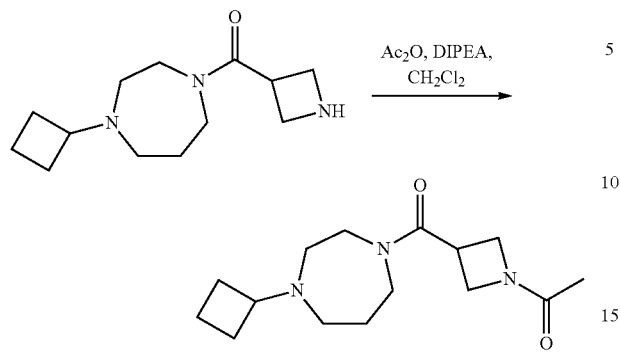

Example 70

Preparation of 1-[(1-acetylazetidin-3-yl)carbonyl]-4-cyclobutyl-1,4-diazepane. Potency Range A

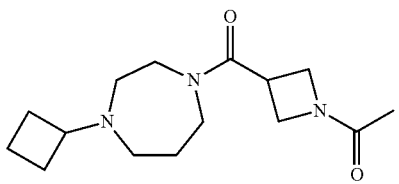 [SMILES: CC(=O)N1CC(C(=O)N2CCCN(C3CCC3)CC2)C1]

To a stirred solution of 1-(azetidin-3-ylcarbonyl)-4-cyclobutyl-1,4-diazepane (100 mg, 0.42 mmol) in dichloromethane (10 mL) cooled to 0° C. was added diisopropylethylamine (160 mg, 1.26 mmol) and acetic anhydride (45 mg, 0.51 mmol). The resulting mixture was stirred at RT for 3 h before it was quenched by addition of water (10 ml). The aqueous layer was extracted with dichloromethane (3×10 ml) and the combined organic layers were washed with saturated aqueous NaHCO$_3$ (10 ml), dried (Na$_2$SO$_4$), filtered and concentrated. Purification by silica FCC (using a gradient of eluents; 100:0 to 99:1 DCM:2M NH$_3$ in MeOH) followed by purification by preparative HPLC (Method 2) gave the title compound (35 mg, 30% yield) as colourless oil.

LCMS data: Calculated MH$^1$ (280). Found 99% (MH$^1$) m/z 280, Rt=3.10 min (Method D).

$^1$H NMR (500 MHz, CHLOROFORM-d) δ ppm 4.55 (1 H, m), 4.14-4.24 (2 H, m), 4.02-4.13 (1 H, m), 3.47-3.81 (3 H, m), 3.29-3.45 (2 H, m), 2.83-2.96 (1 H, m), 2.34-2.68 (4 H, m), 1.91-2.12 (4 H, m), 1.78-1.91 (5 H, m), 1.55-1.77 (2 H, m).

Route 16

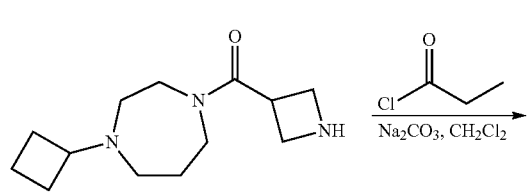

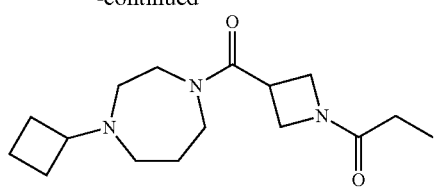

Example 71

Preparation of 1-cyclobutyl-4-[(1-propanoylazetidin-3-yl)carbonyl]-1,4-diazepane. Potency Range A

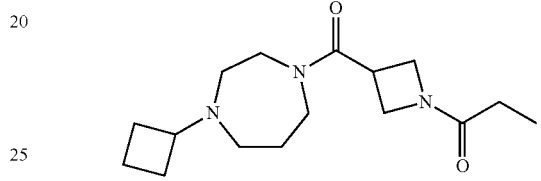

To a stirred solution of 1-(azetidin-3-ylcarbonyl)-4-cyclobutyl-1,4-diazepane (125 mg, 0.53 mmol) in dichloromethane (5 ml) at 0° C. was added sodium carbonate (167 mg, 1.58 mmol) and propionyl chloride (58 mg, 0.63 mmol). The resulting mixture was stirred at RT for 13 h before volatiles were removed under reduced pressure. Purification by silica FCC (using a gradient of eluents; 100:0 to 98:2 DCM:2M NH$_3$ in MeOH) followed by purification by preparative HPLC (Method 2) gave the title compound (18 mg, 12% yield) as pale yellow oil. LCMS data: Calculated MH$^1$ (294). Found 86% (MH$^1$) m/z 294, Rt=3.18 min (Method D).

$^1$H NMR (500 MHz, CHLOROFORM-d) δ ppm 4.47-4.57 (1 H, m), 4.12-4.23 (2 H, m), 4.00-4.12 (1 H, m), 3.46-3.74 (3 H, m), 3.27-3.42 (2 H, m), 2.79-2.91 (1 H, m), 2.30-2.57 (4 H, m), 1.95-2.19 (4 H, m), 1.72-1.93 (4 H, m), 1.52-1.72 (2 H, m), 1.10 (3 H, t, J=7.6 Hz).

Route 17

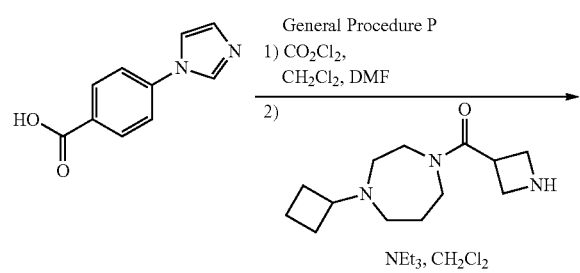

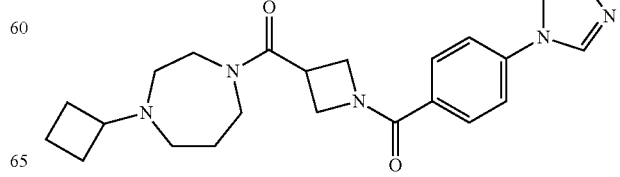

Example 72

Preparation of 1-cyclobutyl-4-[(1-{[4-(1H-imidazol-1-yl)phenyl]carbonyl}azetidin-3-yl)carbonyl]-1,4-diazepane. Potency Range A

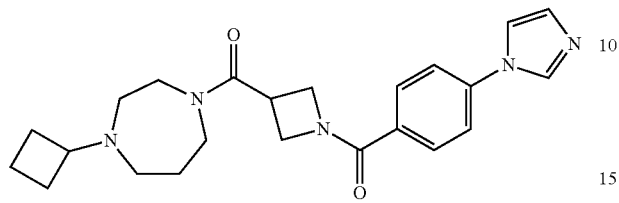

To a solution of 4-(1H-imidazol-1-yl)benzoic acid (150 mg, 0.80 mmol) in dichloromethane (10 mL) cooled to 0° C. was added oxalyl chloride (1 mL). DMF (2 drops) was added and the mixture was stirred for 45 min at 0° C. and volatiles were then removed at reduced pressure. The residue was diluted with dichloromethane (20 mL), cooled to 0° C. and triethylamine (201 mg, 2.0 mmol) was added followed by 1-(azetidin-3-ylcarbonyl)-4-cyclobutyl-1,4-diazepane (187 mg, 0.79 mmol). The resulting mixture was stirred at RT for 16 h before being diluted with more dichloromethane (50 mL) and quenched by addition of water (50 mL). The organic layer was then washed with saturated aqueous NaHCO$_3$ (50 mL), dried (Na$_2$SO$_4$), filtered and concentrated at reduced pressure. Purification by silica FCC (using a gradient of eluents; 97:3 to 95:5 DCM/2M NH$_3$ in MeOH) followed by purification by preparative HPLC (Method 2) gave the title compound (14 mg, 4% yield) as pale yellow oil.

LCMS data: Calculated MH$^+$ (408). Found 100% (MH$^+$) m/z 408, Rt=3.38 min (Method D).

$^1$H NMR (500 MHz, MeOD) δ ppm 8.26 (1 H, s), 7.84 (2 H, d, J=8.5 Hz), 7.72 (2 H, d, J=8.7 Hz), 7.68 (1 H, s), 7.19 (1 H, s), 4.50-4.64 (2 H, m), 4.35-4.45 (1 H, m), 4.24-4.35 (1 H, m), 3.84-3.94 (1 H, m), 3.57-3.70 (2 H, m), 3.42-3.53 (2 H, m), 2.86-2.99 (1 H, m), 2.42-2.63 (4 H, m), 2.01-2.13 (2 H, m), 1.78-1.95 (4 H, m), 1.59-1.75 (2 H, m).

The following compound was prepared as described in Route 17, General Procedure P above.

Example 73

Preparation of 1-cyclobutyl-4-[(1-{[4-(1H-1,2,4-triazol-1-yl)phenyl]carbonyl}azetidin-3-yl)carbonyl]-1,4-diazepane. Potency Range A

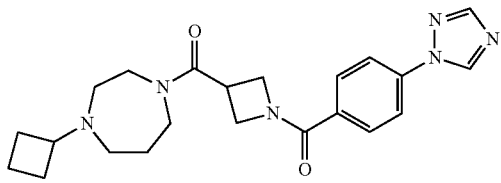 [SMILES: O=C(c1ccc(-n2cncn2)cc1)N1CC(C(=O)N2CCCN(C3CCC3)CC2)C1]

In a similar fashion (Route 17, GP P), 4-(1H-1,2,4-triazol-1-yl)benzoic acid (100 mg, 0.53 mmol) and 1-(azetidin-3-ylcarbonyl)-4-cyclobutyl-1,4-diazepane (125 mg, 0.53 mmol) gave the TFA salt of the title compound (32 mg, 12% yield) as yellow oil after purification by preparative HPLC (Method 1).

LCMS data: Calculated MH$^+$ (409). Found 100% (MH$^+$) m/z 409, Rt=2.14 min (Method C).

$^1$H NMR (500 MHz, MeOD) δ ppm 9.22 (1 H, s), 8.22 (1 H, s), 7.97 (2 H, d, J=8.5 Hz), 7.85 (2 H, d, J=8.5 Hz), 4.51-4.68 (2 H, m), 4.27-4.50 (2 H, m), 4.13-4.27 (1 H, m), 3.84-3.95 (1 H, m), 3.66-3.84 (2 H, m), 3.40-3.66 (4 H, m), 2.87-3.15 (2 H, m), 2.05-2.41 (6 H, m), 1.72-1.92 (2 H, m).

Example 74

Preparation of 1-cyclobutyl-4-[(1-{[4-(1H-1,2,4-triazol-1-ylmethyl)phenyl]carbonyl}azetidin-3-yl)carbonyl]-1,4-diazepane. Potency Range A

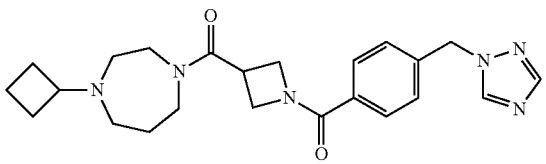 [SMILES: O=C(c1ccc(Cn2cncn2)cc1)N1CC(C(=O)N2CCCN(C3CCC3)CC2)C1]

In a similar fashion (Route 17 GP P), 4-(1H-1,2,4-triazol-1-ylmethyl)benzoic acid (60 mg, 0.29 mmol) and 1-(azetidin-3-ylcarbonyl)-4-cyclobutyl-1,4-diazepane (62 mg, 0.261 mmol) gave the title compound (1.2 mg, 1%) as an oil after purification by preparative HPLC (Method 2).

LCMS data: Calculated MH$^+$ (423). Found 95% (MH$^+$) m/z 423, Rt=3.52 min (Method D).

NMR data: $^1$H NMR (500 MHz, MeOD) δ ppm 8.61 (1 H, s), 8.02 (1 H, s), 7.66 (2 H, d, J=8.2 Hz), 7.41 (2 H, d, J=8.1 Hz), 5.51 (2 H, s), 4.46-4.60 (2 H, m), 4.31-4.43 (1 H, m), 4.23-4.31 (1 H, m), 3.81-3.94 (1 H, m), 3.56-3.70 (2 H, m), 3.41-3.52 (2 H, m), 2.83-3.01 (1 H, m), 2.52-2.60 (2 H, m), 2.41-2.53 (2 H, m), 2.05-2.12 (2 H, m), 1.78-1.94 (4 H, m), 1.59-1.77 (2 H, m).

Example 75

Preparation of 1-cyclobutyl-4-({1-[(2-methylpyridin-4-yl)carbonyl]azetidin-3-yl}carbonyl)-1,4-diazepane. Potency Range A

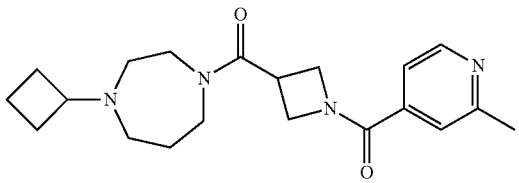 [SMILES: Cc1cc(C(=O)N2CC(C(=O)N3CCCN(C4CCC4)CC3)C2)ccn1]

In a similar fashion (Route 17 GP P), 2-methylpyridine-4-carboxylic acid (100 mg, 0.73 mmol) and 1-(azetidin-3-ylcarbonyl)-4-cyclobutyl-1,4-diazepane (50 mg, 0.21 mmol) gave the title compound after purification by silica FCC (90:9:1 Et$_2$O/MeOH/NH$_3$).

NMR data: (96% purity by $^1$H NMR). $^1$H NMR (500 MHz, MeOD) δ ppm 8.54 (1 H, d, J=5.2 Hz), 7.50 (1 H, s), 7.42 (1 H, d, J=5.2 Hz), 4.46-4.56 (2 H, m), 4.34-4.42 (1 H, m), 4.34-4.42 (1 H, m), 4.25-4.34 (1 H, m), 3.84-3.94 (1 H, m), 3.59-3.71 (2 H, m), 3.43-3.50 (2 H, m), 2.95 (1 H, m), 2.54-2.63 (5 H, m), 2.45-2.53 (2 H, m), 2.08 (2 H, q, J=8.0 Hz), 1.80-1.97 (4 H, m), 1.61-1.76 (2 H, m).

Route 18

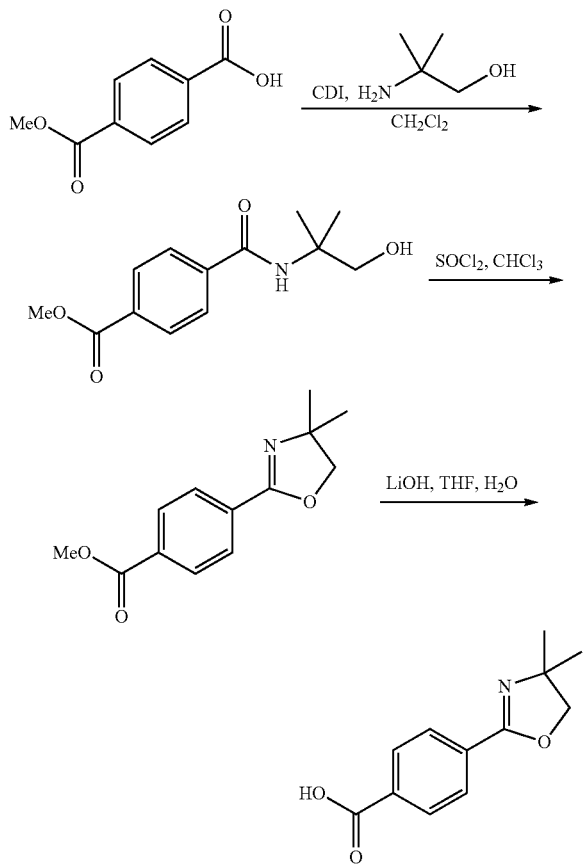

Preparation of methyl 4-[(2-hydroxy-1,1-dimethylethyl)carbamoyl]benzoate

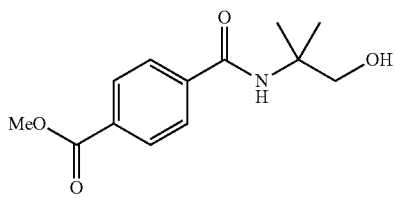 [SMILES: COC(=O)c1ccc(C(=O)NC(C)(C)CO)cc1]

To a suspension of mono-methylterephtalate (360 mg, 2.0 mmol) in dichloromethane (10 mL) under $N_2$ was added 1,1'-carbonyldiimidazole (422 mg, 2.6 mmol) in one portion. The mixture was stirred at RT for 18 h. 2-Amino-2-methyl-1-propanol (232 mg, 2.6 mmol) was added as a solution in dichloromethane (1 mL) and stirring was continued for another 3 h. The reaction was quenched by pouring onto saturated aqueous $NaHCO_3$ (50 mL). After extraction with dichloromethane (3×50 mL), the combined organic extracts were washed with brine (50 mL), dried ($MgSO_4$), filtered and concentrated at reduced pressure. Purification by silica FCC (using a gradient of eluents; 7:3 to 1:1 heptane:EtOAc) gave the title compound (100 mg, 20% yield) as white solid.

LCMS data: Calculated $MH^+$ (252); Found 100% ($MH^+$) m/z 252, Rt=1.08 min (Method A).

$^1$H NMR (500 MHz, CHLOROFORM-d) δ ppm 8.10 (2 H, d, J=8.4 Hz), 7.80 (2 H, d, J=8.4 Hz), 6.23 (1 H, br. s.), 3.95 (3 H, s), 3.72 (2 H, s), 1.44 (6 H, s).

Preparation of methyl 4-(4,4-dimethyl-4,5-dihydro-1,3-oxazol-2-yl)benzoate

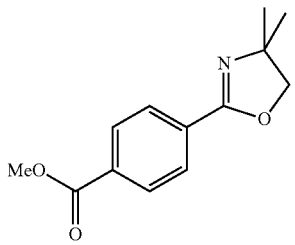 [SMILES: COC(=O)c1ccc(C2=NC(C)(C)CO2)cc1]

To a solution of methyl 4-[(2-hydroxy-1,1-dimethylethyl)carbamoyl]benzoate (100 mg, 0.40 mmol) in $CDCl_3$ (2 mL) was added thionyl chloride (57 mg, 0.48 mmol). The mixture was heated to 60° C. in a sealed tube for 4 h. After cooling, the reaction was quenched by pouring onto saturated aqueous $NaHCO_3$ (20 mL). After extraction with dichloromethane (3×20 mL), the combined organic extracts were washed with brine (20 mL), dried ($MgSO_4$), filtered and concentrated at reduced pressure. Purification by silica FCC (eluting with 20:80 heptane/EtOAc) gave the title compound (78 mg, 84% yield) as colourless oil.

LCMS data: Calculated $MH^+$ (234); Found 81% ($MH^+$) m/z 234, Rt=1.19 min (Method A).

$^1$H NMR (500 MHz, CHLOROFORM-d) δ ppm 8.48 (2 H, d, J=8.4 Hz), 8.19 (2 H, d, J=8.4 Hz), 4.80 (2 H, s), 3.94 (3 H, s), 1.77 (6 H, s).

Preparation of 4-(4,4-dimethyl-4,5-dihydro-1,3-oxazol-2-yl)benzoic acid

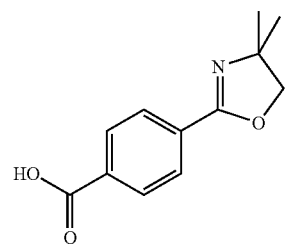 [SMILES: CC1(C)COC(c2ccc(C(=O)O)cc2)=N1]

To a solution of methyl 4-(4,4-dimethyl-4,5-dihydro-1,3-oxazol-2-yl)benzoate (78 mg, 0.33 mmol) in THF (1 mL) and $H_2O$ (1 mL) was added LiOH (23 mg, 1 mmol). The mixture was stirred at RT for 4 h before it was diluted with EtOAc (5 mL) and quenched by addition of aqueous HCl (5 ml of a 0.5 M aqueous solution, 2.5 mmol). After extraction with EtOAc (3×10 mL), the combined organic extracts were washed with brine (10 mL), dried ($MgSO_4$), filtered and concentrated at reduced pressure. The crude residue (12 mg, 16% yield) was obtained as colourless oil and was used without further purification.

LCMS data: Calculated $MH^+$ (220); Found 44% ($MH^+$) m/z 220, Rt=0.90 min (Method A).

$^1$H NMR (500 MHz, CHLOROFORM-d) δ ppm 8.16 (2 H, d, J=8.1 Hz), 8.09 (2 H, d, J=8.2 Hz), 4.22 (2 H, s), 1.47 (6 H, m).

Route 19

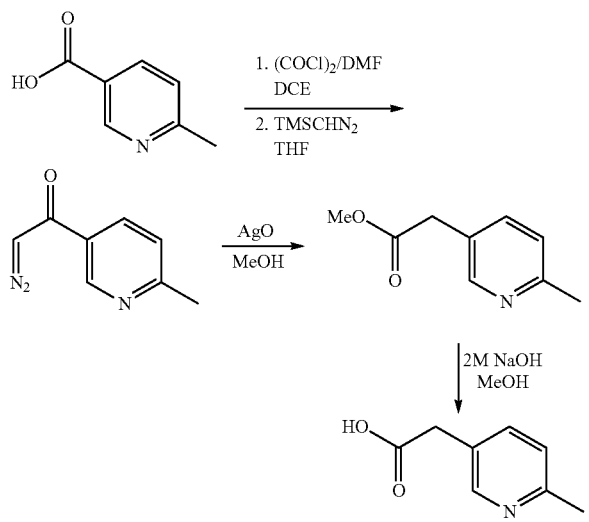

Preparation of
2-(diazynylidene)-1-(6-methylpyridin-3-yl)ethanone

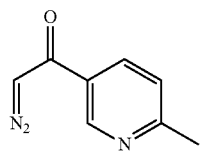

To a stirred solution of 6-methylnicotinic acid (200 mg, 1.46 mmol) in DCM (10 ml) at 0° C. was added oxalyl chloride (1.25 ml, 14.6 mmol) and DMF (2 drops) and the resulting solution was stirred at room temperature for 2 hours. The reaction was then concentrated at reduced pressure and then redissolved in DCM (10 ml) and cooled to 0° C. TMS diazomethane (1.45 ml of a 2M solution in THF, 2.9 mmol) and NEt₃ (0.38 ml, 2.9 mmol) were added slowly and the resulting solution was maintained at 5° C. for 12 hours. The reaction was then filtered and concentrated at reduced pressure to give the title compound (180 mg, 76%) as black oil that was used without further purification.

Preparation of methyl (6-methylpyridin-3-yl)acetate

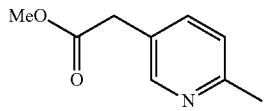

To a stirred solution of 2-(diazynylidene)-1-(6-methylpyridin-3-yl)ethanone (100 mg, 0.62 mmol) in methanol (5 ml) was added AgO (39 mg, 0.36 mmol) and the resulting solution was heated at 65° C. for 2 hours. The reaction was then cooled to room temperature, filtered through Celite® and concentrated at reduced pressure to yield the title product (60 mg, 58%) as orange oil which was used without further purification.

LCMS data: Calculated MH⁺ (166); Found 100% (MH⁺) m/z 166, Rt=0.79 min (Method C).

Preparation (6-methylpyridin-3-yl)acetic acid

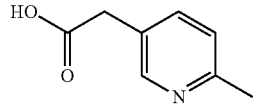

To a stirred solution of methyl (6-methylpyridin-3-yl)acetate (60 mg, 0.36 mmol) in methanol (5 ml) was added NaOH (1.0 ml of a 2M aqueous solution, 2.0 mmol) and the resulting solution was heated at 65° C. for 2 hours. The solvent was then removed at reduced pressure and the resulting residue was dissolved in methanolic HCl (5 ml) and then reconcentrated to yield the title product (54 mg, quant. yield) that was used without further purification.

LCMS data: Calculated MH⁺ (152); Found 100% (MH⁺) m/z 152, Rt=0.79 min. Method C.

Route 20

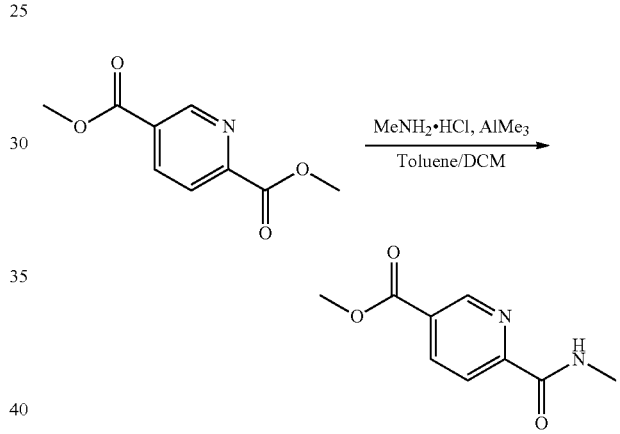

Preparation of methyl 6-(methylcarbamoyl)pyridine-3-carboxylate

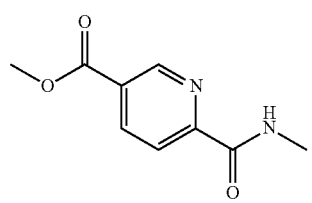

To a stirred solution of MeNH₂.HCl (173 mg, 5.12 mmol) in toluene (5 mL) at 0° C., was added AlMe₃ (2 M solution in Hexanes, 1.28 mL, 2.56 mmol). After 30 minutes the solution was canulated into a stirred solution dimethyl pyridine-2,5-dicarboxylate (500 mg, 2.56 mmol) in DCM (5 mL) at 0° C. before stirring over night at room temperature. An aliquot was taken and analysed by NMR, indicating that there was a 0.8:1 ratio of product to starting material. MeNH₂.HCl (173 mg, 5.124 mmol) and AlMe₃ (2M solution in Hexanes, 1.28 mL, 2.56 mmol) were added and the reaction stirred for 12 hours. The reaction was quenched by addition of H₂O (2 mL) and extracted with EtOAc (2×10 mL). The organics were combined, dried (MgSO₄), filtered and concentrated at reduced pressure to give the title compound (520 mg, quant. yield) which was used without further purification.

NMR data: ¹H NMR (250 MHz, CHLOROFORM-d) δ ppm 9.14 (1 H, d, J=1.8 Hz), 8.45 (1 H, dd, J=8.1, 2.1 Hz), 8.29 (1 H, d, J=8.1 Hz), 8.06 (1 H, br. s.), 3.99 (3H, s), 3.07 (3H, d).

Route 21

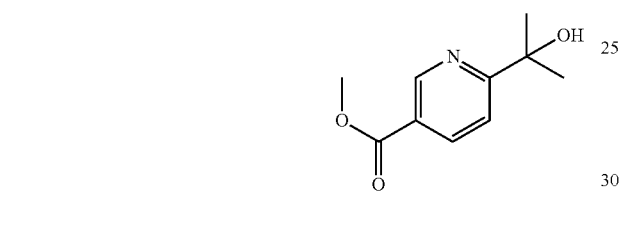

Preparation of methyl 6-(1-hydroxy-1-methylethyl)pyridine-3-carboxylate

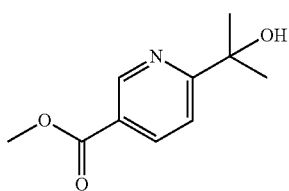

To a stirred solution of dimethyl pyridine-2,5-dicarboxylate (2.0 g, 10.25 mmol) in THF (40 mL) at −78° C. was added MeMgCl (3M sol in THF, 6.83 mL, 20.49 mmol). After 2 hours a second charge of MeMgCl (3.4 mL, 10.25 mmol) was added and a third (1.8 mL, 5.4 mmol) after a further 45 minutes. The reaction was deemed complete by TLC analysis and quenched by addition of saturated aqueous NH₄Cl (1 mL) and concentrated at reduced pressure. Purification by silica FCC (eluting with 80:20 Heptanes/EtOAc) gave the title compound (539 mg, 27% yield) as oil.

LCMS data: Calculated MH⁺ (196); Found 100% (MH⁺) m/z 196, Rt=1.24 min (Method B).

NMR data: ¹H NMR (500 MHz, CHLOROFORM-d) δ ppm 9.12 (1 H, d, J=1.2 Hz), 8.30 (1 H, dd, J=8.2, 2.1 Hz), 7.48 (1 H, d, J=8.4 Hz), 4.73 (1 H, br. s.), 3.96 (3 H, s), 1.56 (6 H, s).

Route 22

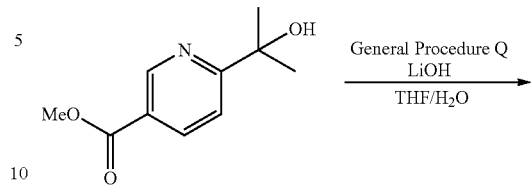

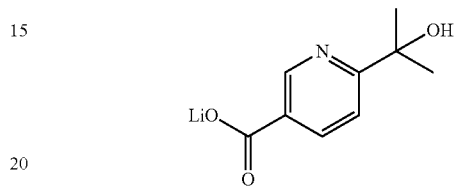

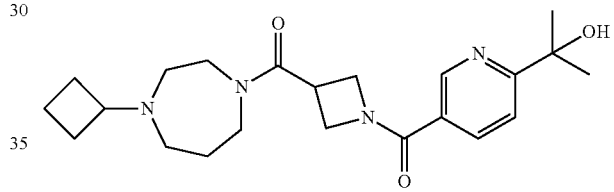

General Procedure Q

Preparation of lithium 6-(1-hydroxy-1-methylethyl)pyridine-3-carboxylate

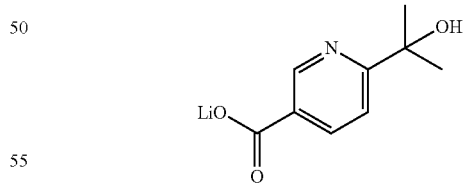

To a stirred solution of methyl 6-(1-hydroxy-1-methylethyl)pyridine-3-carboxylate (479 mg, 2.45 mmol) in THF, (10 mL) was added LiOH (2M aqueous solution, 1.35 mL, 2.70 mmol). After 4 hours the solvent was removed at reduced pressure to give the title compound (458 mg, 100%) that was used without further purification.

NMR data: ¹H NMR (500 MHz, MeOD) δ ppm 9.00 (1 H, d, J=1.4 Hz), 8.27 (1 H, dd, J=8.2, 2.1 Hz), 7.68 (1 H, d, J=8.2 Hz), 1.55 (6 H, s).

The following compound was prepared as described in Route 22, General Procedure Q above.

Preparation of lithium 6-(methylcarbamoyl)pyridine-3-carboxylate

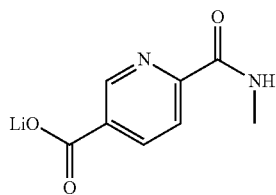

In a similar fashion (Route 24, GP Q), methyl 6-(methylcarbamoyl)pyridine-3-carboxylate (520 mg, 2.68 mmol) and LiOH (2 M aqueous solution, 1.47 mL, 2.95 mmol) in THF (10 mL) gave the title compound (498 mg, 100%) that was used without further purification.

NMR data: $^1$H NMR (250 MHz, MeOD) δ ppm 9.09 (1 H, dd, J=2.0, 0.8 Hz), 8.37 (1 H, dd, J=8.0, 2.1 Hz), 8.06 (1 H, dd, J=8.0, 0.8 Hz), 2.97 (3 H, s).

Preparation of lithium 3-fluoro-4-(1H-1,2,4-triazol-1-yl)benzoate

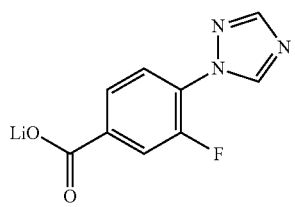

In a similar fashion (Route 24, GP Q), methyl 3-fluoro-4-(1H-1,2,4-triazol-1-yl)benzenecarboxylate (100 mg, 0.45 mmol) and LiOH (11.4 mg, 0.48 mmol) in THF (1 mL) and water (1 mL) gave the title compound (96 mg, 100%) as a white solid that was used without further purification.
General Procedure R Example 76

Preparation of 2-[5-({3-[(4-cyclobutyl-1,4-diazepan-1-yl)carbonyl]azetidin-1-yl}carbonyl)pyridin-2-yl]propan-2-ol. Potency Range A

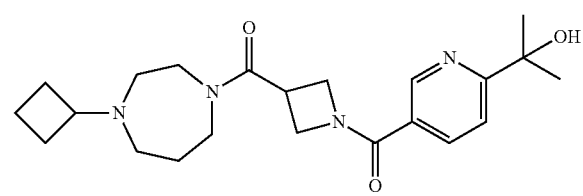 [SMILES: CC(C)(O)c1ccc(C(=O)N2CC(C(=O)N3CCCN(C4CCC4)CC3)C2)cn1]

To a stirred solution of lithium 6-(1-hydroxy-1-methylethyl)pyridine-3-carboxylate (50 mg, 0.28 mmol) and HOBt (42 mg, 0.30 mmol) in DMF (2 mL) was added HBTU, (117 mg, 0.30 mmol) and 1-(azetidin-3-ylcarbonyl)-4-cyclobutyl-1,4-diazepane (46 mg, 0.30 mmol). After 20 hours the reaction was absorbed onto an SCX column and the product eluted with 7M NH$_3$. Volatiles were removed at reduced pressure to give the title compound (1.4 mg, 1.2%) after purification by silica FCC (eluting with 90:9:1 Et$_2$O/MeOH/NH$_3$).

LCMS data: Calculated MH$^+$ (401); Found 100% (MH$^+$) m/z 401, Rt=3.44 min (Method D).

NMR data: $^1$H NMR (500 MHz, MeOD) δ ppm 8.77 (1 H, d, J=1.5 Hz), 8.06 (1 H, dd, J=8.3, 2.1 Hz), 7.79 (1 H, d, J=8.2 Hz), 4.57 (2 H, d, J=7.2 Hz), 4.36-4.43 (1 H, m), 4.27-4.35 (1 H, m), 3.89 (1 H, m), 3.59-3.69 (2 H, m), 3.44-3.50 (2 H, m), 3.35 (1 H, s), 2.96 (1 H, m), 2.58 (2 H, d, J=4.4 Hz), 2.45-2.53 (2 H, m), 2.04-2.12 (2 H, m), 1.79-1.95 (4 H, m), 1.62-1.75 (2 H, m), 1.52-1.58 (6 H, m).

The following compound was prepared as described in Route 22, General Procedure R above.

Example 77

5-({3-[(4-cyclobutyl-1,4-diazepan-1-yl)carbonyl]azetidin-1-yl}carbonyl)-N-methylpyridine-2-carboxamide. Potency Range A

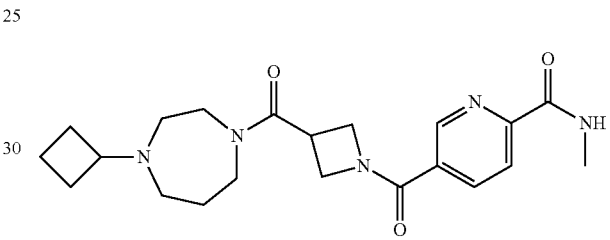

In a similar fashion (Route 24, GP R), lithium 6-(methylcarbamoyl)pyridine-3-carboxylate (50 mg, 0.28 mmol) and 1-(azetidin-3-ylcarbonyl)-4-cyclobutyl-1,4-diazepane (46 mg, 0.30 mmol) in DMF (2 mL) gave the title compound (35 mg, 21%).

LCMS data: Calculated MH$^+$ (400); Found 100% (MH$^+$) m/z 400, Rt=1.94 min (Method C).

NMR data: $^1$H NMR (500 MHz, CHLOROFORM-d) δ ppm 8.79 (1 H, s), 8.23 (1 H, d, J=7.9 Hz), 8.08 (1 H, dd, J=8.0, 1.8 Hz), 8.01 (1 H, br. s.), 4.67-4.82 (1 H, m), 4.24-4.50 (3 H, m), 3.57-3.77 (3 H, m), 3.30-3.42 (2 H, m), 2.98-3.10 (3 H, m), 2.78-2.93 (1 H, m), 2.32-2.60 (4 H, m), 1.49-2.11 (8 H, m).

Example 78

Preparation of 1-cyclobutyl-4-[(1-{[3-fluoro-4-(1H-1,2,4-triazol-1-yl)phenyl]carbonyl}azetidin-3-yl)carbonyl]-1,4-diazepane. Potency Range A

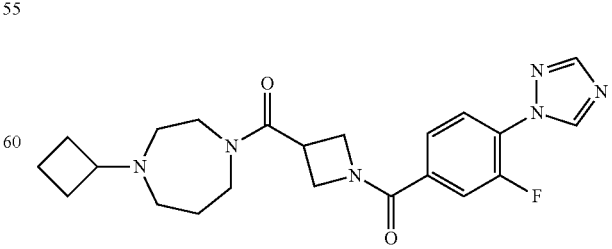

In a similar fashion (Route 24, GP R), lithium 3-fluoro-4-(1H-1,2,4-triazol-1-yl)benzoate (49 mg, 0.23 mmol) and 1-(azetidin-3-ylcarbonyl)-4-cyclobutyl-1,4-diazepane (50 mg, 0.21 mmol) in DMF (2 mL) and DIPEA (104 µL, 0.63 mmol) gave the title compound (16 mg, 17%) after purification by preparative HPLC (Method 2).

LCMS data: Calculated MH+ (427); Found 100% (MH+) m/z 427, Rt=3.52 min (Method D).

NMR data: $^1$H NMR (500 MHz, CHLOROFORM-d) δ ppm 8.76 (1 H, d, J=2.6 Hz), 8.15 (1 H, s), 8.03 (1 H, t, J=7.9 Hz), 7.65 (1 H, dd, J=11.8, 1.4 Hz), 7.60 (1 H, dd, J=8.4, 1.2 Hz), 4.80 (1 H, m), 4.35-4.58 (2 H, m), 4.31 (1 H, m), 3.56-3.82 (3 H, m), 3.39 (2 H, m), 2.76-2.96 (1 H, m), 2.50 (4 H, m), 2.03-2.13 (2 H, m), 1.86 (4 H, m), 1.52-1.75 (2 H, m).

Route 23

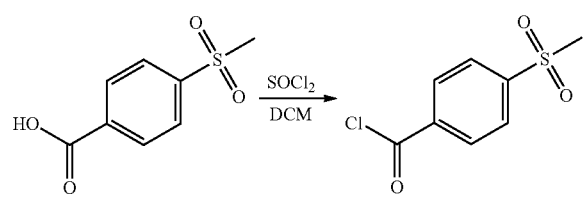

Preparation of 4-(methylsulfonyl)benzoyl chloride

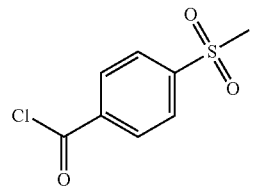

To a stirred solution of 4-methylsulphonylbenzoic acid (100 mg, 0.48 mmol) in DCM (2 mL) was added SOCl$_2$ (52 µL, 0.73 mmol) and toluene (2 mL) and the resulting reaction was stirred at 60° C. for 20 hours. A further charge of SOCl$_2$ (100 µL, 1.45 mmol) was added and the reaction was heated at 80° C. for a further 24 hours. Volatiles were removed at reduced pressure and the crude product used in subsequent steps without further purification.

Route 24

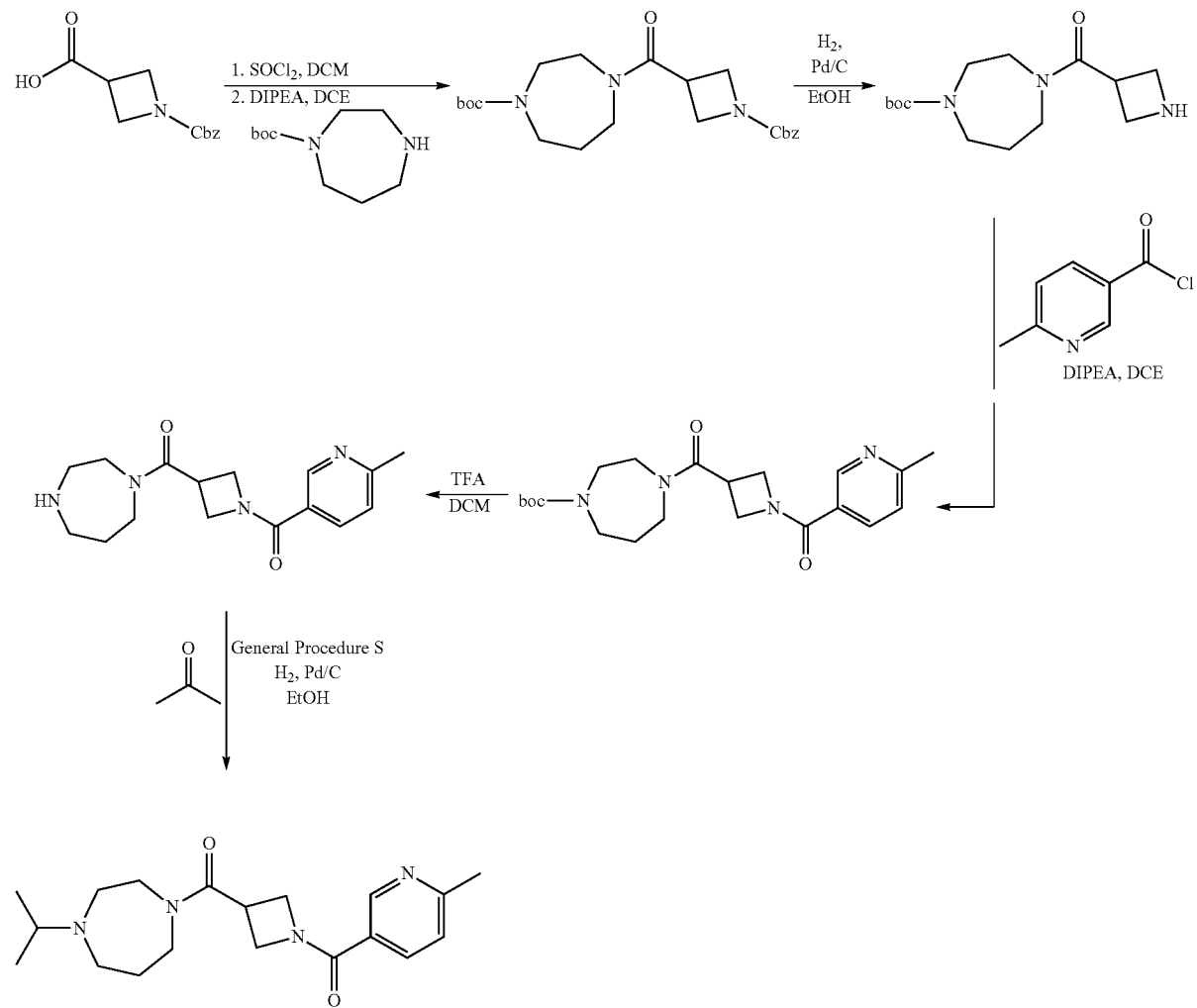

Preparation of tert-butyl 4-({1-[(benzyloxy)carbonyl]azetidin-3-yl}carbonyl)-1,4-diazepane-1-carboxylate

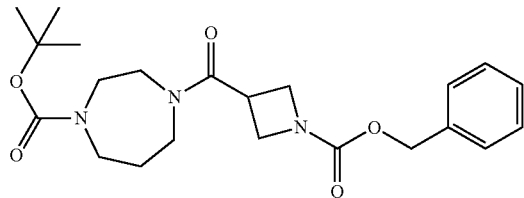 [SMILES: CC(C)(C)OC(=O)N1CCCN(C(=O)C2CN(C(=O)OCc3ccccc3)C2)CC1]

To a stirred solution of benzyl 3-[(4-cyclobutyl-1,4-diazepan-1-yl)carbonyl]azetidine-1-carboxylate (1.0 g, 4.25 mmol) in DCM (20 mL) was added SOCl$_2$ (0.754 g, 0.460 mL, 6.38 mmol) and the resulting mixture was stirred for 2 hours at room temperature. LCMS analysis showed incomplete conversion so a further 1.0 eq of SOCl$_2$ (501 mg, 305 μL) was added and the reaction stirred for a further 19 hours. Volatiles were removed at reduced pressure and the crude acid chloride dissolved in DCM (10 mL) and added dropwise to a solution of tert-butyl 1,4-diazepane-1-carboxylate (0.658 g, 5.10 mmol, 1.2 eq) and DIPEA (1.67 g, 12.75 mmol, 3.0 eq) in DCM (10 mL) at 0° C. The resulting solution was stirred at room temperature for 17 hours and then quenched by addition of NaHCO$_3$ (5 mL). The reaction was diluted with DCM (10 mL) and the phases separated. The organic was washed with brine (5 mL), dried (MgSO$_4$), filtered and concentrated at reduced pressure. Purification by silica FCC (eluting with 98:1.2:0.8 to 97:2.7:0.3 gradient of DCM/MeOH/NH$_3$) gave the title compound (1.54 g, 86%).

NMR data: $^1$H NMR (500 MHz, CHLOROFORM-d) δ ppm 7.28-7.40 (5 H, m), 5.04-5.15 (2 H, m), 4.18-4.39 (2 H, m), 4.13 (2 H, q, J=8.3 Hz), 3.22-3.74 (9 H, m), 1.75-1.91 (2 H, m), 1.37-1.51 (9 H, m).

Preparation of tert-butyl 4-(azetidin-3-ylcarbonyl)-1,4-diazepane-1-carboxylate

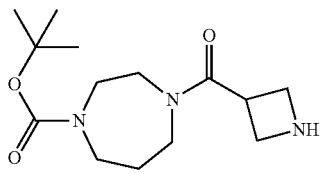 [SMILES: CC(C)(C)OC(=O)N1CCCN(C(=O)C2CNC2)CC1]

A stirred solution of tert-butyl 4-({1-[(benzyloxy)carbonyl]azetidin-3-yl}carbonyl)-1,4-diazepane-1-carboxylate (1.54 g, 3.69 mmol) in EtOH (10 mL) was purged with N$_2$ and charged with 10% Pd/C (154 mg, 10% wt/wt). The flask was purged with N$_2$ (N$_2$/vacuum cycle×3) and then H$_2$ (H$_2$/vacuum cycle×3). After 24 hours the reaction was incomplete by NMR analysis. The mixture was filtered through Celite®, fresh catalyst charged (154 mg, 10% wt/wt) and the hydrogenation resumed and after a further 24 and 48 hours this process was repeated. NMR analysis confirmed consumption of starting material and the reaction was filtered through Celite® and concentrated at reduced pressure to give the title compound (1.02 g, 98%).

NMR data: $^1$H NMR (500 MHz, MeOD) δ ppm 4.10-4.26 (3 H, m), 3.95-4.09 (1 H, m), 3.65-3.72 (1 H, m), 3.46-3.58 (4 H, m), 3.36-3.46 (4 H, m), 1.69-1.86 (2 H, m), 1.39-1.53 (9 H, m).

Preparation of tert-butyl 4-({1-[(6-methylpyridin-3-yl)carbonyl]azetidin-3-yl}carbonyl)-1,4-diazepane-1-carboxylate

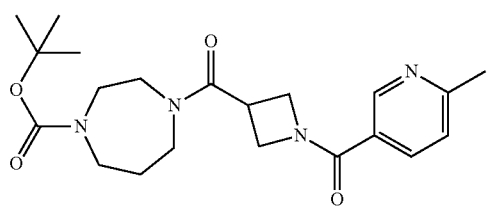 [SMILES: Cc1ccc(C(=O)N2CC(C(=O)N3CCCN(C(=O)OC(C)(C)C)CC3)C2)cn1]

To a stirred solution of tert-butyl 4-(azetidin-3-ylcarbonyl)-1,4-diazepane-1-carboxylate (1.02 g, 3.6 mmol) and DIPEA (1.41 g, 10.8 mmol) in DCM (20 mL) was added a solution of 6-methylpyridine-3-carbonyl chloride (420 mg, 4.32 mmol) in DCM (5 mL) at 0° C. After 3 hours the reaction was diluted with DCM (10 mL), washed with saturated aqueous NaHCO$_3$ (10 mL), brine (5 mL), dried (MgSO$_4$), filtered and concentrated at reduced pressure. Purification by silica FCC (eluting with 100:0:0 to 95:4.5:0.5 gradient of DCM/MeOH/NH$_3$) gave the title compound (527 mg, 36%) as an orange-brown oil.

NMR data: $^1$H NMR (500 MHz, CHLOROFORM-d) δ ppm 8.72 (1 H, br. s.), 7.87 (1 H, m), 7.18-7.25 (1 H, m), 4.58-4.80 (1 H, m), 4.36 (2 H, m), 4.23-4.33 (1 H, m), 3.53-3.81 (4 H, m), 3.17-3.44 (4 H, m), 2.59 (3 H, d, J=2.0 Hz), 1.71-2.00 (3 H, m), 1.36-1.62 (9 H, m).

Preparation of 1-({1-[(6-methylpyridin-3-yl)carbonyl]azetidin-3-yl}carbonyl)-1,4-diazepane

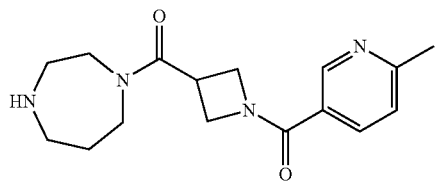 [SMILES: Cc1ccc(C(=O)N2CC(C(=O)N3CCCNCC3)C2)cn1]

To a stirred solution of tert-butyl 4-({1-[(6-methylpyridin-3-yl)carbonyl]azetidin-3-yl}carbonyl)-1,4-diazepane-1-carboxylate (455 mg, 1.13 mmol) in DCM (10 mL) was added TFA (440 μL, 5.65 mmol) and stirred at room temperature for 24 hours. The reaction was re-charged with TFA (0.5 mL, 6.5 mmol) and the reaction stirred for a further 5 hours until consumption of starting materials seen by TLC. Volatiles were removed at reduced pressure and the crude product shaken with Ambersep 900-OH resin in DCM (20 ml) for 2 hours. The resin was removed by filtration and the washings concentrated at reduced pressure to give the title compound (302 mg, 89%).

NMR data: $^1$H NMR (500 MHz, MeOD) δ ppm 8.66 (1 H, d, J=1.7 Hz), 7.95 (1 H, dd, J=8.1, 2.1 Hz), 7.38 (1 H, d, J=8.1 Hz), 4.51-4.58 (2 H, m), 4.32-4.40 (1 H, m), 4.24-4.32 (1 H, m), 3.86 (1 H, dt, J=15.0, 7.4 Hz), 3.77-3.81 (1 H, m), 3.61-3.70 (1 H, m), 3.50 (1 H, m), 3.20-3.30 (6 H, m), 2.55 (3 H, s), 1.93-2.10 (2 H, m).

General Procedure S

Example 79

Preparation of 1-(1-methylethyl)-4-({1-[(6-methylpyridin-3-yl)carbonyl]azetidin-3-yl}carbonyl)-1,4-diazepane. Potency Range C

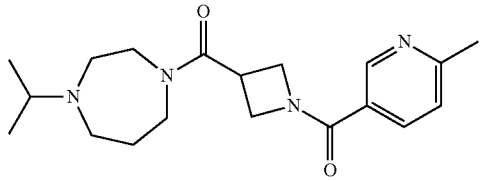 [SMILES: Cc1ccc(C(=O)N2CC(C(=O)N3CCCN(C(C)C)CC3)C2)cn1]

To a stirred solution of 1-({1-[(6-methylpyridin-3-yl)carbonyl]azetidin-3-yl}carbonyl)-1,4-diazepane (60 mg, 0.194 mmol) in EtOH (3 mL) was added Pd/C (10% wt/wt, 6 mg) and acetone (143 µL, 1.95 mmol). The flask was purged with $N_2$ ($N_2$/vacuum cycle×3) and then $H_2$ ($H_2$/vacuum cycle×3). After 24 hours the reaction was filtered through Celite® and concentrated at reduced pressure. Purification by silica FCC (90:9:1 $Et_2O$/MeOH/$NH_3$) and capture and release (SCX-2, flush with MeOH, then release with 7M $NH_3$ in MeOH) gave the title compound (18.4 mg, 27%).

LCMS data: Calculated $MH^+$ (345); Found 100% ($MH^+$) m/z 345. The product eluted in the solvent front (Method C).

NMR data: $^1H$ NMR (500 MHz, CHLOROFORM-d) δ ppm 8.74 (1 H, s), 7.88 (1 H, d, J=8.1 Hz), 7.22 (1 H, d, J=8.1 Hz), 4.74 (1 H, m), 4.34-4.44 (2 H, m), 4.27-4.33 (1 H, m), 3.59-3.71 (3 H, m), 3.36 (1 H, m), 3.32 (1 H, m), 2.85-2.99 (1 H, m), 2.64-2.74 (2 H, m), 2.55-2.63 (5 H, m), 1.74-1.89 (2 H, m), 0.99 (6 H, m).

The following compound was prepared as described in Route 24, General Procedure S above.

Example 80

Preparation of 1-ethyl-4-({1-[(6-methylpyridin-3-yl)carbonyl]azetidin-3-yl}carbonyl)-1,4-diazepane. Potency Range A

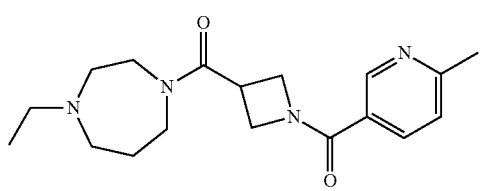 [SMILES: CCN1CCCN(C(=O)C2CN(C(=O)c3ccc(C)nc3)C2)CC1]

In a similar fashion (Route 24 GP S), 1-({1-[(6-methylpyridin-3-yl)carbonyl]azetidin-3-yl}carbonyl)-1,4-diazepane (70 mg, 0.23 mmol) and acetaldehyde (127 µL, 2.27 mmol) gave the title compound (13.9 mg, 18%).

LCMS data: Calculated $MH^+$ (331); Found 100% ($MH^+$) m/z 331. The product eluted in the solvent front (Method C).

NMR data: $^1H$ NMR (500 MHz, CHLOROFORM-d) δ ppm 8.72-8.79 (1 H, m), 7.89 (1 H, dt, J=8.0, 1.9 Hz), 7.22 (1 H, d, J=7.9 Hz), 4.74 (1 H, m), 4.35-4.45 (2 H, m), 4.26-4.34 (1 H, m), 3.60-3.76 (3 H, m), 3.33-3.43 (2 H, m), 2.67 (2 H, m), 2.60 (5 H, m), 2.51-2.57 (2 H, m), 1.81-1.95 (2 H, m), 1.06 (3 H, t, J=7.1 Hz).

Example 81

Preparation of 1-cyclopentyl-4-({1-[(6-methylpyridin-3-yl)carbonyl]azetidin-3-yl}carbonyl)-1,4-diazepane. Potency Range A

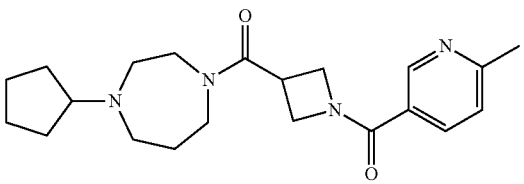 [SMILES: Cc1ccc(C(=O)N2CC(C(=O)N3CCCN(C4CCCC4)CC3)C2)cn1]

In a similar fashion (Route 24 GP S), 1-({1-[(6-methylpyridin-3-yl)carbonyl]azetidin-3-yl}carbonyl)-1,4-diazepane (60 mg, 0.194 mmol) and cyclopentanone (207 µL, 1.95 mmol) gave the title compound (39.7 mg, 55%).

LCMS data: Calculated $MH^+$ (371); Found 100% ($MH^+$) m/z 371. The product eluted in the solvent front (LCMS Method C).

NMR data: $^1H$ NMR (500 MHz, MeOD) δ ppm 8.69 (1 H, s), 7.99 (1 H, dt, J=8.1, 1.1 Hz), 7.41 (1 H, d, J=8.2 Hz), 4.52-4.60 (2 H, m), 4.35-4.42 (1 H, m), 4.25-4.33 (1 H, m), 3.85-3.95 (1 H, m), 3.59-3.71 (2 H, m), 3.43-3.51 (2 H, m), 2.89-3.00 (1 H, m), 2.82 (2 H, m), 2.68-2.76 (2 H, m), 2.59 (3 H, s), 1.80-1.96 (4 H, m), 1.69 (2 H, m), 1.53-1.63 (2 H, m), 1.36-1.48 (2 H, m).

Example 82

Preparation of 1-cyclohexyl-4-({1-[(6-methylpyridin-3-yl)carbonyl]azetidin-3-yl}carbonyl)-1,4-diazepane. Potency Range A

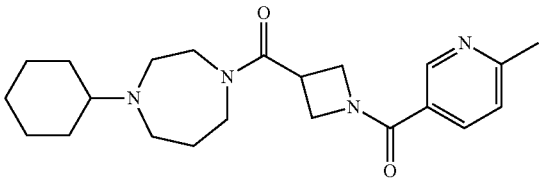 [SMILES: Cc1ccc(C(=O)N2CC(C(=O)N3CCCN(C4CCCCC4)CC3)C2)cn1]

In a similar fashion (Route 24 GP S), 1-({1-[(6-methylpyridin-3-yl)carbonyl]azetidin-3-yl}carbonyl)-1,4-diazepane (60 mg, 0.194 mmol) and cyclohexanone (201 µL, 1.95 mmol) gave the title compound (26.7 mg, 36%).

LCMS data: Calculated $MH^+$ (386). Found 100% ($MH^+$) m/z 386, Rt=2.04 (LCMS Method C).

NMR data: $^1H$ NMR (500 MHz, CHLOROFORM-d) δ ppm 8.76 (1 H, d, J=1.7 Hz), 7.85-7.93 (1 H, m), 7.21-7.26 (1 H, m), 4.70-4.78 (1 H, m), 4.35-4.49 (2 H, m), 4.22-4.35 (1 H, m), 3.57-3.79 (2 H, m), 3.43 (2 H, m), 2.65-3.26 (4 H, m), 2.61 (3 H, s), 1.77-2.13 (5 H, m), 1.53-1.76 (4 H, m), 1.19-1.44 (4 H, m), 1.04-1.18 (1 H, m).

Route 25

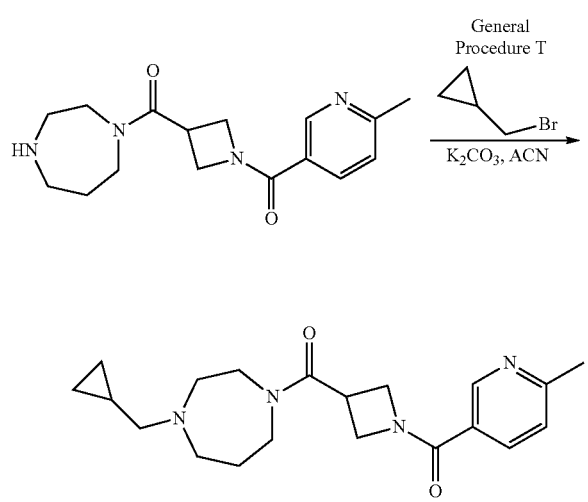

General Procedure T

Example 83

Preparation of 1-(cyclopropylmethyl)-4-({1-[(6-methylpyridin-3-yl)carbonyl]azetidin-3-yl}carbonyl)-1,4-diazepane. Potency Range C

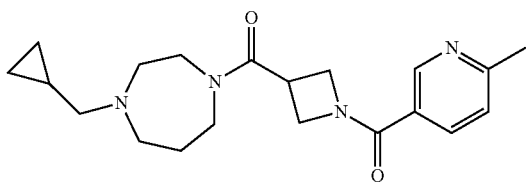 [SMILES: Cc1ccc(C(=O)N2CC(C(=O)N3CCCN(CC4CC4)CC3)C2)cn1]

To a stirred solution of 1-({1-[(6-methylpyridin-3-yl)carbonyl]azetidin-3-yl}carbonyl)-1,4-diazepane (100 mg, 0.33 mmol) and 1-(bromomethyl)cyclopropane (53 mg, 0.39 mmol) in ACN (5 mL) was added potassium carbonate (91 mg, 0.66 mmol). The mixture was heated to 70° C. in a sealed tube for 20 hours and then concentrated at reduced pressure. The crude residue was purified by silica FCC (eluting with 97:3:1 DCM/MeOH/NH$_3$) and then preparative HPLC (Method 2) to give the title compound (45 mg, 38% yield) as pale yellow oil LCMS data: Calculated MH$^+$ (357); Found 93% (MH$^+$) m/z 357, Rt=3.45 min. Method D. NMR data: $^1$H NMR (500 MHz, MeOD) δ ppm 8.70 (1 H, d, J=1.1 Hz), 7.99 (1 H, dd, J=8.1, 2.3 Hz), 7.41 (1 H, d, J=8.1 Hz), 4.57 (2 H, m), 4.22-4.46 (2 H, m), 3.83-3.97 (1 H, m), 3.57-3.75 (2 H, m), 3.40-3.56 (2 H, m), 2.65-2.89 (4 H, m), 2.59 (3 H, s), 2.35-2.45 (2 H, m), 1.78-2.01 (2 H, m), 0.80-0.96 (1 H, m), 0.46-0.63 (2 H, m), 0.05-0.20 (2 H, m).

The following compound was prepared as described in Route 25, General Procedure T above.

Example 84

Preparation of 1-(2-methylpropyl)-4-({1-[(6-methylpyridin-3-yl)carbonyl]azetidin-3-yl}carbonyl)-1,4-diazepane. Potency Range C

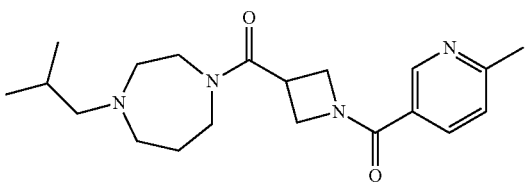 [SMILES: Cc1ccc(C(=O)N2CC(C(=O)N3CCCN(CC(C)C)CC3)C2)cn1]

In a similar fashion (Route 25, GP T), 1-({1-[(6-methylpyridin-3-yl)carbonyl]azetidin-3-yl}carbonyl)-1,4-diazepane (100 mg, 0.33 mmol) and 1-bromo-2-methylpropane (54 mg, 0.39 mmol) gave the title compound (25 mg, 21% yield) as pale yellow oil after purification by preparative HPLC (Method 2).

LCMS data: Calculated MH$^+$ (359). Found 89% (MH$^+$) m/z 359, Rt=3.98 min. Method D.

NMR data: $^1$H NMR (500 MHz, MeOD) δ ppm 8.70 (1 H, s), 7.99 (1 H, dt, J=8.2, 1.9 Hz), 7.41 (1 H, d, J=8.1 Hz), 4.49-4.62 (2 H, m), 4.23-4.45 (2 H, m), 3.83-3.94 (1 H, m), 3.56-3.69 (2 H, m), 3.40-3.51 (2 H, m), 2.67-2.76 (2 H, m), 2.54-2.67 (5 H, m), 2.21-2.30 (2 H, m), 1.68-1.96 (3 H, m), 0.85-0.95 (6 H, m).

Route 26

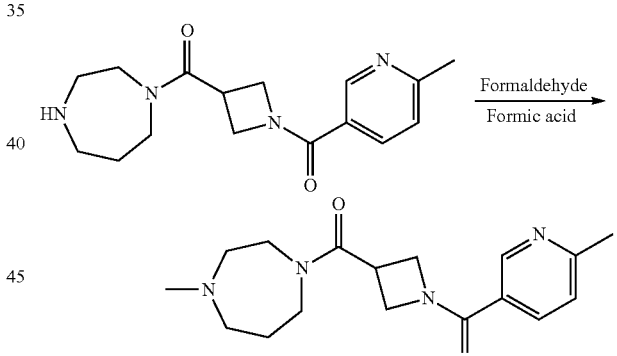

Example 85

Preparation of 1-methyl-4-({1-[(6-methylpyridin-3-yl)carbonyl]azetidin-3-yl}carbonyl)-1,4-diazepane. Potency Range D

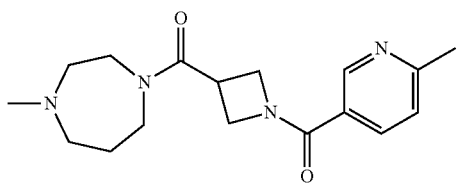

To a stirred solution of 1-({1-[(6-methylpyridin-3-yl)carbonyl]azetidin-3-yl}carbonyl)-1,4-diazepane (50 mg, 0.162 mmol) in formic acid (0.25 mL) was added formaldehyde (37% aq. sol., 0.097 mL, 1.296 mmol) and the reaction mixture was heated at 100° C. for 5 hours. Volatiles were then removed at reduced pressure to give the title compound (38 mg, 75%) after purification by silica FCC (eluting with 95:4.5:0.5 to 92.5:7.25:0.75 gradient of DCM/MeOH/NH$_3$).

LCMS data: Calculated MH$^+$ (317); Found 90% (MH$^+$) m/z 317, Rt=2.94 min (LCMS Method D).

NMR data: $^1$H NMR (500 MHz, MeOD) δ ppm 8.70 (1 H, d, J=1.8 Hz), 7.99 (1 H, m), 7.41 (1 H, d, J=8.1 Hz), 4.52-4.60 (2 H, m), 4.34-4.43 (1 H, m), 4.26-4.33 (1 H, m), 3.89 (1 H, m), 3.66-3.70 (1 H, m), 3.63 (1 H, m), 3.49 (1 H, m), 3.44-3.47 (1 H, m), 2.66-2.73 (2 H, m), 2.60-2.65 (2 H, m), 2.59 (3 H, s), 2.38 (3 H, m), 2.36-2.36 (1 H, m), 1.92-1.99 (1 H, m), 1.85-1.92 (1 H, m).

Route 27

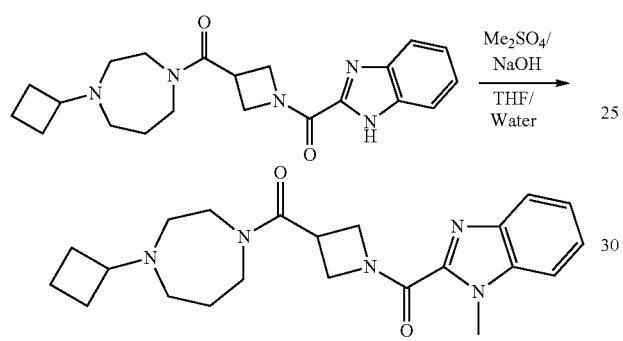

Example 86

Preparation of 2-({3-[(4-cyclobutyl-1,4-diazepan-1-yl)carbonyl]azetidin-1-yl}carbonyl)-1-methyl-1H-benzimidazole

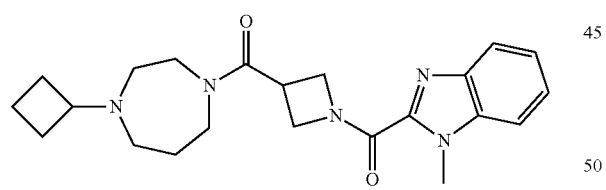

To a stirred solution of 2-({3-[(4-cyclobutyl-1,4-diazepan-1-yl)carbonyl]azetidin-1-yl}carbonyl)-1H-benzimidazole (170 mg, 0.45 mmol) in THF (10 ml) was added NaOH (1.12 ml of a 2.5 M aqueous solution, 2.8 mmol). After 5 minutes, dimethylsulfate (0.2 ml, 2.1 mmol) was added and the reaction was stirred at room temperature for 16 hours. The reaction was then concentrated at reduced pressure and purified directly via FCC (using a gradient of eluents; 98:2 to 95:5 DCM:2M NH$_3$ in MeOH) to give the title compound (45 mg, 25% yield) as yellow oil.

NMR data: $^1$H NMR (300 MHz, CHLOROFORM-d) δ ppm 7.70-7.80 (1 H, m), 7.20-7.45 (3 H, m), 5.00 (1 H, m), 4.86 (1 H, m), 4.55 (1 H, m), 4.35 (1 H, m), 4.15 (3 H, s), 3.55-3.80 (3 H, m), 3.30-3.45 (2 H, m), 2.85 (1 H, m), 2.30-2.60 (4 H, m), 2.00-2.15 (2 H, m), 1.50-1.95 (6 H, m).

Route 28

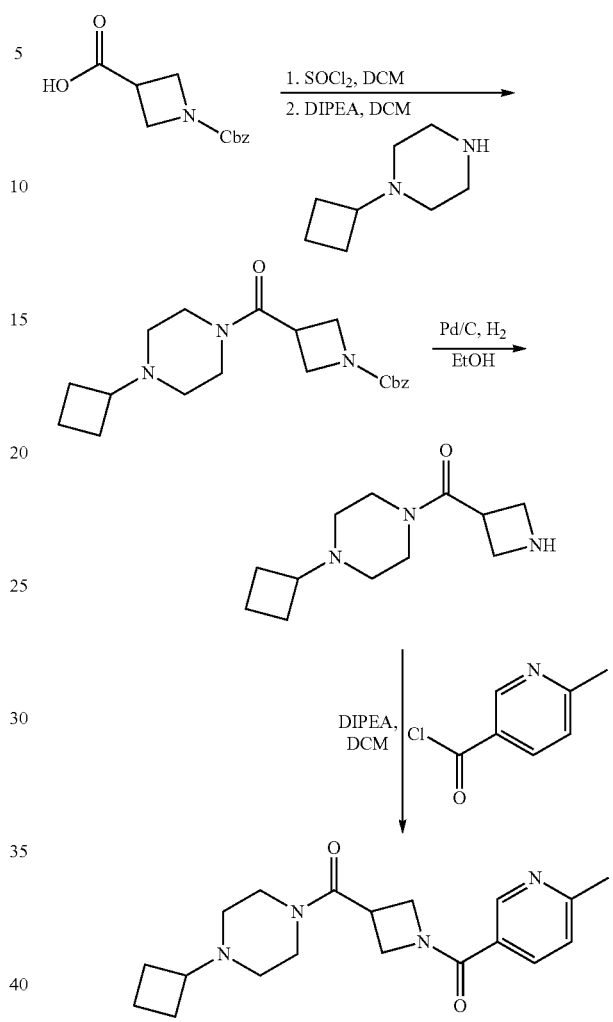

Preparation of benzyl 3-[(4-cyclobutylpiperazin-1-yl)carbonyl]azetidine-1-carboxylate

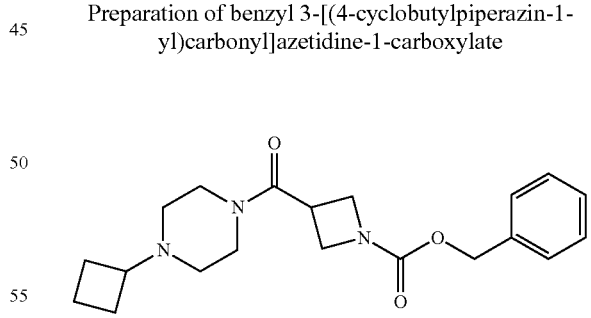

To a stirred solution of 1-[(benzyloxy)carbonyl]azetidine-3-carboxylic acid (250 mg, 1.06 mmol) in dichloromethane (2 mL) at RT was added SOCl$_2$ (115 μL, 1.59 mmol). The mixture was stirred for 18 hours before volatiles were removed at reduced pressure. The residue was then dissolved in dichlormethane (3 mL) and 1-cyclobutylpiperazine (115 mg, 1.28 mmol) followed by DIPEA (940 μL, 5.31 mmol) added. The mixture was stirred at RT for 4 hours and then quenched with saturated aq. NaHCO$_3$ (1 mL). The aqueous phase was extracted with dichloromethane (2×5 mL), the organics combined, washed with brine (2 mL), dried (MgSO$_4$), filtered and concentrated at reduced pressure to give the title compound (130 mg, 34%), after purification by silica FCC (97.5:2.25:0.25 DCM/MeOH/NH$_3$).

NMR data: $^1$H NMR (500 MHz, CHLOROFORM-d) δ ppm 7.30-7.44 (5 H, m), 5.09 (2 H, s), 4.21-4.39 (2 H, m), 4.08-4.19 (2 H, m), 3.57-3.79 (2 H, m), 3.44-3.57 (1 H, m), 3.16-3.38 (2 H, m), 2.54-2.83 (1 H, m), 2.20-2.40 (4 H, m), 1.98-2.15 (2 H, m), 1.80-1.97 (2 H, m), 1.65-1.80 (2 H, m)

Preparation of 1-(azetidin-3-ylcarbonyl)-4-cyclobutylpiperazine

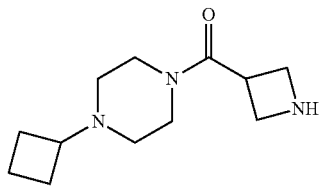 [SMILES: O=C(C1CNC1)N1CCN(C2CCC2)CC1]

To a stirred solution of benzyl 3-[(4-cyclobutylpiperazin-1-yl)carbonyl]azetidine-1-carboxylate (130 mg, 0.36 mmol) in EtOH (10 mL) was added 10% Pd/C (13 mg, 10% wt/wt). The flask was evacuated and the vacuum purged with N$_2$ gas. The flask was evacuated again and the vacuum purged with H$_2$ gas. After 16 hours the reaction mixture was filtered through Celite® and charged with 10% Pd/C (13 mg, 10% wt/wt). The flask was evacuated and the vacuum purged with N$_2$ gas. The flask was evacuated again and the vacuum purged with H$_2$ gas. After 23 hours, the reaction mixture was filtered through Celite® and the filtrate concentrated at reduced pressure to give the final compound (60 mg, 74%) which was used without further purification.

Example 87

1-cyclobutyl-4-({1-[(6-methylpyridin-3-yl)carbonyl]azetidin-3-yl}carbonyl)piperazine. Potency Range C

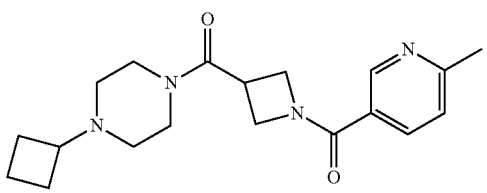 [SMILES: Cc1ccc(C(=O)N2CC(C(=O)N3CCN(C4CCC4)CC3)C2)cn1]

To a stirred solution of 1-(azetidin-3-ylcarbonyl)-4-cyclobutylpiperazine (60 mg, 0.27 mmol) in dichloromethane (1 mL) at 0° C., was added 6-methylpyridine-3-carbonyl chloride (31 mg, 0.32 mmol) and DIPEA (142 µL, 0.81 mmol). After 4 hours the reaction was quenched by addition of saturated aq. NaHCO$_3$ (1 mL) and the aqueous extracted with dichloromethane (2×5 mL), dried (MgSO$_4$), filtered, and concentrated at reduced pressure. Purification by silica FCC (eluting with 90:9:1 Et$_2$O/MeOH/NH$_3$) followed by capture and release on an SCX-2 cartridge (washing with MeOH and releasing with 7M NH$_3$ in MeOH) gave the title compound (17.8 mg, 19%)

LCMS data: Calculated MH$^+$ (343); Found 97% (MH$^+$) m/z 343, Rt=3.47 min (Method D).

$^1$H NMR (500 MHz, MeOD) δ ppm 8.69 (1 H, d, J=2.0 Hz), 7.98 (1 H, dd, J=8.2, 2.2 Hz), 7.41 (1 H, d, J=8.1 Hz), 4.49-4.66 (2 H, m), 4.32-4.50 (1 H, m), 4.22-4.32 (1 H, m), 3.79-3.96 (1 H, m), 3.53-3.75 (2 H, m), 3.36-3.50 (2 H, m), 2.72-2.98 (1 H, m), 2.59 (3 H, s), 2.27-2.47 (4 H, m), 2.01-2.21 (2 H, m), 1.84-2.02 (2 H, m), 1.58-1.84 (2 H, m)

Route 29

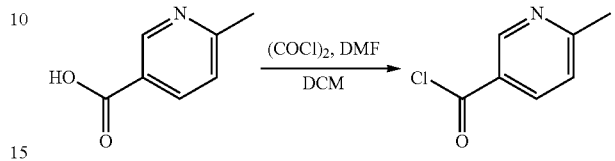

Preparation of 6-methylpyridine-3-carbonyl chloride

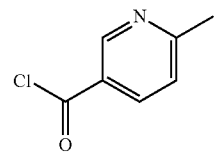

To a stirred solution of 6-methylpyridine-3-carboxylic acid (100 mg, 0.73 mmol) in DCM (2 mL) was added oxalyl chloride (120 µL, 1.46 mmol) and DMF (2 drops). After 2 hours the reaction mixture was concentrated at reduced pressure and the crude product used in subsequent steps without further purification.

The invention claimed is:
1. A compound of formula (I)

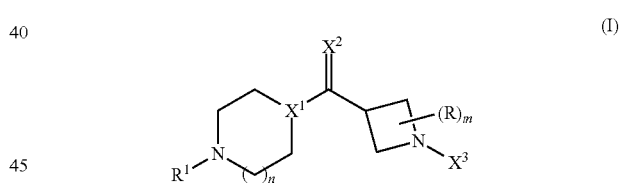

or a pharmaceutically acceptable salt, wherein
R$^1$ is C$_{1-5}$ alkyl; C$_{2-5}$ alkenyl; C$_{2-5}$ alkynyl; or T$^0$, wherein C$_{1-5}$ alkyl; C$_{2-5}$ alkenyl; C$_{2-5}$ alkynyl are optionally substituted with one or more substituents, which are the same or different and selected from the group consisting of halogen; OH; OCH$_3$; OCH$_2$F; OCHF$_2$; OCF$_3$; CN; and T$^0$;
T$^0$ is C$_{3-5}$ cycloalkyl; or 4 to 5 membered saturated heterocyclyl, wherein T$^0$ is optionally substituted with one or more substituents, which are the same or different and selected from the group consisting of halogen; C$_{1-5}$ alkyl; C$_{2-5}$ alkenyl; C$_{2-5}$ alkynyl; OH; O—C$_{1-5}$ alkyl; O—C$_{2-5}$ alkenyl; O—C$_{2-5}$ alkynyl; and CN, wherein C$_{1-5}$ alkyl; C$_{2-5}$ alkenyl; C$_{2-5}$ alkynyl; O—C$_{1-5}$ alkyl; O—C$_{2-5}$ alkenyl; and O—C$_{2-5}$ alkynyl are optionally substituted with one or more halogen, which are the same or different;
n is 2;
X$^1$ is N;
X$^2$ is O; S; N—CN; N—OH; or N—OC$_{1-4}$ alkyl;

101

$X^3$ is $(CH_2)_{n1}X^4(CH_2)_{n2}R^2$;

R is F;

m is 0, 1, 2, 3, or 4;

n1; n2 are independently selected from the group consisting of 0; 1; and 2;

$X^4$ is C(O); C(O)O; OC(O); O; C(O)N($R^{1a}$); N($R^{1a}$)C(O); S(O)$_2$N($R^{1a}$); N($R^{1a}$)S(O)$_2$; S(O)N($R^{1a}$); N($R^{1a}$)S(O); S(O)$_2$; S(O); N($R^{1a}$)S(O)$_2$N($R^{1b}$); S; N($R^{1a}$); N($R^{1a}$)C(O)N($R^{1b}$); N($R^{1a}$)C(O)O; or OC(O)N($R^{1a}$);

$R^{1a}$, $R^{1b}$ are independently selected from the group consisting of H; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more halogen, which are the same or different;

$R^2$ is H; T; or $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^3$, which are the same or different;

$R^3$ is halogen; CN; C(O)$R^4$; C(O)O$R^4$; O$R^4$; C(O)N($R^4 R^{4a}$); S(O)$_2$N($R^4 R^{4a}$); S(O)N($R^4 R^{4a}$); S(O)$_2 R^4$; S(O)$R^4$; N($R^4$)S(O)$_2$N($R^{4a}R^{4b}$); S$R^4$; N($R^4 R^{4a}$); NO$_2$; OC(O)$R^4$; N($R^4$)C(O)$R^{4a}$; N($R^4$)SO$_2 R^{4a}$; N($R^4$)S(O)$R^{4a}$; N($R^4$)C(O)N($R^{4a}R^{4b}$); N($R^4$)C(O)O$R^{4a}$; OC(O)N($R^4 R^{4a}$); or T;

$R^4$, $R^{4a}$, $R^{4b}$ are independently selected from the group consisting of H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^5$, which are the same or different;

$R^5$ is halogen; CN; C(O)$R^6$; C(O)O$R^6$; O$R^6$; C(O)N($R^6 R^{6a}$); S(O)$_2$N($R^6 R^{6a}$); S(O)N($R^6 R^{6a}$); S(O)$_2 R^6$; S(O)$R^6$; N($R^6$)S(O)$_2$N($R^{6a}R^{6b}$); S$R^6$; N($R^6 R^{6a}$); NO$_2$; OC(O)$R^6$; N($R^6$)C(O)$R^{6a}$; N($R^6$)SO$_2 R^{6a}$; N($R^6$)S(O)$R^{6a}$; N($R^6$)C(O)N($R^{6a}R^{6b}$); N($R^6$)C(O)O$R^{6a}$; OC(O)N($R^6 R^{6a}$); or T;

$R^6$, $R^{6a}$, $R^{6b}$ independently selected from the group consisting of H; T; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

T is phenyl; naphthyl; azulenyl; indenyl; indanyl; $C_{3-7}$ cycloalkyl; 3 to 7 membered heterocyclyl; or 7 to 11 membered heterobicyclyl, wherein T is optionally substituted with one or more $R^7$, which are the same or different;

$R^7$ is halogen; CN; C(O)O$R^8$; O$R^8$; C(O)$R^8$; C(O)N($R^8 R^{8a}$); S(O)$_2$N($R^8 R^{8a}$); S(O)N($R^8 R^{8a}$); S(O)$_2 R^8$; S(O)$R^8$; N($R^8$)S(O)$_2$N($R^{8a}R^{8b}$); S$R^8$; N($R^8 R^{8a}$); NO$_2$; OC(O)$R^8$; N($R^8$)C(O)$R^{8a}$; N($R^8$)S(O)$_2 R^{8a}$; N($R^8$)S(O)$R^{8a}$; N($R^8$)C(O)O$R^{8a}$; N($R^8$)C(O)N($R^{8a}R^{8b}$); OC(O)N($R^8 R^{8a}$); oxo (=O), where the ring is at least partially saturated; $T^1$; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^8$, $R^{8a}$, $R^{8b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{10}$, which are the same or different;

$R^9$, $R^{10}$ are independently selected from the group consisting of halogen; CN; C(O)$R^{11}$; C(O)O$R^{11}$; O$R^{11}$; C(O)N($R^{11}R^{11a}$); S(O)$_2$N($R^{11}R^{11a}$); S(O)N($R^{11}R^{11a}$); S(O)$_2 R^{11}$; S(O)$R^{11}$; N($R^{11}$)S(O)$_2$N($R^{11a}R^{11b}$); S$R^{11}$; N($R^{11}R^{11a}$); NO$_2$; OC(O)$R^{11}$; N($R^{11}$)C(O)$R^{11a}$; N($R^{11}$)SO$_2 R^{11a}$; N($R^{11}$)S(O)$R^{11a}$; N($R^{11}$)C(O)N($R^{11a}R^{11b}$); N($R^{11}$)C(O)O$R^{11a}$; OC(O)N($R^{11}R^{11a}$); and $T^1$;

102

$R^{11}$, $R^{11a}$; $R^{11b}$ are independently selected from the group consisting of H; $T^1$; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$T^1$ is phenyl; $C_{3-7}$ cycloalkyl; or 3 to 7 membered heterocyclyl, wherein $T^1$ is optionally substituted with one or more $R^{12}$, which are the same or different;

$R^{12}$ is halogen; CN; C(O)O$R^{13}$; O$R^{13}$; C(O)$R^{13}$; C(O)N($R^{13}R^{13a}$); S(O)$_2$N($R^{13}R^{13a}$); S(O)N($R^{13}R^{13a}$); S(O)$_2 R^{13}$; S(O)$R^{13}$; N($R^{13}$)S(O)$_2$N($R^{13a}R^{13b}$); S$R^{13}$; N($R^{13}R^{13a}$); NO$_2$; OC(O)$R^{13}$; N($R^{13}$)C(O)$R^{13a}$; N($R^{13}$)S(O)$_2 R^{13a}$; N($R^{13}$)S(O)$R^{13a}$; N($R^{13}$)C(O)O$R^{13a}$; N($R^{13}$)C(O)N($R^{13a}R^{13b}$); OC(O)N($R^{13}R^{13a}$); oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more halogen, which are the same or different;

$R^{13}$, $R^{13a}$, $R^{13b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same or different.

2. A compound of claim 1, wherein $R^1$ is $C_{1-5}$ alkyl; $C_{2-5}$ alkenyl; $C_{2-5}$ alkynyl; $C_{3-5}$ cycloalkyl; CH$_2$-cyclopropyl; CHF-cyclopropyl; CF$_2$-cyclopropyl; CH$_2$-cyclobutyl; CHF-cyclobutyl; CF$_2$-cyclobutyl; or 4 to 5 membered saturated heterocyclyl, wherein $C_{1-5}$ alkyl; $C_{2-5}$ alkenyl; $C_{2-5}$ alkynyl are optionally substituted with one or more substituents, which are the same or different and selected from the group consisting of halogen; OH; OCH$_3$; OCH$_2$F; OCHF$_2$; OCF$_3$; and CN, and wherein $C_{3-5}$ cycloalkyl; CH$_2$-cyclopropyl; CHF-cyclopropyl; CF$_2$-cyclopropyl; CH$_2$-cyclobutyl; CHF-cyclobutyl; CF$_2$-cyclobutyl; and 4 to 5 membered saturated heterocyclyl are optionally substituted with one or more substituents, which are the same or different and selected from the group consisting of halogen; OH; OCH$_3$; OCH$_2$F; OCHF$_2$; OCF$_3$; CN; CH$_3$; CH$_2$F; CHF$_2$; and CF$_3$.

3. A compound of claim 1, wherein $X^2$ is O.

4. A compound of claim 1, wherein m is 0.

5. A compound of claim 1, wherein n1; n2 are independently selected from the group consisting of 0; and 1.

6. A compound of claim 1, wherein $X^3$ is $(CH_2)_{n1}C(O)(CH_2)_{n2}R^2$; $(CH_2)_{n1}C(O)N(R^{1a})(CH_2)_{n2}R^2$; $(CH_2)_{n1}C(O)O(CH_2)_{n2}R^2$; $(CH_2)_{n1}S(O)_2(CH_2)_{n2}R^2$; $(CH_2)_{n1}S(O)_2N(R^{1a})(CH_2)_{n2}R^2$; or $(CH_2)_{n1}N(R^{1a})S(O)_2(CH_2)_{n2}R^2$.

7. A compound of claim 1, wherein $R^2$ is T; or CH$_2$OT.

8. A compound of claim 1, wherein T is phenyl; tetrahydropyranyl; morpholinyl; piperidinyl; pyridinyl; pyrimidinyl; pyrazinyl; pyrazolyl; cyclopropyl; cyclopentyl; cyclohexyl; or tetrahydroisoquinolinyl, wherein T is optionally substituted with one or more $R^7$, which are the same or different.

9. A compound of claim 1 selected from the group consisting of

Benzyl 3-[(4-cyclobutyl-1,4-diazepan-1-yl)carbonyl]azetidine-1-carboxylate;

1-cyclobutyl-4-{[1-(piperidin-1-ylcarbonyl)azetidin-3-yl]carbonyl}-1,4-diazepane;

1-cyclobutyl-4-{[1-(morpholin-4-ylcarbonyl)azetidin-3-yl]carbonyl}-1,4-diazepane;

1-cyclobutyl-4-{[1-(cyclohexyl carbonyl)azetidin-3-yl]carbonyl}-1,4-diazepane;

1-cyclobutyl-4-{[1-(tetrahydro-2H-pyran-4-ylcarbonyl)azetidin-3-yl]carbonyl}-1,4-diazepane;

4-({3-[(4-cyclobutyl-1,4-diazepan-1-yl)carbonyl]azetidin-1-yl}carbonyl)benzonitrile;

Methyl 5-({3-[(4-cyclobutyl-1,4-diazepan-1-yl)carbonyl]azetidin-1-yl}carbonyl)pyridine-2-carboxylate;
1-cyclobutyl-4-({1-[(2-methylpyrimidin-5-yl)carbonyl]azetidin-3-yl}carbonyl)-1,4-diazepane;
1-cyclobutyl-4-({1-[(5-methylpyrazin-2-yl)carbonyl]azetidin-3-yl}carbonyl)-1,4-diazepane;
1-cyclobutyl-4-({1-[(6-methylpyridin-3-yl)carbonyl]azetidin-3-yl}carbonyl)-1,4-diazepane;
1-cyclobutyl-4-{[(1-[4-(tetrahydro-2H-pyran-4-yloxy)phenyl]carbonyl}azetidin-3-yl)carbonyl]-1,4-diazepane;
1-cyclobutyl-4-[(1-{[6-(1H-imidazol-1-yl)pyridin-3-yl]carbonyl}azetidin-3-yl)carbonyl]-1,4-diazepane;
1-cyclobutyl-4-[(1-{[6-(1H-1,2,4-triazol-1-yl)pyridin-3-yl]carbonyl}azetidin-3-yl)carbonyl]-1,4-diazepane;
1-cyclobutyl-4-{[1-(1H-pyrazol-1-yl acetyl)azetidin-3-yl]carbonyl}-1,4-diazepane;
1-cyclobutyl-4-{[1-(piperidin-1-ylacetyl)azetidin-3-yl]carbonyl}-1,4-diazepane;
1-cyclobutyl-4-{[1-(morpholin-4-ylacetyl)azetidin-3-yl]carbonyl}-1,4-diazepane;
1-cyclobutyl-4-({1-[(1,1-dioxidothiomorpholin-4-yl)acetyl]azetidin-3-yl}carbonyl)-1,4-diazepane;
1-cyclobutyl-4-({1-[(3,3-difluoropyrrolidin-1-yl)acetyl]azetidin-3-yl}carbonyl)-1,4-diazepane;
1-cyclobutyl-4-({1-[(4,4-difluoropiperidin-1-yl)acetyl]azetidin-3-yl}carbonyl)-1,4-diazepane;
1-cyclobutyl-4-[(1-{[(6-methylpyridin-3-yl)oxy]acetyl}azetidin-3-yl)carbonyl]-1,4-diazepane;
4-(2-{3-[(4-cyclobutyl-1,4-diazepan-1-yl)carbonyl]azetidin-1-yl}-2-oxoethoxy)benzonitrile;
1-cyclobutyl-4-({1-[(4-methoxyphenyl)sulfonyl]azetidin-3-yl}carbonyl)-1,4-diazepane;
1-cyclobutyl-4-{[1-(cyclohexylsulfonyl)azetidin-3-yl]carbonyl}-1,4-diazepane;
1-cyclobutyl-4-({1-[(cyclopentylmethyl)sulfonyl]azetidin-3-yl}carbonyl)-1,4-diazepane;
1-cyclobutyl-4-{[1-(phenylsulfonyl)azetidin-3-yl]carbonyl}-1,4-diazepane;
4-({3-[(4-cyclobutyl-1,4-diazepan-1-yl)carbonyl]azetidin-1-yl}sulfonyl)benzonitrile;
1-cyclobutyl-4-({1-[(4-methoxycyclohexyl)carbonyl]azetidin-3-yl}carbonyl)-1,4-diazepane;
1-cyclobutyl-4-({1-[(4,4-difluorocyclohexyl)carbonyl]azetidin-3-yl}carbonyl)-1,4-diazepane;
1-cyclobutyl-4-{[(1-[4-(3,5-dimethyl-1H-pyrazol-1-yl)phenyl]carbonyl}azetidin-3-yl)carbonyl]-1,4-diazepane;
1-cyclobutyl-4-[(1-{[4-(5-methyl-1,3,4-oxadiazol-2-yl)phenyl]carbonyl}azetidin-3-yl)carbonyl]-1,4-diazepane;
1-cyclobutyl-4-{[1-(cyclopropylacetyl)azetidin-3-yl]carbonyl}-1,4-diazepane;
1-cyclobutyl-4-{[1-(cyclohexylacetyl)azetidin-3-yl]carbonyl}-1,4-diazepane;
4-(2-{3-[(4-cyclobutyl-1,4-diazepan-1-yl)carbonyl]azetidin-1-yl}-2-oxoethyl)benzonitrile;
1-cyclobutyl-4-{[(1-[4-(1,3-thiazol-2-yl)phenyl]carbonyl}azetidin-3-yl)carbonyl]-1,4-diazepane;
1-cyclobutyl-4-[(1-{[4-(2-methyl-1,3-thiazol-4-yl)phenyl]carbonyl}azetidin-3-yl)carbonyl]-1,4-diazepane;
1-cyclobutyl-4-[(1-{[4-(5-methyl-1,2,4-oxadiazol-3-yl)phenyl]carbonyl}azetidin-3-yl)carbonyl]-1,4-diazepane;
1-cyclobutyl-4-[(1-{[4-(1-methylethyl)phenyl]carbonyl}azetidin-3-yl)carbonyl]-1,4-diazepane;
1-cyclobutyl-4-({1-[(4-phenoxyphenyl)carbonyl]azetidin-3-yl}carbonyl)-1,4-diazepane;
1-cyclobutyl-4-[(1-{[4-(1H-pyrazol-1-yl)phenyl]carbonyl}azetidin-3-yl)carbonyl]-1,4-diazepane;
1-cyclobutyl-4-[(1-{[4-(3-methyl-1,2,4-oxadiazol-5-yl)phenyl]carbonyl}azetidin-3-yl)carbonyl]-1,4-diazepane;
1-cyclobutyl-4-[(1-{[4-(4,4-dimethyl-4,5-dihydro-1,3-oxazol-2-yl)phenyl]carbonyl}azetidin-3-yl)carbonyl]-1,4-diazepane;
1-cyclobutyl-4-({1-[(6-methylpyridin-3-yl)acetyl]azetidin-3-yl}carbonyl)-1,4-diazepane;
1-cyclobutyl-4-({1-[(4-pyridin-3-ylphenyl)carbonyl]azetidin-3-yl}carbonyl)-1,4-diazepane;
1-cyclobutyl-4-({1-[(4-pyridin-4-ylphenyl)carbonyl]azetidin-3-yl}carbonyl)-diazepane;
1-cyclobutyl-4-[(1-{[3-(2-methyl-1,3-thiazol-4-yl)phenyl]carbonyl}azetidin-3-yl)carbonyl]-1,4-diazepane;
2-({3-[(4-cyclobutyl-1,4-diazepan-1-yl)carbonyl]azetidin-1-yl}carbonyl)-1H-benzimidazole;
5-({3-[(4-cyclobutyl-1,4-diazepan-1-yl)carbonyl]azetidin-1-yl}carbonyl)-1-methyl-1H-benzimidazole;
5-({3-[(4-cyclobutyl-1,4-diazepan-1-yl)carbonyl]azetidin-1-yl}carbonyl)-1-methyl-1H-benzotriazole;
7-({3-[(4-cyclobutyl-1,4-diazepan-1-yl)carbonyl]azetidin-1-yl}carbonyl)imidazo[1,2-α]pyridine;
1-cyclobutyl-4-{[1-(1H-1,2,4-triazol-3-ylcarbonyl)azetidin-3-yl]carbonyl}-1,4-diazepane;
1-cyclobutyl-4-({1-[(1-methyl-1H-pyrazol-4-yl)carbonyl]azetidin-3-yl}carbonyl)-1,4-diazepane;
1-cyclobutyl-4-{[1-(tetrahydro-2H-pyran-4-ylacetyl)azetidin-3-yl]carbonyl}-1,4-diazepane;
1-({1-[(4-chlorophenyl)acetyl]azetidin-3-yl}carbonyl)-4-cyclobutyl-1,4-diazepane;
1-cyclobutyl-4-[(1-{[4-(methylsulfonyl)phenyl]carbonyl}azetidin-3-yl)carbonyl]-1,4-diazepane;
3-[(4-cyclobutyl-1,4-diazepan-1-yl) carbonyl]-N-(cyclohexylmethyl)azetidine-1-carboxamide;
3-[(4-cyclobutyl-1,4-diazepan-1-yl)carbonyl]-N-(tetrahydro-2H-pyran-4-ylmethyl)azetidine-1-carboxamide;
3-[(4-cyclobutyl-1,4-diazepan-1-yl)carbonyl]-N-(4-fluorobenzyl)azetidine-1-carboxamide;
N-(4-cyanophenyl)-3-[(4-cyclobutyl-1,4-diazepan-1-yl)carbonyl]azetidine-1-carboxamide
3-[(4-cyclobutyl-1,4-diazepan-1-yl)carbonyl]-N-(cyclohexylmethyl)-N-methylazetidine-1-carboxamide;
3-[(4-cyclobutyl-1,4-diazepan-1-yl)carbonyl]-N-methyl-N-(tetrahydro-2H-pyran-4-ylmethyl)azetidine-1-carboxamide;
3-[(4-cyclobutyl-1,4-diazepan-1-yl)carbonyl]N-(4-fluorobenzyl)-N-methylazetidine-1-carboxamide;
3-[(4-cyclobutyl-1,4-diazepan-1-yl)carbonyl]-N-(4-fluorobenzyl)-N-methylazetidine-1-carboxamide;
N-(4-cyanobenzyl)-3-[(4-cyclobutyl-1,4-diazepan-1-yl)carbonyl]-N-methylazetidine-1-carboxamide;
4-nitrophenyl 3-[(4-cyclobutyl-1,4-diazepan-1-yl)carbonyl]azetidine-1-carboxylate;
2-({3-[(4-cyclobutyl-1,4-diazepan-1-yl)carbonyl]azetidin-1-yl}carbonyl)-1,2,3,4-tetrahydroisoquinoline;
N-(4-cyanobenzyl)-3-[(4-cyclobutyl-1,4-diazepan-1-yl)carbonyl]azetidine-1-carboxamide;
4-chlorophenyl 3-[(4-cyclobutyl-1,4-diazepan-1-yl)carbonyl]azetidine-1-carboxylate;
6-methylpyridin-3-yl 3-[(4-cyclobutyl-1,4-diazepan-1-yl)carbonyl]azetidine-1-carboxylate;
4-cyanophenyl 3-[(4-cyclobutyl-1,4-diazepan-1-yl)carbonyl]azetidine-1-carboxylate;

1-[(1-acetylazetidin-3-yl)carbonyl]-4-cyclobutyl-1,4-diazepane;

1-cyclobutyl-4-[(1-propanoylazetidin-3-yl)carbonyl]-1,4-diazepane;

1-cyclobutyl-4-[(1-{[4-(1H-imidazol-1-yl)phenyl]carbonyl}azetidin-3-yl)carbonyl]-1,4-diazepane;

1-cyclobutyl-4-[(1-{[4-(1H-1,2,4-triazol-1-yl)phenyl]carbonyl}azetidin-3-yl)carbonyl]-1,4-diazepane;

1-cyclobutyl-4-[(1-{[4-(1H-1,2,4-triazol-1-ylmethyl)phenyl]carbonyl}azetidin-3-yl)carbonyl]-1,4-diazepane;

1-cyclobutyl-4-({1-[(2-methylpyridin-4-yl)carbonyl]azetidin-3-yl}carbonyl)-1,4-diazepane;

2-[5-({3-[(4-cyclobutyl-1,4-diazepan-1-yl)carbonyl]azetidin-1-yl}carbonyl)pyridin-2-yl]propan-2-ol;

5-({3-[(4-cyclobutyl-1,4-diazepan-1-yl)carbonyl]azetidin-1-yl}carbonyl)-N-methylpyridine-2-carboxamide;

1-cyclobutyl-4-[(1-{[3-fluoro-4-(1H-1,2,4-triazol-1-yl)phenyl]carbonyl}azetidin-3-yl)carbonyl]-1,4-diazepane;

1-(1-methylethyl)-4-({1-[(6-methylpyridin-3-yl)carbonyl]azetidin-3-yl}carbonyl)-1,4-diazepane;

1-ethyl-4-({1-[(6-methylpyridin-3-yl)carbonyl]azetidin-3-yl}carbonyl)-1,4-diazepane;

1-cyclopentyl-4-({1-[(6-methylpyridin-3-yl)carbonyl]azetidin-3-yl}carbonyl)-1,4-diazepane;

1-cyclohexyl-4-({1-[(6-methylpyridin-3-yl)carbonyl]azetidin-3-yl}carbonyl)-1,4-diazepane;

1-(cyclopropylmethyl)-4-({1-[(6-methylpyridin-3-yl)carbonyl]azetidin-3-yl}carbonyl)-1,4-diazepane;

1-(2-methylpropyl)-4-({1-[(6-methylpyridin-3-yl)carbonyl]azetidin-3-yl}carbonyl)-1,4-diazepane;

1-methyl-4-({1-[(6-methylpyridin-3-yl)carbonyl]azetidin-3-yl}carbonyl)-1,4-diazepane; and 2-({3-[(4-cyclobutyl-1,4-diazepan-1-yl)carbonyl]azetidin-1-yl}carbonyl)-1-methyl-1H-benzimidazole.

10. A pharmaceutical composition comprising at least one compound or a pharmaceutically acceptable salt thereof of claim 1 together with a pharmaceutically acceptable carrier.

11. A method for treating, controlling, or delaying in a mammalian patient in need of the treatment disease associated with the H3 receptor, wherein the method comprises the administration to said patient a therapeutically effective amount of a compound of claim 1 or a pharmaceutically acceptable salt thereof, wherein the disease is allergic rhinitis.

12. A method for treating, controlling, or delaying in a mammalian patient in need of the treatment of allergic rhinitis, wherein the method comprises the administration to said patient a therapeutically effective amount of a compound of claim 1 or a pharmaceutically acceptable salt thereof.

13. A method for the preparation of a compound of claim 1, comprising the steps of reacting a compound of formula (Ia)

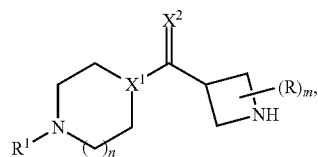

(Ia)

wherein $R^1$, n, $X^1$, $X^2$, R, m have the meaning as indicated in claim 1 with (i) an activated ester or anhydride of a compound of formula $R^2(CH_2)_{n2}C(O)OH$ in the presence of amide coupling reagents to yield a compound of formula (I), wherein n1=0 and $X^4$ is C(O); or (ii) a compound of formula $R^2(CH_2)_{n2}NCO$ to yield a compound of formula (I), wherein n1=0 and $X^4$ is C(O)NH; or (iii) a compound of formula $R^2(CH_2)_{n2}S(O)_2(CH_2)_{n1}$-halide in the presence of a base to yield a compound of formula (I), wherein n1=0 to 2 and $X^4$ is $S(O)_2$; or (iv) a compound of formula $R^2(CH_2)_{n2}(R^{1a})NC(O)(CH_2)_{n1}$-halide in the presence of a base to yield a compound of formula (I), wherein n1 is 0 to 2 and $X^4$ is $C(O)N(R^{1a})$; or (v) a compound of formula $R^2(CH_2)_{n2}OC(O)(CH_2)_{n1}$-halide in the presence of a base to yield a compound of formula (I), wherein n1=0 to 2 and $X^4$ is C(O)O; or (vi) a compound of formula $R^2(CH_2)_{n2}(R^{1a})NS(O)_2(CH_2)_{n1}$-halide in the presence of a base to yield a compound of formula (I), wherein n1=0 to 2 and $X^4$ is $S(O)_2N(R^{1a})$; or (vii) (aa) an intermediate compound of formula (XV)

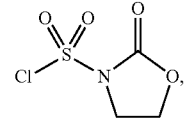

(XV)

resulting from the reaction of 2-chloroethanol with isocyanatosulfuryl chloride in the presence of a base; followed by (bb) reacting the resulting intermediate from step (aa) with a compound of formula $HN(R^{1a})(CH_2)_{n2}R^2$ in the presence of a base at elevated temperature to yield a compound of formula (I), wherein n1=0 and $X^4$ is $S(O)_2N(R^{1a})$; or (viii) a compound of formula $R^2(CH_2)_{n2}C(O)(CH_2)_{n1}$-halide in the presence of a base and optionally at elevated temperature to yield a compound of formula (I), wherein n1=1 to 2 and $X^4$ is C(O); or (ix) an intermediate compound of formula (XVa)

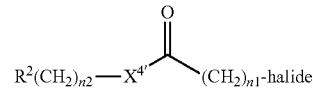

(XVa)

resulting from the reaction of a compound of formula $ClC(O)(CH_2)_{n1}$-halide in the presence of base optionally at elevated temperature with a compound of formula $R^2(CH_2)_{n2}X^{4'}H$, wherein n1=1 to 2 and $X^{4'}$ is O, NH or $NR^{1a}$; or (x) an intermediate compound of formula (XVb)

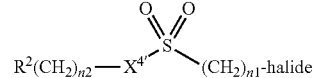

(XVb)

resulting from the reaction of a compound of formula $ClS(O)_2(CH_2)_{n1}$-halide in the presence of a base and a compound of formula $R^2(CH_2)_{n2}X^{4'}H$, wherein n1=1 to 2 and $X^4$ is NH or $NR^{1a}$.

14. A method for the preparation of a compound of claim 1, wherein in formula (I) $X^1$ is N; $X^2$ is O, n1 is 0, $X^4$ is C(O), comprising the steps of
  (a) protecting the amino group of a compound of formula (IIa) by reacting the amino group with a suitable chloroformate

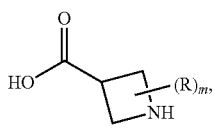
(IIa)

wherein R, m have the meaning as indicated in claim 1;
  (b) reacting the carboxylic acid group of the resulting carbamate compound from step (a) with a compound of formula (III)

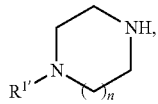
(III)

wherein n has the meaning as indicated in claim 1 and $R^1$ is $R^1$ as indicated in claim 1 or as suitable N-atom protecting group using standard amide coupling conditions and reagents to yield a compound of formula (I), optionally after removal of the protecting group and reacting the liberated amino group with a compound of formula $R^1$=O, wherein the oxo group is attached to a carbon atom of $R^1$, followed by reduction of the resulting imine; and
  (c) deprotecting the azetidine amino group of the resulting compound from step (b) to form a compound represented by formula (IVb)

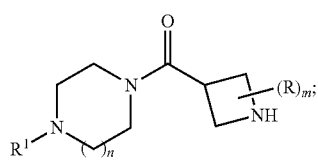
(IVb)

(d) reacting the resulting secondary amino group from step (c) with an acid chloride of formula $ClC(O)(CH_2)_{n2}R^2$ in the presence of a suitable base to yield a compound of formula (I), wherein n2, $R^2$ are defined as indicated in claim 1.

* * * * *